(12) United States Patent
Nicolson et al.

(10) Patent No.: US 6,951,894 B1
(45) Date of Patent: *Oct. 4, 2005

(54) EXTENDED WEAR OPHTHALMIC LENS

(75) Inventors: Paul Clement Nicolson, Dunwoody, GA (US); Richard Carlton Baron, Alpharetta, GA (US); Peter Chabrecek, Basel (CH); John Court, Ultimo (AU); Angelika Domschke, Lörrach (DE); Hans Jörg Griesser, The Patch (AU); Arthur Ho, Randwick (AU); Jens Höpken, Lörrach (CH); Bronwyn Glenice Laycock, Heidelberg Heights (AU); Qin Liu, Duluth, GA (US); Dieter Lohmann, Munchestein (CH); Gordon Francis Meijs, Murrumbeena (AU); Eric Papaspiliotopoulos, Paddington (AU); Judy Smith Riffle, Blacksburg, VA (US); Klaus Schindhelm, Cherrybrook (AU); Deborah Sweeney, Roseville (AU); Wilson Leonard Terry, Jr., Alpharetta, GA (US); Jürgen Vogt, Fribourg (CH); Lynn Cook Winterton, Alpharetta, GA (US)

(73) Assignee: CIBA Vision Corporation, Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/640,526

(22) Filed: Aug. 17, 2000

Related U.S. Application Data

(63) Continuation of application No. 09/262,542, filed on Mar. 4, 1999, now abandoned, which is a continuation of application No. 09/108,714, filed on Jul. 1, 1998, now Pat. No. 5,965,631, which is a division of application No. 08/682,452, filed on Jul. 17, 1996, now Pat. No. 5,849,811, which is a division of application No. 08/569,816, filed on Dec. 8, 1995, now Pat. No. 5,760,100, which is a continuation-in-part of application No. 08/301,166, filed on Sep. 6, 1994, now abandoned.

(30) Foreign Application Priority Data

Apr. 4, 1995 (DE) ............................................ 95810221
May 19, 1995 (CH) ................................................ 1496/95

(51) Int. Cl.$^7$ ................................................ C08K 3/00
(52) U.S. Cl. ........................ 523/107; 523/106; 523/108
(58) Field of Search ................................ 523/106, 107

(56) References Cited

U.S. PATENT DOCUMENTS

| | | | |
|---|---|---|---|
| 2,718,516 A | 9/1955 | Bortnick | |
| 3,284,406 A | 11/1966 | Nelson | |
| 3,518,324 A | 6/1970 | Polmanteer | |
| 3,700,573 A | 10/1972 | Laizler | |
| 3,708,225 A | 1/1973 | Misch et al. | |
| 3,808,178 A | 4/1974 | Gaylord | |
| 3,916,033 A | 10/1975 | Merrill | |
| 3,935,342 A | 1/1976 | Lim | |
| 3,959,102 A | 5/1976 | Wajs et al. | |
| 3,959,105 A | 5/1976 | Feneberg et al. | |
| 3,996,187 A | 12/1976 | Travnicek | |
| 4,008,198 A | 2/1977 | Krohberger et al. | |
| 4,062,627 A | 12/1977 | Wajs et al. | |
| 4,095,878 A | 6/1978 | Fanti | |
| 4,099,859 A | 7/1978 | Merrill | |
| 4,112,207 A | 9/1978 | Jones | |
| 4,114,993 A | 9/1978 | Travnicek | |
| 4,120,570 A | 10/1978 | Gaylord | |
| 4,128,318 A | 12/1978 | Sieglaff et al. | |
| 4,136,250 A | 1/1979 | Mueller et al. | |
| 4,143,949 A | 3/1979 | Chen | |
| 4,152,508 A | 5/1979 | Ellis et al. | |
| 4,153,641 A | 5/1979 | Deichert et al. | |
| 4,156,066 A | 5/1979 | Gould | |
| 4,156,067 A | 5/1979 | Gould | |
| 4,166,255 A | 8/1979 | Graham | |
| 4,169,119 A | 9/1979 | Covington | |
| 4,182,822 A | 1/1980 | Chang | |
| 4,186,026 A | 1/1980 | Rotenberg et al. | |
| 4,189,546 A | 2/1980 | Deichert et al. | |
| 4,195,030 A | 3/1980 | Deichert et al. | |
| 4,197,266 A | 4/1980 | Clark et al. | |
| 4,198,131 A | 4/1980 | Birdsall et al. | |
| 4,208,362 A | 6/1980 | Deichert et al. | |
| 4,208,506 A | 6/1980 | Deichert et al. | |

(Continued)

FOREIGN PATENT DOCUMENTS

| EP | 0114894 A1 | 7/1983 |
|---|---|---|
| EP | 0108886 A2 | 9/1983 |

(Continued)

OTHER PUBLICATIONS

Plaintiff's Ciba Vision's Memorandum in Opposition to Defendant's Motion for Summary Judgment, May 31, 2002 with Exhibits 1–7.

Bausch & Lomb's Expert Reports, Jean M. Frechet, Jun. 24, 2002; Dr. Erwin A. Vogler, Jun. 24, 2002; Preliminary Report of William J. Benjamin, Jun. 24, 2002; Preliminary Report of Dr. William Daly, Jun. 24, 2002 and Nonpublicly Available Exhibits to Daly Report, Jun. 24, 2002.

(Continued)

Primary Examiner—Edward J. Cain
(74) Attorney, Agent, or Firm—Banner & Witcoff, Ltd.

(57) ABSTRACT

An ophthalmic lens suited for extended-wear periods of at least one day on the eye without a clinically significant amount of corneal swelling and without substantial wearer discomfort. The lens has a balance of oxygen permeability and ion or water permeability, with the ion or water permeability being sufficient to provide good on-eye movement, such that a good tear exchange occurs between the lens and the eye. A preferred lens is a copolymerization product of a oxyperm macromer and an ionoperm monomer. The invention encompasses extended wear contact lenses, which include a core having oxygen transmission and ion transmission pathways extending from the inner surface to the outer surface.

84 Claims, No Drawings

U.S. PATENT DOCUMENTS

| | | | |
|---|---|---|---|
| 4,214,014 A | * 7/1980 | Hofer | 427/40 |
| 4,217,038 A | 8/1980 | Letter et al. | |
| 4,225,631 A | 9/1980 | Berger et al. | |
| 4,228,269 A | 10/1980 | Loshaek et al. | |
| 4,229,273 A | 10/1980 | Wajs | |
| 4,242,483 A | 12/1980 | Novicky | |
| 4,245,069 A | 1/1981 | Covington | |
| 4,254,248 A | 3/1981 | Friends et al. | |
| 4,259,467 A | 3/1981 | Keogh et al. | |
| 4,260,725 A | 4/1981 | Keogh et al. | |
| 4,261,875 A | 4/1981 | LeBoeuf | |
| 4,276,402 A | 6/1981 | Chromecek et al. | |
| 4,277,595 A | 7/1981 | Deichert et al. | |
| 4,291,953 A | 9/1981 | Covington | |
| 4,294,974 A | 10/1981 | LeBoeuf | |
| 4,303,772 A | 12/1981 | Novicky | |
| 4,312,575 A | 1/1982 | Peyman et al. | |
| 4,322,517 A | 3/1982 | Deubzer et al. | |
| 4,327,203 A | 4/1982 | Deichert et al. | |
| 4,332,922 A | 6/1982 | Kossmehl et al. | |
| 4,341,889 A | 7/1982 | Deichert et al. | |
| 4,355,135 A | 10/1982 | January | |
| 4,355,147 A | 10/1982 | Deichert et al. | |
| 4,359,558 A | 11/1982 | Gould et al. | |
| 4,365,050 A | 12/1982 | Ivani | |
| 4,395,496 A | 7/1983 | Wittmann et al. | |
| RE31,406 E | 10/1983 | Gaylord | |
| 4,408,023 A | 10/1983 | Gould et al. | |
| 4,410,674 A | 10/1983 | Ivani | |
| 4,413,104 A | 11/1983 | Deubzer et al. | |
| 4,423,195 A | 12/1983 | Covington | |
| 4,424,305 A | 1/1984 | Gould et al. | |
| 4,436,887 A | 3/1984 | Chromecek et al. | |
| 4,439,583 A | 3/1984 | Gould et al. | |
| 4,439,584 A | 3/1984 | Gould et al. | |
| 4,439,585 A | 3/1984 | Gould et al. | |
| 4,440,918 A | 4/1984 | Rice et al. | |
| 4,447,562 A | 5/1984 | Ivani | |
| 4,454,295 A | 6/1984 | Wittmann et al. | |
| 4,454,309 A | 6/1984 | Gould et al. | |
| 4,463,149 A | 7/1984 | Ellis | |
| 4,478,981 A | 10/1984 | Arkles | |
| 4,486,577 A | 12/1984 | Mueller et al. | |
| 4,487,905 A | 12/1984 | Mitchell | |
| 4,495,361 A | 1/1985 | Friends et al. | |
| 4,496,535 A | 1/1985 | Gould et al. | |
| 4,500,676 A | 2/1985 | Balazs et al. | |
| 4,527,293 A | 7/1985 | Eckstein et al. | |
| 4,528,301 A | 7/1985 | Upchurch | |
| 4,543,398 A | 9/1985 | Bany et al. | |
| 4,546,123 A | 10/1985 | Schäfer et al. | |
| 4,550,139 A | 10/1985 | Arkles | |
| 4,555,372 A | 11/1985 | Kunzler et al. | |
| 4,563,565 A | 1/1986 | Kampfer et al. | |
| 4,576,850 A | 3/1986 | Martens | |
| 4,582,884 A | 4/1986 | Ratkowski | |
| 4,582,885 A | 4/1986 | Barber | |
| 4,602,074 A | 7/1986 | Mizutaki et al. | |
| 4,605,712 A | 8/1986 | Mueller et al. | |
| 4,616,045 A | 10/1986 | Upchurch | |
| 4,625,007 A | 11/1986 | Ellis et al. | |
| 4,626,292 A | 12/1986 | Sherman | |
| 4,632,844 A | 12/1986 | Yanagihara et al. | |
| 4,632,968 A | 12/1986 | Yokota et al. | |
| 4,649,184 A | 3/1987 | Yoshikawa et al. | |
| 4,649,185 A | 3/1987 | Takamizawa et al. | |
| 4,652,622 A | 3/1987 | Friends et al. | |
| 4,659,777 A | 4/1987 | Riffle et al. | |
| 4,661,573 A | 4/1987 | Ratkowski et al. | |
| 4,663,409 A | 5/1987 | Friends et al. | |
| 4,664,657 A | 5/1987 | Williamitis et al. | |
| 4,665,145 A | 5/1987 | Yokota et al. | |
| 4,666,249 A | 5/1987 | Bauman et al. | |
| 4,668,558 A | 5/1987 | Barber | |
| 4,687,816 A | * 8/1987 | Lin et al. | 525/279 |
| 4,696,974 A | 9/1987 | Sulc et al. | |
| 4,703,097 A | 10/1987 | Wingler et al. | |
| 4,711,943 A | 12/1987 | Harvey, III | |
| 4,727,172 A | 2/1988 | Yamamoto et al. | |
| 4,731,080 A | 3/1988 | Galin | |
| 4,732,715 A | 3/1988 | Bawa et al. | |
| 4,737,322 A | 4/1988 | Bruns et al. | |
| 4,737,558 A | 4/1988 | Falcetta et al. | |
| 4,740,533 A | 4/1988 | Su et al. | |
| 4,743,667 A | 5/1988 | Mizutani et al. | |
| 4,752,627 A | 6/1988 | Froix | |
| 4,769,431 A | 9/1988 | Ratkowski | |
| 4,780,488 A | 10/1988 | Su et al. | |
| 4,780,515 A | 10/1988 | Deichert | |
| 4,792,414 A | 12/1988 | Su et al. | |
| 4,803,254 A | 2/1989 | Dunks et al. | |
| 4,806,382 A | 2/1989 | Goldgerg et al. | |
| 4,810,764 A | 3/1989 | Friends et al. | |
| 4,818,801 A | 4/1989 | Rice et al. | |
| 4,826,936 A | 5/1989 | Eillis | |
| 4,829,137 A | 5/1989 | Stoyan | |
| 4,833,262 A | 5/1989 | Kunzler et al. | |
| 4,837,289 A | 6/1989 | Mueller et al. | |
| 4,840,796 A | 6/1989 | Sweet et al. | |
| 4,849,285 A | 7/1989 | Dillion | |
| 4,853,453 A | 8/1989 | Schafer et al. | |
| 4,857,606 A | 8/1989 | Su et al. | |
| 4,859,383 A | 8/1989 | Dillion | |
| 4,866,148 A | 9/1989 | Geyer et al. | |
| 4,871,785 A | 10/1989 | Froix | |
| 4,894,231 A | 1/1990 | Moreau et al. | |
| 4,910,277 A | 3/1990 | Bambury et al. | |
| 4,920,184 A | 4/1990 | Schafer et al. | |
| 4,923,906 A | 5/1990 | Mueller et al. | |
| 4,925,668 A | 5/1990 | Khan et al. | |
| 4,938,827 A | 7/1990 | Leach et al. | |
| 4,940,751 A | 7/1990 | Frances et al. | |
| 4,943,150 A | 7/1990 | Deichert et al. | |
| 4,943,460 A | 7/1990 | Markel et al. | |
| 4,948,485 A | 8/1990 | Wallsten et al. | |
| 4,948,855 A | 8/1990 | Novicky | |
| 4,948,907 A | 8/1990 | Fleischmann et al. | |
| 4,954,586 A | 9/1990 | Toyoshima et al. | |
| 4,954,587 A | 9/1990 | Mueller | |
| 4,961,954 A | 10/1990 | Goldbert et al. | |
| 4,962,178 A | 10/1990 | Harisiades | |
| 4,968,532 A | 11/1990 | Janssen et al. | |
| 4,977,229 A | 12/1990 | Culberson et al. | |
| 4,980,208 A | * 12/1990 | Sugiyama | 427/444 |
| 4,983,332 A | 1/1991 | Hahn et al. | |
| 4,983,702 A | 1/1991 | Mueller et al. | |
| 5,002,979 A | 3/1991 | Stoyan | |
| 5,006,622 A | 4/1991 | Kunzler et al. | |
| 5,008,115 A | 4/1991 | Lee et al. | |
| 5,010,141 A | 4/1991 | Mueller | |
| 5,011,275 A | 4/1991 | Mueller | |
| 5,013,808 A | 5/1991 | Piskoti | |
| 5,019,628 A | 5/1991 | Spinelli | |
| 5,023,305 A | 6/1991 | Onozuka et al. | |
| 5,032,658 A | 7/1991 | Baron et al. | |
| 5,034,461 A | * 7/1991 | Lai | 525/100 |
| 5,039,769 A | 8/1991 | Molock et al. | |
| 5,053,048 A | 10/1991 | Pinchik | |
| 5,057,578 A | 10/1991 | Spinelli | |
| 5,062,995 A | 11/1991 | Wu et al. | |
| 5,070,169 A | 12/1991 | Robertson et al. | |
| 5,070,170 A | 12/1991 | Robertson et al. | |
| 5,070,215 A | 12/1991 | Bambury et al. | |
| 5,073,583 A | 12/1991 | Broderick | |
| 5,074,877 A | 12/1991 | Nordan | |
| 5,077,335 A | 12/1991 | Schwabe et al. | |
| 5,079,878 A | 1/1992 | Druskis et al. | |
| 5,080,839 A | 1/1992 | Kindt-Larsen | |
| 5,080,924 A | 1/1992 | Kamel et al. | |
| 5,084,537 A | 1/1992 | Stoyan | |

| | | |
|---|---|---|
| 5,091,204 A | 2/1992 | Ratner et al. |
| 5,094,876 A | 3/1992 | Goldberg et al. |
| 5,098,618 A | 3/1992 | Zelez |
| 5,100,689 A | 3/1992 | Goldberg et al. |
| 5,104,213 A | 4/1992 | Wolfson |
| 5,106,930 A | 4/1992 | Gupta |
| 5,115,056 A | 5/1992 | Mueller et al. |
| 5,116,369 A | 5/1992 | Kushibiki et al. |
| 5,128,408 A | 7/1992 | Tanaka et al. |
| 5,128,434 A | 7/1992 | Lai |
| 5,135,297 A | 8/1992 | Valint, Jr. |
| 5,141,748 A | 8/1992 | Rizzo |
| 5,147,396 A | 9/1992 | Kageyama et al. |
| 5,154,861 A | 10/1992 | McBriety et al. |
| 5,157,093 A | 10/1992 | Harisiades et al. |
| 5,158,573 A | 10/1992 | Berg |
| 5,158,717 A * | 10/1992 | Lai ............................ 264/1.1 |
| 5,160,597 A | 11/1992 | Colapicchioni et al. |
| 5,162,396 A | 11/1992 | Hilty et al. |
| 5,162,469 A | 11/1992 | Chen |
| 5,166,298 A | 11/1992 | Friedmann et al. |
| 5,171,607 A | 12/1992 | Cumbo |
| 5,171,809 A | 12/1992 | Hilty et al. |
| 5,177,165 A | 1/1993 | Valint, Jr. et al. |
| 5,177,167 A | 1/1993 | Tone et al. |
| 5,196,493 A | 3/1993 | Gruber et al. |
| 5,219,965 A * | 6/1993 | Valint ......................... 526/245 |
| 5,236,969 A | 8/1993 | Kunzler et al. |
| 5,238,613 A | 8/1993 | Anderson |
| 5,260,000 A | 11/1993 | Nandu et al. |
| 5,260,001 A | 11/1993 | Nandu et al. |
| 5,264,161 A | 11/1993 | Druskis et al. |
| 5,270,418 A | 12/1993 | Kunzler et al. |
| 5,271,875 A | 12/1993 | Appelton et al. |
| 5,274,008 A | 12/1993 | Lai |
| 5,298,533 A | 3/1994 | Nandu et al. |
| 5,310,779 A | 5/1994 | Lai |
| 5,314,960 A | 5/1994 | Spinelli et al. |
| 5,321,108 A | 6/1994 | Kunzler et al. |
| 5,334,681 A * | 8/1994 | Mueller ...................... 526/243 |
| 5,336,797 A | 8/1994 | McGee et al. |
| 5,346,946 A | 9/1994 | Yokoyama et al. |
| 5,352,714 A | 10/1994 | Lai et al. |
| 5,357,013 A | 10/1994 | Bambury et al. |
| 5,358,995 A | 10/1994 | Lai et al. |
| 5,364,918 A | 11/1994 | Valint, Jr. et al. |
| 5,371,147 A | 12/1994 | Spinelli et al. |
| 5,374,662 A | 12/1994 | Lai et al. |
| 5,378,412 A | 1/1995 | Smith et al. |
| 5,387,632 A | 2/1995 | Lai et al. |
| 5,387,662 A | 2/1995 | Kunzler et al. |
| 5,387,663 A | 2/1995 | McGee et al. |
| 5,391,589 A * | 2/1995 | Kiguchi ...................... 523/106 |
| 5,420,324 A | 5/1995 | Lai et al. |
| 5,435,943 A | 7/1995 | Adams et al. |
| 5,449,729 A | 9/1995 | Lai et al. |
| 5,451,617 A | 9/1995 | Lai et al. |
| 5,451,651 A | 9/1995 | Lai |
| 5,453,467 A | 9/1995 | Bamford et al. |
| 5,456,864 A | 10/1995 | Wickes et al. |
| 5,466,147 A | 11/1995 | Appelton et al. |
| 5,486,579 A | 1/1996 | Lai et al. |
| 5,496,871 A | 3/1996 | Lai et al. |
| 5,512,205 A | 4/1996 | Lai |
| 5,525,691 A | 6/1996 | Valint, Jr. et al. |
| 5,534,605 A | 7/1996 | Bambury et al. |
| 5,539,016 A | 7/1996 | Kunzler et al. |
| 5,563,184 A | 10/1996 | McGee et al. |
| 5,610,252 A | 3/1997 | Bambury et al. |
| 5,629,360 A | 5/1997 | Askari et al. |
| 5,726,733 A | 3/1998 | Lai et al. |
| 5,849,811 A * | 12/1998 | Nicolson et al. ............ 523/106 |
| 5,760,100 A | 11/2000 | Nicolson et al. |
| 5,776,999 A | 11/2000 | Nicolson et al. |
| 5,789,461 A | 11/2000 | Nicolson et al. |
| 5,849,811 A | 11/2000 | Nicolson et al. |

FOREIGN PATENT DOCUMENTS

| | | |
|---|---|---|
| EP | 0184729 B1 | 11/1985 |
| EP | 0277771 A3 | 1/1988 |
| EP | 0 295 947 B1 | 6/1988 |
| EP | 0295947 A3 | 6/1988 |
| EP | 0170141 B1 | 7/1988 |
| EP | 0306756 A2 | 8/1988 |
| EP | 0306756 B1 | 8/1988 |
| EP | 0330616 A1 | 2/1989 |
| EP | 0395583 A2 | 4/1990 |
| EP | 90810308 | 4/1990 |
| EP | 0425436 A3 | 10/1990 |
| EP | 0461270 A1 | 12/1990 |
| EP | 0489185 A1 | 12/1990 |
| EP | 0439429 A2 | 1/1991 |
| EP | 0 443 005 | 4/1991 |
| EP | 0480238 A1 | 9/1991 |
| EP | 0497204 A2 | 1/1992 |
| EP | 0528664 A1 | 2/1993 |
| EP | 0584764 A1 | 8/1993 |
| EP | 0614921 A2 | 3/1994 |
| EP | 0620455 A2 | 4/1994 |
| EP | 0687550 A2 | 6/1994 |
| EP | 0643083 A1 | 9/1994 |
| EP | 0686491 A2 | 6/1995 |
| EP | 0735097 A1 | 3/1996 |
| EP | 0781777 A1 | 12/1996 |
| EP | 0782016 A2 | 12/1996 |
| JP | 6[1994]-122779 | 5/1994 |
| WO | WO90/09013 | 8/1990 |
| WO | WO92/07013 | 4/1992 |
| WO | WO 94/15980 | 7/1994 |
| WO | WO94/15980 | 7/1994 |
| WO | WO95/24187 | 9/1994 |
| WO | WO95/17689 | 6/1995 |
| WO | WO95/20476 | 8/1995 |

OTHER PUBLICATIONS

Bausch & Lomb's Incorporated's Reply Brief In Support of Its Motion For Summary Judgment, Jun. 20, 2002 with Exhibits A–I.

Defendant Bausch & Lomb Incorporated's Motion for Summary Judgment of Invalidity Pursuant to 35 U.S.C. § 112, ¶ 1., May 7, 2002 with Exhibits A–M.

Defendant Bausch & Lomb Incorporated's Memorandum in Support of its Motion for Summary Judgment of Invalidity Pursuant to 35 U.S.C. § 112, ¶ 1., May 7, 2002.

Trial vol. 1, *Wesley Jessen Corporation v. Bausch & Lomb, Inc.*, May 29, 2002; Trial vol. 2, May 30, 2002; Trial vol. 3, May 31, 2002; Trial vol. 4, Jun. 3, 2002; and Trial vol. 5, Jun. 4, 2002.

Expert Report of Robert L. Sheridan with Exhibits A, B and C.

Carmaels & Ransford, documents relating to opposition—Jun. 10, 2002.

Ciba's Surresponse in Opposition to B&L's Motion for Summary Judgment on Best Mode Grounds, Jul. 3, 2002 with Exhibit A, Deposition of Lynn Cook Winterton and Exhibit B, Deposition of Richard Baron.

United States Court of Appeals, Reply Brief of Appellant Bausch & Lomb Incorporated, dated Oct. 16. 2002.

United States District Court for the District of Delaware, Decision dated Jun. 26, 2002 on *Wesley Jessen Corporation v. Bausch & Lomb, Inc.*

United States Court of Appeals for the Federal Circuit, Brief of Appellant Bausch & Lomb Incorporated, dated Aug. 22, 2002.

United States Court of Appeals for the Federal Circuit, Brief of Appellee Wesley Jessen Corporation, dated Oct. 4, 2002.

Plaintiff's Ciba Vision's Memorandum in Opposition to Defendant's Motion for Summary Judgment, May 31, 2002 with Exhibits 1–7. (Note: This Information may be Subject to Protective Order—not Open to Public, Only by Examiner or Other Authorized Patent and Trademark Office Employee).

Bausch & Lomb's Expert Reports, Jean M. Frechet, Jun. 24, 2002; Dr. Erwin A. Vogler, Jun. 24, 2002; Preliminary Report of William J. Benjamin, Jun. 24, 2002. (Note: This Information may be Subject to Protective Order—not Open to Public, only by Examiner or other Authorized Patent and Trademark Office Employee).

Bausch & Lomb's Incorporated's Reply Brief In Support of Its Motion For Summary Judgment, Jun. 20, 2002 with Exhibits A–I. (Note: This Information may be Subject to Protective Order—Not Open to Public, Only by Examiner or Other Authorized Patent and Trademark Office Employee).

Defendant Bausch & Lomb Incorporated's Motion for Summary Judgment of Invalidity Pursuant to 35 U.S.C. § 112, ¶ 1., May 7, 2002 with Exhibits A–M. (Note: This Information may be Subject to Protective Order—Not Open to Public, Only by Examiner or Other Authorized Patent and Trademark Office Employee).

Defendant Bausch & Lomb Incorporated's Memorandum in Support of its Motion for Summary Judgment of Invalidity Pursuant to 35 U.S.C. § 112, ¶ 1., May 7, 2002. Note: This Information may be Subject to Protective Order—Not Open to Public, Only by Examiner or Other Authorized Patent and Trademark Office Employee).

Trial Volume 1, Wesley Jessen Corporation v. Bausch & Lomb, Inc., May 29, 2002; Trial Volume 2, May 30, 2002, Trial Volume 3, May 31, 2002, Trial Volume 4, Jun. 3, 2002; and Trial Volume 5, Jun. 4, 2002.

Expert Report of Robert L. Sheridan with Exhibits A, B and C. (Note: This Information may be Subject to Protective Order—not Open to Public, Only by Examiner or Other Authorized Patent and Trademark Office Employee).

Carmaels & Ransford, documents relating to opposition—Jun. 10, 2002.

Ciba's Surresponse in Opposition to B&L's Motion for Summary Judgment on Best Mode Grounds, Jul. 3, 2002 with Exhibit A, Deposition of Lynn Cook Winterton and Exhibit B, Deposition of Richard Baron. (Note: This Information may be Subject to Protective Order—not Open to Public, Only by Examiner or Other Authorized Patent and Trademark Office Employee).

Declaration of Yu–Chin Lai—Dec. 18, 2001.

Bausch & Lomb's Response to Ciba's Surreply Brief—Jan. 15, 2002.

Designated "Highlighted" Pages of Deposition of Yu–Chin–Lai, Nov. 17, 1999 (Note: This Information is Subject to a Protective Order—It is not Open to the Public, but Only to the Examiner or Other Authorized Patent and Trademark Office Employee).

R & D Clinical Report, with "Highlighted" Portions, Feb. 7, 1994 (Note: This Information is Subject to a Protective Order—It is not Open to the Public, but Only to the Examiner or Other Authorized Patent and Trademark Office Employee).

Designated "Highlighted" Pages of Deposition of Paul Nicolson, Nov. 10, (Note: This Information is Subject to a Protective Order—It is not Open to the Public, but Only to the Examiner or Other Authorized Patent and Trademark Office Employee).

Distribution with "Highlighted" Pages (Note: This Information is Subject to a Protective Order—It is not Open to the Public, but Only to the Examiner or Other Authorized Patent and Trademark Office Employee).

Bausch & Lomb Incorporated's Opposition to CIBA Corporation's Motion to Permit Certain Attorney's to have access to Information Under the Stipulated Protective Order (with Exhibits A–J) (Note: This Information is Subject to a Protective Order—It is not Open to the Public, but Only to the Examiner or Other Authorized Patent and Trademark Office Employee).

Defendant Bausch & Lomb Incorporated's Opposition to CIBA Corporation's Motion to Use Evidence from this case at the Reexamination Proceedings (with Exhibits A–J) (Note: This Information is Subject to a Protective Order—It is not Open to the Public, but Only to the Examiner or Other Authorized Patent and Trademark Office Employee).

An article in Macromolecular Engineering (1995) entitled "*Transparent Multiphasic Oxygen Permeable Hydrogels based on Silaxanic Statistical Copolymers*" by Robert et al, which was publicly available in Aug. 1995 in the United States (Exhibit G).

An article in Trends in Polymer Science entitled "*Silicone Hydrogels for Contact Lens Application*" by Jay F. Kunzler which was publicly available in Feb. 1996 in the United Kingdom (Exhibit H).

An article in the Contact Lens Association of Ophthalmologists Journal ("CLAO"), vol. 13, No. 1 (Jan. 1987) entitled "*Gas Permeable Hard Contact Lens Extended Wear: Ocular and Visual Responses to a 6–Month Period of Wear*" by Kenneth A. Polse et al., which was publicly available in Jan. 1987 in the United States of America (Exhibit I).

An article in the Contact Lens Association of Ophthalmologists Journal ("CLAO"), vol. 15, No. 2 (Apr. 1989) entitled "Paraperm® EW Lens for Extended Wear" by James E. Key et al., which was publicly available in Apr. 1989 in the United States of America (Exhibit J).

The publication of an article in Biomaterials, vol. 4 (Oct. 1983) entitled "*Gas–to–Liquid permeation in silicon–containing crosslinked, glassy copolymers of methyl methacrylate*" by Wu–Huang, Michael Yang, et al. which was publicly available in Oct. 1983 in the United States of America (Exhibit K).

The publication of an article in Macromolecular Symposia, vol. 98 entitled "*Recent Advances in the Design of Polymers for Contact Lenses*" by Gary D. Friends, et al., which was publicly available in Jul. 1995 in the United States of America (Exhibit L).

An article in The British Polymer Journal (Dec. 1976) entitled "*Polymers in Contact Lens Applications VI, The 'Dissolved' Oxygen Permeability of Hydrogels and the Design of Materials for use in Continuous–Wear Lenses*" by Chiong O. Ng et al., which was publicly available in Dec. 1976 in the United Kingdom (Exhibit M).

An article in the Journal of Japan Contact Lens Society, vol. 21, No. 5 (1979) entitled "*Physical Properties of High Water Combined Lens Materials, Compared with Rabbit's Cornea*" by Yujl Kosaka et al,. which was publicly available in 1979 in Japan (Exhibit N).

The *Medical Device Approval Letter*, vol. IV, No. 1, which was publicly available on line through a number of databases including DIALOG and LEXIS in Jan. 1995 (Exhibit O).

The *Medical Devices, The Diagnostics & Instrumentation Report—"The Grey Sheet"*, vol. 21, No. 4, dated Jan. 23, 1995 which was publicly available on line through a number of databases including DIALOG and LEXIS in about Jan. 1995 (Exhibit P).

The B&L US 510(k) application filed with the U.S. Food and Drug Administration ("USFDA") for the Premier 90 (Balafilicon A) contact lens which application was publicly available from the USFDA from Jan. 1995 (Exhibit Q).

*CIBA Vision Corporation, a Delaware corporation vs. Bausch & Lomb Incorporated, a New York Corporation*—Counter Claims—United States District Court for the Northern District of Georgia (Gainesville)—pp. 22–28 with Exhibit F—Apr. 19, 1999.

*CIBA Vision Corporation, a Delaware corporation vs. Bausch & Lomb Incorporated, a New York Corporation*—Memorandum in Opposition to CIBA's Motion for a Temporary Restraining Order and a Preliminary Injunction—United States District Court for the Northern District of Georgia (Gainesville) pp. 2–17 with Exhibits A–F and J.

In the Federal Court of Australia Victoria District Registry—Defence and Cross–Claim—No. V81 of 2000—Jun. 2, 2000.

Releasable 510(k) No. K972454—Aug. 8, 1997—Lenses, Soft Contact, Daily Wear.

Releasable 510(k) No. K944895—Dec. 8, 1994—Contact Lenses.

Letter from Mr. Edward W. Remus to Michael O. Sutton, Esq.—Apr. 4, 2000–RE: *CIBA Vision Corporation v. Bausch & Lomb Incorporated*.

Letter from Mr. Edward W. Remus of McAndrews, Held & Malloy, Ltd. to Kenneth L. Cage, Esq. at McDermott, Will & Emery—RE: *CIBA Vision Corporation v. Bausch & Lomb Incorporated*—Jun. 5, 2000.

Letter from Richard T. McCaulley Jr. of McAndrews, Held & Malloy, Ltd., to Michael O. Sutton at Sidley & Austin—RE: *CIBA Vision Corp v. Bausch & Lomb Inc.* Civil Action No. 99–0034–WCO—Jun. 23, 2000.

Letter from Kenneth L. Cage of McDermott, Will & Emery to Edward W. Remus at AcAndrews, Held & Molloy, LTD.—RE: *CIBA Vision Corporation v. Bausch & Lomb Incorporated*—May 25, 2000.

Letter from Kenneth L. Cage of McDermott, Will & Emery to Colleague—RE: *CIBA Vision Corporation v. Bausch and Lomb, Incorporated* U.S. Patent Reexamination Proceedings U.S. Patent Nos. 5,760,100: 5,849,811: 5,789,461; and 5,776,999.

Letter from Carol Kirby of the University of New South Wales to Mr. R. Hearhard at CIBA Vision Corporation—Jul. 7, 2000—RE: Rule 56 Inquiry—UNSW CCLRU.

Letter from Michael O. Sutton of Sidley & Austin to Kenneth L. Cage of McDermott, Will & Emery and to Richard Gearhart at CIBA Vision Corp.—Jul. 12, 2000—RE: *CIBA Vision Corporation v. Bausch & Lomb Incorporated* (16008/0010).

Letter from Michael O. Sutton to Edward W. Remus—Dec. 10, 1999.

Letter from Michael O. Sutton to Edward W. Remus—Dec. 14, 1999.

Letter from Edward W. Remus to Michael O. Sutton—Dec. 17, 1999.

Letter from Michael O. Sutton to Edward W. Remus—Dec. 22, 1999.

Letter from Edward W. Remus to Michael O. Sutton—Jan. 3, 2000.

Letter from Michael O. Sutton to Edward W. Remus—Jan. 4, 2000.

Letter from Edward W. Remus to Michael O. Sutton—Jan. 6, 2000.

Letter from Michael O. Sutton to Edward W. Remus—Jan. 12, 2000.

Letter from Russell Wheatley to Edward W. Remus—Jan. 31, 2000.

Letter from Edward W. Remus to Michael O. Sutton—Feb. 2, 2000.

Letter from Edward W. Remus to Michael O. Sutton—Feb. 7, 2000.

Letter from Michael O. Sutton to Edward W. Remus—Feb. 10, 2000.

Letter from Edward W. Remus to Michael O. Sutton—Feb. 18, 2000.

Letter from Michael O. Sutton to Edward W. Remus—Mar. 23, 2000.

Letter from Edward W. Remus to Michael O. Sutton—Mar. 30, 2000.

Letter from Michael O. Sutton to Edward W. Remus—Apr. 3, 2000.

Letter from Michael O. Sutton to Edward W. Remus—Jun. 19, 2000.

Letter from Edward W. Remus to Michael O. Sutton—Jun. 30, 2000.

Weissman et al. "Cancellation of the Boundary and Edge Effects by Choice of Lens Thickness during Oxygen Permeability Measurement of Contact Lens", Optometry & Vision Science, vol. 66, No. 5, pp. 264–268, (1989).

Hamano et al., "A study of the Complications Induced by Conventional and Disposable Contact Lenses", The CLAO Journal, vol. 20, pp. 103–110, (1994).

Schein et al., "The Impact of Overnight Wear on the Risk of Contact Lens–Associated Ulcerative Keratitis", Arch. Ophthalmol, vol. 112, pp. 186–190, 91994).

Nilsson et al., "The Hospitalized Cases of Contact Lens Induced Keratitis in Sweden and their Relation to Lens Type and Wear Schedule; Results of a Three–Year Retrospective Study", The CLAO Journal, vol. 20, pp. 97–101, (1994).

Goyal et al., "Corneal Ulcers in Patients with Disposable Extended–Wear Contact Lenses", Ann. Ophthalmol—Glaucoma, vol. 26, pp. 194–199, (1994).

Schein et al., "The Relative Risk of Ulcerative Keratitis Among Users of Daily–Wear and Extended–Wear Soft Contact Lenses", The New England Journal of Medicine, vol. 321, pp. 773–776, (1989).

Solomon et al., "Testing Hypotheses for Risk Factors for Contact Lens–Associate Infectious Keratitis in an Animal Model", The CLAO Journal, vol. 20, pp. 109–113, (1994).

Poggio et al., "Complications and Symptons in Disposable Extended Wear Lenses Compared with Conventional Sofy Daily Wear and Soft Extended Wear Lenses", The CLAO Journal, vol. 19, pp. 31–39, (1993).

Poggio et al., "The Incidence of Ulcerative Keratitis Among Users of Daily–Wear and Extended–Wear Soft Contact Lenses", The New England Journal of Medicine, vol. 321, pp. 779–783, (1989).

McRae et al., "Corneal Ulcer and Adverse Reaction Rates in Premarket Contact Lens Studies", American Journal of Ophthalmology, vol. 111, pp. 457–465, (1991).

Grant et al., "Extended Wear of Hydrogel Lenses", Problems in Optometry, vol. 2, pp. 599–622, (1990).

Brennan et al., "Extended Wear in Perspective", Optometry and Vision Science, vol. 74, 609–623, (1997).

Winterton et al., "Coulometric Method for Measuring Oxygen Flux and Dk of Contact Lenses and Lens Materials", vol. 14, No. 11, 1987, pp. 441–449, (1987).

Winterton et al., "Coulometrically Determined Oxygen Flux and Resultant Dk of Commercially Available Contact Lenses", vol. 15, pp. 117–123, (1988).

Holden et al., "The Dk Project: An Interlaboratory Comparison of Dk/L Measurements", Optometry and Vision Science, vol. 67, pp. 476–481, (1989).

Winterton et al., "Coulometric Method for Measuring Oxygen Flux and Dk of Contact Lenses and Lens Materials", The Cornea: Transactions of The World Congress on The Cornea III, Raven Press, Chapter 47, pp. 273–280, (1988).

Alvord et al., "Oxygen Permeability of a New Type of High Dk Soft Contact Lens Material", Optometry and Vision Science, vol. 75, pp. 30–36, (1998).

Holden et al., "Critical Oxygen Levels to Avoid Corneal Edema for Daily and Extended Wear Contact Lenses", Investigative Opthalmology & Visual Science, vol. 25, pp. 2–8, (1983).

Domschke et al., "Morphology Requirements For On–Eye Mobility of Soft Oxygen Permeable Contact Lenses", Business and Technology Innovation, Ciba Vision.

Kirk Othmer Encyclopedia of Chemical Technology (chapter on contact lenses), pp. 720–741.

Edelhauser et al. "Oxygen, calcium, lactate, chloride, and sodium permeability of soft contact lenses" in Gasset et al. "Soft Contact Lenses"; The C.V. Mosby Co., (1972) Saint Louis, pp. 37–43.

U.S. Prosecution History of U.S. Pat. No. 5,034,461.

U.S. Prosecution History of U.S. Pat. No. 5,451,617.

U.S. Prosecution History of U.S. Pat. No. 5,486,579.

Mandell, R., *Contact Lens Practice, Fourth Edition*, Springfield, IL, pp. 520–521 (1988).

Lai, Yu–Chin, "The Role of Bulky Polysiloxanylalkyl Methacrylates in Oxygen Permeable Hydrogel Materials," ACS Workshop–Hyphenated Methods In Polymer Spectroscopy, *Polymeric Materials Science and Engineering*, vol. 69, Fall Meeting, Chicago, IL, pp. 228–231 (1993).

Fatt, I., et al., "Measuring Oxygen Permeablilty of Gas Permeable Hard and Hydrogel Lenses and Flat Samples in Air," vol. 14, No. 10 (Oct. 1987) pp. 389–401 (Oct. 1987).

Lai, Yu, et al., "Surface Wettability Enhancement of Silicone Hydrogel Lenses by Processing with Polar Plastic Molds," *J. of Biomed. Mat. Res.*, vol. 35:3, pp. 349–356 (1997).

Lai, Yu, et al., "Synthesis and Characterization of α,ω–Bis(4–hydroxybutyl) Polydimethylesiloxane," *Polymer Prerints*, 35:2, American Chemical Society (Aug. 1994).

Memorandum in Support of CIBA's Motion to Use Evidence from this Case in the Reexamination Proceedings ("CIBA Motion") (with Exhibits 1–8) (Note: This Information is Subject to a Protective Order—It is not Open to the Public, but Only to the Examiner or Other Authorized Patent and Trademark Office Employee).

Reply Brief in Support of CIBA VISION Corporation's Motion to use Evidence from this Case in the Reexamination Proceedings ("CIBA Reply") (with Exhibits 1–7) (Note: This Information is Subject to a Protective Order—It is not Open to the Public, but Only to the Examiner or Other Authorized Patent and Trademark Office Employee).

The Journal of Clinical Pharmacology and Therapeutics, vol. 58, No. 5, p. 604. Nov. 1995 edition, which contained the structural formula for Balafilicon A and which was publicly available in Nov. 1995 in the United States (Exhibit A).

The publication in Chemistry and Industry of an article by Kunzler entitled "*Contact Lens Materials*", Aug. 21, 1995, pp. 651–655 and which was publicly available from Oct. 19, 1995 at the University of New South Wales Library (Exhibit B).

The publication of an article in the Journal of Applied Polymer Science, vol. 55 (1995), pp. 611–619, by Kunzler et al. entitled "*Hydrogels Based on Hydrophilic Side–Chain Siloxanes*", and which was publicly available from Feb. 21, 1995 at the University of New South Wales Library (Exhibit C).

An article in World Plastics and Rubber Technology (1992), pp. 23–29, entitled "*Clear Vision for the Future*" by Lai et al. and which was publicly available from Nov. 16, 1992 at the State Library of New South Wales (Exhibit D).

An article in the Journal of Applied Polymer Science, vol. 56 (1995) entitles "*Role of Bulky Polysilaxanylalkyl Methocrylates in Oxygen–Permeable Hydrogen Materials*" by Lai et al. and which was publicly available in Apr. 1995 in the United States (Exhibit E).

An article in the Journal of Applied Polymer Science, vol. 56 (1995) entitled "*Novel Polyurethane—Silicone Hydrogels*" by Lai which was publicly available in Apr. 1995 in the United States (Exhibit F).

Hung, William, Preparation and Testing Silicone Containing Hydrogel Lenses as Described in U.S. Pat. No. 52160000, submitted to EP patent office regarding EP Patent No. 0819258, Apr. 1, 2004.

Breuer & Muller, Grounds of Appeal, in EP Patent application 96 906 116.5–2217, dated Apr. 1, 2004.

Fisher, Adrian John, Submissions of Opponent II in response to the Proprietors' Appeal, dated Aug. 24, 2004.

Winterton, Lynn C., et al., Coulometric Method for Measuring Oxygen Flux and Dk of Contact Lenses and Lens Materials, ICLC, vol. 14, No. 11, Nov. 1987, pp. 441–450.

Declaration of William J. Benjamin, Professor of Optometry and Physiological Optic University of Alabama at Birmingham, Aug. 24, 2004.

Package insert, Focus Night & Day Soft Contact Lenses for Extended Wear, print date: Sep. 2001.

Order of J. Merkel in Federal Court of Australia, Victoria District Registry, Novartis AG v. Bausch & Lomb (Australia) Pty. Ltd [2004] FCA 835, dated Aug. 24, 2004.

Criticism of the Experimental Report provided by Dr. William M. Hung,, submitted to EP patent office regarding EP Patent No. 0819258, Aug. 24, 2004.

Heidelberg, Alfred Huthig Verlag; Praktikum Der Makromolekularen Organischen Chemie, 1996. (Translation of relevant section included).

EP Patent application No. 90810308.8; Answer to EPO concerning Office Action, dated Mar. 30, 1994. (Translation of relevant section included).

*Ciba Vision Corporation et al. v. Bausch & Lomb Incorporated*, Plaintiff CIBA Vision Corporation's Post–Trail Proposed Findings of Fact and Conclusions of Law, United States District Court for the Northern District of Georgia (Gainesville), Civil Action File No. 2:99–0034–RWS, May 7, 2004, pp. 1–197.

*Ciba Vision Corporation et al. v. Bausch & Lomb Incorporated*, Bausch & Lomb's Proposed Findings of Fact and Conclusions of Law, United States District Court for the Northern District of Georgia (Gainesville), Civil Action File No. 2:99–0034–RWS, May 5, 2004, pp. 1–242.

*CIBA Vision Corporation et al. v. Bausch & Lomb, Inc.*, Consent Decree and Order of Dismissal with Prejudice, United States District Court for the Northern District of Georgia, Gainesville Division, Civil Action No. 2:99–0034–RWS, Jul. 23, 2004.

*Novartis AG v. Bausch & Lomb (Australia) Pty Ltd [2004] FCA 835*, Consent Order, Federal Court of Australia, Victoria District Registry, Aug. 24, 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 1–33, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 34–67, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 68–138, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 141–274, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 276–422, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 423–667, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 675–782, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 787 B, C & D, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 789–844, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 846–941, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 944–1015, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 1016–1081, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 1082–1132, Apr. 2004.

*CIBA Vision Corporation et al. v. Bausch & Lomb, Inc.*, Trial Before the Honorable Richard W. Story, United States District Court Judge for the Northern District of Georgia, Atlanta Division, Bausch & Lomb's Admitted Trial Exhibits 1134–1188, Apr. 2004.

*CIBA Vision Corporation et al. v. Bausch & Lomb, Inc.*, Trial Before the Honorable Richard W. Story, United States District Court Judge for the Northern District of Georgia, Atlanta Division, CIBA's Admitted Trial Exhibits 1–35, Apr. 2004.

*CIBA Vision Corporation et al. v. Bausch & Lomb, Inc.*, Trial Before the Honorable Richard W. Story, United States District Court Judge for the Northern District of Georgia, Atlanta Division, CIBA's Admitted Trial Exhibits 36–93, Apr. 2004.

*CIBA Vision Corporation et al. v. Bausch & Lomb, Inc.*, Trial Before the Honorable Richard W. Story, United States District Court Judge for the Northern District of Georgia, Atlanta Division, CIBA's Admitted Trial Exhibit 94, Apr. 2004.

*CIBA Vision Corporation et al. v. Bausch & Lomb, Inc.*, Trial Before the Honorable Richard W. Story, United States District Court Judge for the Northern District of Georgia, Atlanta Division, CIBA's Admitted Trial Exhibits 95–183, Apr. 2004.

*CIBA Vision Corporation et al. v. Bausch & Lomb, Inc.*, Trial Before the Honorable Richard W. Story, United States District Court Judge for the Northern District of Georgia, Atlanta Division, CIBA's Admitted Trial Exhibits 184–332, Apr. 2004.

*CIBA Vision Corporation et al. v. Bausch & Lomb, Inc.*, Trial Before the Honorable Richard W. Story, United States District Court Judge for the Northern District of Georgia, Atlanta Division, CIBA's Admitted Trial Exhibits 353–567, Apr. 2004.

*CIBA Vision Corporation et al. v. Bausch & Lomb, Inc.*, Trial Before the Honorable Richard W. Story, United States District Court Judge for the Northern District of Georgia, Atlanta Division, CIBA's Admitted Trial Exhibits 601–619, Apr. 2004.

CIBA Vision Corporation et al. v. Bausch & Lomb, Inc., Trial Before the Honorable Richard W. Story, United States District Court Judge for the Northern District of Georgia, Atlanta Division, CIBA's Admitted Trial Exhibit 620, Apr. 2004.

CIBA Vision Corporation et al. v. Bausch & Lomb, Inc., Trial Before the Honorable Richard W. Story, United States District Court Judge for the Northern District of Georgia, Atlanta Division, CIBA's Admitted Trial Exhibits 621–640, Apr. 2004.

CIBA Vision Corporation et al. v. Bausch & Lomb, Inc., Trial Before the Honorable Richard W. Story, United States District Court Judge for the Northern District of Georgia, Atlanta Division, CIBA's Admitted Demonstrative Trial Exhibits 100–114, Apr. 2004.

CIBA Vision Corporation et al. v. Bausch & Lomb, Inc., Trial Before the Honorable Richard W. Story, United States District Court Judge for the Northern District of Georgia, Atlanta Division, Bausch & Lomb's Admitted Demonstrative Trial Exhibits 27–82, Apr. 2004.

CIBA Vision Corporation et al. v. Bausch & Lomb, Inc., Trial Before the Honorable Richard W. Story, United States District Court Judge for the Northern District of Georgia, Atlanta Division, Bausch & Lomb's Admitted Demonstrative Trial Exhibit 83, Apr. 2004.

CIBA Vision Corporation v. Bausch & Lomb, Inc., Ciba Vision "See 3" Tape #01 & #02 BITC CibaVision Jun. 30, 1993, CV51 002700.

CIBA Vision Corporation v. Bausch & Lomb, Inc., Ciba Vision "See 3" Tape #03 & #04 BITC CibaVision Jun. 30, 1993, CV51 002701.

CIBA Vision Corporation v. Bausch & Lomb, Inc., Ciba Vision "See 3" Tape #05 & #06 BITC CibaVision Jun. 30, 1993, CV51 002702.

CIBA Vision Corporation v. Bausch & Lomb, Inc., Ciba Vision "See 3" Tape #07 & #08 BITC CibaVision Jun. 30, 1993, CV51 002703.

CIBA Vision Corporation v. Bausch & Lomb, Inc., Ciba Vision "See 3" Tape #09 & #10 BITC CibaVision Jun. 30, 1993, CV51 002704.

CIBA Vision Corporation v. Bausch & Lomb, Inc., Ciba Vision "See 3" Tape #11 & #12 BITC CibaVision Jun. 30, 1993, CV51 002705.

CIBA Vision Corporation v. Bausch & Lomb, Inc., Ciba Vision "See 3" Tape #13 & #14 BITC CibaVision Jun. 30, 1993, CV51 002707.

CIBA Vision Corporation v. Bausch & Lomb, Inc., Ciba Vision "See 3" Tape #15 & #16 BITC CibaVision Jun. 30, 1993, CV51 002709.

CIBA Vision Corporation v. Bausch & Lomb, Inc., Ciba Vision "See 3" Tape #17 & #18 BITC CibaVision Jun. 30, 1993, CV51 002710.

CIBA Vision Corporation v. Bausch & Lomb, Inc., Ciba Vision "See 3" Tape #19 & #20 BITC CibaVision Jun. 30, 1993, CV51 002711.

CIBA Vision Corporation v. Bausch & Lomb, Inc., Ciba Vision "See 3" Tape #21 & #22 BITC CibaVision Jun. 30, 1993, CV51 002712.

CIBA Vision Corporation v. Bausch & Lomb, Inc., Ciba Vision "See 3" Tape #23 & #24 BITC CibaVision Jun. 30, 1993, CV51 002713.

CIBA Vision Corporation v. Bausch & Lomb, Inc., Ciba Vision "See 3" Tape #25 & #26 BITC CibaVision Jun. 30, 1993, CV51 002708.

CIBA Vision Corporation v. Bausch & Lomb, Inc., Ciba Vision "See 3" Tape #27 & #28 BITC CibaVision Jun. 30, 1993, CV51 002706.

CIBA Vision Corporation v. Bausch & Lomb, Inc., Ciba Vision "See 3" Tape #29 RP Golf "Awards–Tape" CibaVision Jun. 30, 1993, CV51 002714.

CIBA Vision Corporation v. Bausch & Lomb, Inc., Tape, 1. See3 Z–Por/Dextran Jun. 10, 1995 Time—1:50 2. See3 Dispensing Study Jun. 10, 1995 Infiltrates—Mcov/Raus Time 2:00, CV51 002531.

CIBA Vision Corporation v. Bausch & Lomb, Inc., Tape, Extended Wear Brian Holden Ph.D, Sep. 16, 1992, Erba, Italy, CV51 002536.

CIBA Vision Corporation v. Bausch & Lomb, Inc., Ciba Vision/CRU/CECERT Research Collaboration Meeting, Sep. 16–20, 1992, Erba, Italy Tape 1 of 4 Time: 6 Hours, CV51 002532.

CIBA Vision Corporation v. Bausch & Lomb, Inc., Ciba Vision/CRU/CECERT Research Collaboration Meeting, Sep. 16–20, 1992, Erba, Italy Tape 2 of 4 Time: 6 Hours, CV51 002533.

CIBA Vision Corporation v. Bausch & Lomb, Inc., Ciba Vision/CRU/CECERT Research Collaboration Meeting, Sep. 16–20, 1992, Erba, Italy Tape 3 of 4 Time: 6 Hours, CV51 002534.

CIBA Vision Corporation v. Bausch & Lomb, Inc., Ciba Vision/CRU/CECERT Research Collaboration Meeting, Sep. 16–20, 1992, Erba, Italy Tape 4 of 4 Time: 6 Hours, CV51 002535.

Spark and Cannon, Transcript of Proceedings, Merkel J., Federal Court of Australia, Hearing & Motion, Novartis AG and Another and Bausch and Lomb (Australia) Pty Ltd., Oct. 7, 2003, (pp. P–1–P–76).

Spark and Cannon, Transcript of Proceedings, Merkel J., Federal Court of Australia, Hearing & Motion, Novartis AG and Another and Bausch and Lomb (Australia) Pty Ltd., Oct. 8, 2003, (pp. P–77–P–153).

Spark and Cannon, Transcript of Proceedings, Merkel J., Federal Court of Australia, Hearing & Motion, Novartis AG and Another and Bausch and Lomb (Australia) Pty Ltd., Hearing & Motion, Novartis AG and Another and Bausch and Lomb (Australia) Pty Ltd. Oct. 9, 2003, (pp. P–154–P–224).

Spark and Cannon, Transcript of Proceedings, Merkel J., Federal Court of Australia, Hearing & Motion, Novartis AG and Another and Bausch and Lomb (Australia) Pty Ltd., Oct. 10, 2003, (pp. P–225–P–294).

Spark and Cannon, Transcript of Proceedings, Merkel J., Federal Court of Australia, Hearing & Motion, Novartis AG and Another and Bausch and Lomb (Australia) Pty Ltd., Oct. 13, 2003, (pp. P–295–P–359).

Spark and Cannon, Transcript of Proceedings, Merkel J., Federal Court of Australia, Hearing & Motion, Novartis AG and Another and Bausch and Lomb (Australia) Pty Ltd., Oct. 14, 2003, (pp. P–360–P–422).

Spark and Cannon, Transcript of Proceedings, Merkel J., Federal Court of Australia, Hearing & Motion, Novartis AG and Another and Bausch and Lomb (Australia) Pty Ltd., Oct. 15, 2003, (pp. P–422–P–484).

Spark and Cannon, Transcript of Proceedings, Merkel J., Federal Court of Australia, Hearing & Motion, Novartis AG and Another and Bausch and Lomb (Australia) Pty Ltd., Oct. 16, 2003, (pp. P–485–P–563).

Spark and Cannon, Transcript of Proceedings, Merkel J., Federal Court of Australia, Hearing & Motion, Novartis AG and Another and Bausch and Lomb (Australia) Pty Ltd., Oct. 17, 2003, (pp. P–564–P–644).

Spark and Cannon, Transcript of Proceedings, Merkel J., Federal Court of Australia, Hearing & Motion, Novartis AG and Another and Bausch and Lomb (Australia) Pty Ltd., Oct. 20, 2003, (pp. P–645–P–679).

Spark and Cannon, Transcript of Proceedings, Merkel J., Federal Court of Australia, Hearing & Motion, Novartis AG and Another and Bausch and Lomb (Australia) Pty Ltd., Oct. 21, 2003, (pp. P–679–P–750), (pp. P1–P5).

Spark and Cannon, Transcript of Proceedings, Merkel J., Federal Court of Australia, Hearing & Motion, Novartis AG and Another and Bausch and Lomb (Australia) Pty Ltd., Oct. 22, 2003, (pp. P–751–P–822).

Spark and Cannon, Transcript of Proceedings, Merkel J., Federal Court of Australia, Hearing & Motion, Novartis AG and Another and Bausch and Lomb (Australia) Pty Ltd., Oct. 23, 2003, (pp. P–823–895).

Spark and Cannon, Transcript of Proceedings, Merkel J., Federal Court of Australia, Hearing & Motion, Novartis AG and Another and Bausch and Lomb (Australia) Pty Ltd., Oct. 24, 2003, (pp. P–896–968).

Order ("construction of the patent claims")—U.S. Court for the Northern District of Georgia Gainesville Division, Civil Action 2:99–CV–0034–RWS, dated Mar. 14, 2003.

*CIBA Vision Corporation v. Bausch & Lomb, Inc.*, Transcript of Trail Before the Honorable Robert W. Story, United State District Court Judge for the Northern District of Georgia, Atlanta Division, Vol. I, pp. 1–195, Mar. 15, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. II, pp. 196–406, Mar. 16, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. III, pp. 407–596, Mar. 17, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. IV, pp. 599–809, Mar. 19, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. V, pp. 810–1039, Mar. 22, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. VI, pp. 1040–1251, Mar. 23, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. VII, pp. 1252–1423, Mar. 24, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. VIII, pp. 1424–1577, Mar. 26, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. IX, pp. 1578–1781, Mar. 29, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. X, pp. 1782–1999, Mar. 30, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XI, pp. 2000–2200, Mar. 31, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XII, pp. 2201–2404, Apr. 1, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XIII, pp. 2405–2548, Apr. 2, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XIV, pp. 2549–2769, Apr. 13, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XV, pp. 2770–2989, Apr. 14, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XVI, pp. 2990–3204, Apr. 19, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XVII, pp. 3205–3432, Apr. 20, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XVIII, pp. 3433–3626, Apr. 21, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XIX, pp. 3627–3865, Apr. 22, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XX, pp. 3866–4072, Apr. 23, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XXI, pp. 4073–4303, Apr. 26, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XXII, pp. 4304–4319, Apr. 27, 2004.

*CIBA Vision Corporation v. Bausch & Lomb, Inc.*, Transcript of Trail Before the Honorable Robert W. Story, United State District Court Judge for the Northern District of Georgia, Atlanta Division, Vol. XXIII, pp. 4320–4456, Apr. 28, 2004.

*Opposition of European Patent No. 0819258, Novartis AG, et al.* by Johnson & Johnson Vision Care, Inc., Jun. 10, 2002.

*Novartis AG., Bausch & Lomb Inc., Johnson & Johnson Vision Care, Inc.*, European Patent Office, Minutes of the Oral Proceedings before the Opposition Division, Sep. 17, 2003.

*Johnson & Johnson Pacific Pty Limited v Novartis AG et al.*, In the Federal Court of Australia New South Wales District Registry, APPLICATION to revoke Australian Patent No. 704749, pp. 1–3, Sep. 11, 2003.

*Johnson & Johnson Pacific Pty Limited v Novartis AG et al.*, In the Federal Court of Australia New South Wales District Registry, Particulars of Invalidity, pp. 1–10, Sep. 11, 2003.

*Johnson & Johnson Pacific Pty Limited v Novartis AG et al.*, In the Federal Court of Australia New South Wales District Registry, Statement of Claim, pp. 1–2, Sep. 11, 2003.

*Johnson & Johnson (New Zealand) Limited v. Novartis AG et al.* In the High Court of New Zealand Wellington Registry, Respondents' Reply to the Applicant's Particulars of Objection as to Validity of New Zealand Letters Patent No. 304321, pp. 1–10, Jan. 23, 2004.

*Johnson & Johnson (New Zealand) Limited v. Novartis AG et al.* In the High Court of New Zealand Wellington Registry, Respondents' Reply to the Applicant's Particulars of Objection as to Validity of New Zealand Letters Patent No. 334977, pp. 1–9, Jan. 23, 2004.

*Johnson & Johnson (New Zealand) Limited v. Novartis AG et al.* In the High Court of New Zealand Wellington Registry, Notice of Application by Applicant for Directions Regarding the Proceeding, pp. 1–2, Oct. 28, 2003.

*Johnson & Johnson (New Zealand) Limited v. Novartis AG et al.* In the High Court of New Zealand Wellington Registry, Particulars of Objection as to Validity of New Zealand Letters Patent No. 334977, pp. 1–10, Oct. 28, 2003.

*Johnson & Johnson (New Zealand) Limited v. Novartis AG et al.* In the High Court of New Zealand Wellington Registry, Particulars of Objection as to Validity of New Zealand Letters Patent No. 304321, pp. 1–10, Oct. 28, 2003.

*Johnson & Johnson (New Zealand) Limited v. Novartis AG et al.* In the High Court of New Zealand Wellington Registry, Originating Application for Revocation of New Zealand Letters Patent Nos. 304321 and 334977, pp. 1–3, Oct. 28, 2003.

Bausch & Lomb's 1994 Annual Report p. 14.

George L. Grobe III, et al., Surface Characterization of an Oxidized Silicone Hydrogel, 1994, pp. 43–47.

Surfaces in BioMaterials '94, Symposium Notebook, Sep. 7–10, 1994, Scottdale, Arizona.

*Novartis AG et al. v. Bausch & Lomb (Australia) Pty. Ltd. et al.*, In the Federal Court of Australia Victoria District Registry, Bausch & Lomb's Supplementary Submission Concerning the Morphology of the Purevision Product, No. V81 of 2000, pp. 1–7, Dec. 17, 2003.

*Novartis AG et al. v. Bausch & Lomb (Australia) Pty. Ltd. et al.*, In the Federal Court of Australia Victoria District Registry, Respondent/Cross–Claimants' Submissions in Opposition to Amendment, No. V81 of 2000, pp. 1–19, Aug. 22, 2003.

*Novartis AG et al. v. Bausch & Lomb (Australia) Pty. Ltd. et al.*, In the Federal Court of Australia New South Wales District Registry, Bausch & Lomb's Submissions in Answer, No. V81 of 2000, pp. 1–29, Dec. 5, 2003.

*Novartis AG et al. v. Bausch & Lomb (Australia) Pty. Ltd. et al.*, In the Federal Court of Australia New South Wales District Registry, Bausch & Lomb's Response to the Applicants' Supplementary Closing Submissions, No. V81 of 2000, pp. 1–22, Dec. 5, 2003.

*Novartis AG et al. v. Bausch & Lomb (Australia) Pty. Ltd. et al.*, In the Federal Court of Australia Victoria District Registry, Statement of Grounds in Support of Amendment, No. V81 of 2000, pp. 1–4, Jun. 6, 2003.

*Novartis AG et al. v. Bausch & Lomb (Australia) Pty. Ltd. et al.*, In the Federal Court of Australia Victoria District Registry, Respondent/Cross–Claimants' Grounds of Opposition to Amendment, No. V81 of 2000, pp. 1–8, Jul. 4, 2003.

*Novartis AG et al. v. Bausch & Lomb (Australia) Pty. Ltd. et al.*, In the Federal Court of Australia Victoria District Registry, Bausch & Lomb's Contention of Fact and Law, No. V81 of 2000, pp. 1–29, Sep. 29, 2003.

*Novartis AG et al. v. Bausch & Lomb (Australia) Pty. Ltd. et al.*, In the Federal Court of Australia Victoria District Registry, Applicants' Opening Submissions, No. V81 of 2000, pp. 1–16, Sep. 29, 2003 (Glossary of Ophthalmic Terms pp. 1–8).

*Novartis AG et al. v. Bausch & Lomb (Australia) Pty. Ltd. et al.*, In the Federal Court of Australia Victoria District Registry, Applicants' Supplementary Closing Submissions, No. V81 of 2000, pp. 1–3, Nov. 28, 2003.

*Novartis AG et al. v. Bausch & Lomb (Australia) Pty. Ltd. et al.*, In the Federal Court of Australia Victoria District Registry, Applicants' Reply Submissions, No. V81 of 2000, pp. 1–12, Dec. 5, 2003.

*Novartis AG et al. v. Bausch & Lomb (Australia) Pty. Ltd. et al.*, In the Federal Court of Australia Victoria District Registry, Applicants' Closing Submissions, No. V81 of 2000, pp. 1–27, Nov. 19, 2003.

*Novartis AG et al. v. Bausch & Lomb (Australia) Pty. Ltd. et al.*, In the Federal Court of Australia Victoria District Registry, Applicants' Outline of Submissions for Amendment, No. V81 of 2000, pp. 1–5, Aug. 25, 2003.

*Novartis AG et al. v. Bausch & Lomb (Australia) Pty. Ltd. et al.*, In the Federal Court of Australia Victoria District Registry, Applicants' Further Supplementary Submissions, No. V81 of 2000, pp. 1–17, Undated.

*Novartis AG et al. v. Bausch & Lomb (Australia) Pty. Ltd. et al.*, In the Federal Court of Australia Victoria District Registry, Minutes of Consent Order, No. V81 of 2000, pp. 1–12, Dec. 2003.

*Johnson & Johnson Vision Care, Inc. v. Ciba Vision Corporation*, Complaint for Damages, Declaratory and Injunctive (sic) Relief and Demand for Jury Trial, United States District Court Middle District of Florida Jacksonville Division, Case No. 3:03–CV800–J–25TEM, Sep. 17, 2003, pp. 1–9.

* cited by examiner

EXTENDED WEAR OPHTHALMIC LENS

This application is a continuation of Ser. No. 09/262,542, filed Mar. 4, 1999 now abandoned, which is a continuation of Ser. No. 09/108,714, filed Jul. 1, 1998, now U.S. Pat. No. 5,965,631 which is a divisional of application Ser. No. 08/682,452, filed Jul. 17, 1996, now U.S. Pat. No. 5,849,811 which is a divisional of application Ser. No. 08/569,816, filed Dec. 8, 1995 now U.S. Pat. No. 5,760,100 which is a continuation-in-part of U.S. application Ser. No. 08/301,166, filed on Sep. 6, 1994 now abandoned. Priority is also claimed 119 for German Application No. 95810221.2 filed on Apr. 4, 1995 and Swiss Application No. 1496/95 filed on May 19, 1995.

BACKGROUND OF THE INVENTION

1. Field of the Invention

This invention relates broadly to lenses and polymeric materials useful in optic and ophthalmic arts. More specifically, this invention relates to polymeric materials and treatment processes useful in the manufacture of contact lenses. Still more specifically, this invention relates to contact lenses useful as extended-wear contact lenses.

2. Description of the Related Art

A wide variety of research has been conducted in the field of biocompatible polymers. The definition of the term "biocompatible" depends on the particular application for which the polymer is designed. In the field of ophthalmic lenses, and in particular in the field of contact lenses, a biocompatible lens may be generally defined as one which will not substantially damage the surrounding ocular tissue and ocular fluid during the time period of contact. The phrase "ophthalmically compatible" more appropriately describes the biocompatibility requirements of ophthalmic lenses.

One ophthalmic compatibility requirement for contact lenses is that the lens must allow oxygen to reach the cornea in an amount which is sufficient for long-term corneal health. The contact lens must allow oxygen from the surrounding air to reach the cornea because the cornea does not receive oxygen from the blood supply like other tissue. If sufficient oxygen does not reach the cornea, corneal swelling occurs. Extended periods of oxygen deprivation causes the undesirable growth of blood vessels in the cornea. "Soft" contact lenses conform closely to the shape of the eye, so oxygen cannot easily circumvent the lens. Thus, soft contact lenses must allow oxygen to diffuse through the lens to reach the cornea.

Another ophthalmic compatibility requirement for soft contact lenses is that the lens must not strongly adhere to the eye. Clearly, the consumer must be able to easily remove the lens from the eye for disinfecting, cleaning, or disposal. However, the lens must also be able to move on the eye in order to encourage tear flow between the lens and the eye. Tear flow between the lens and eye allows for debris, such as foreign particulates or dead epithelial cells, to be swept from beneath the lens and, ultimately, out of the tear fluid. Thus, a contact lens must not adhere to the eye so strongly that adequate movement of the lens on the eye is inhibited.

While there exist rigid gas permeable ("RGP") contact lenses which have high oxygen permeability and which move on the eye, RGP lenses are typically quite uncomfortable for the consumer. Thus, soft contact lenses are preferred by many consumers because of comfort. Moreover, a contact lens which may be continuously worn for a period of a day or more (including wear during periods of sleeping) requires comfort levels which exclude RGP lenses as popular extended-wear candidates.

In order to balance the ophthalmic compatibility and consumer comfort requirements in designing a daily wear soft contact lens, polymers and copolymers of 2-hydroxyethyl methacrylate (HEMA) were developed. These hydrophilic polymers move well on the eye and provide sufficient oxygen permeability for daily wear. Certain soft contact lenses have been approved by the FDA for extended wear periods of up to about 6 nights of overnight wear and seven days of daily wear. However, the consumer cannot safely and comfortably wear these poly(HEMA) lenses for extended periods of seven days or more, because the oxygen permeability is insufficient. True extended wear (i.e., seven days or more) of these lenses may result, at a minimum, in corneal swelling and development of surface blood vessels in the cornea.

In order to improve oxygen permeability, polymers containing silicone groups were developed. A variety of siloxane-containing polymers have been disclosed as having high oxygen permeability. For example, see U.S. Pat. Nos. 3,228,741; 3,341,490; 3,996,187; and 3,996,189. However, polysiloxanes are typically highly lipophilic. The properties (e.g., lipophilicity, glass transition temperature, mechanical properties) of known polysiloxanes has resulted in contact lenses which adhere to the eye, inhibiting the necessary lens movement. In addition, polysiloxane lipophilicity promotes adhesion to the lens of lipids and proteins in the tear fluid, causing a haze which interferes with vision through the lens.

There have been attempts to blend the desirable hydrophilic properties of hydrophilic polymers, formed from monomers such as HEMA, with the desirable oxygen permeability of polymers formed from siloxane-containing monomers. For example, see U.S. Pat. Nos. 3,808,178; 4,136,250; and 5,070,169. However, prior attempts at producing a true extended wear contact lens have been unsuccessful, either because of the effect of the extended-wear lens on corneal health or because the lens would not move on the eye. Thus, there remains a need for an ophthalmically compatible, transparent polymeric material which is suited to extended periods of continuous contact with ocular tissue and tear fluid.

OBJECTS AND SUMMARY OF THE INVENTION

An object of the invention is to provide a material having a balance of oxygen permeability, ion permeability, on-eye movement and tear exchange, all of which are sufficient for corneal health and wearer comfort during extended periods of continuous wear.

Another object of the invention is to provide an ophthalmic lens capable of extended continuous wear periods of at least 24 hours without substantial adverse impact on ocular health or consumer comfort, and more preferably, to provide a lens capable of continuous wear of 4 to 30 days or more without substantial adverse impact on ocular health or consumer comfort.

A further object of the invention is to provide an ophthalmic lens capable of extended continuous wear periods of at least 24 hours without substantial corneal swelling or consumer discomfort, and more preferably, to provide a lens capable of continuous wear of 4, 7, 14 or 30 days or more without substantial corneal swelling or consumer discomfort.

Yet another object of the invention is to provide methods of forming an extended-wear ophthalmic lens.

Still a further object of the invention is to provide methods of testing and classifying ophthalmic lenses as candidates for true extended-wear.

These and other objects of the invention are met by the various embodiments described herein.

One embodiment of the invention is an ophthalmic lens, suited to extended periods of wear in continuous, intimate contact with ocular tissue and tear fluid. The lens displays a balance of oxygen permeability and ion permeability sufficient to maintain good corneal health, adequate movement of the lens on the eye and wearer comfort during extended wear periods. The lens is formed by polymerization, preferably copolymerization, of (a) at least one oxyperm polymerizable material which is capable of polymerizing to form a polymer having a high oxygen permeability; and (b) at least one ionoperm polymerizable material which is capable of polymerizing to form a polymer having a high ion permeability. Preferably, the lens includes a core polymeric material and ophthalmically compatible surfaces. In a preferred embodiment, the surface is more hydrophilic and lipophobic than the core polymeric material.

Another embodiment of the invention is a method of forming an ophthalmic lens having high oxygen permeability and high ion permeability. The method includes the step of forming a core material, having an inner surface and an outer surface, such that at least one pathway for ion transport and at least one pathway for oxygen transport are present from the inner to the outer surface. In a preferred embodiment, the method includes treating the surface of the lens to render the surface more hydrophilic than the core.

A further embodiment of the invention is an ophthalmic lens comprising a polymeric material which has a high oxygen permeability and a high ion or water permeability, the polymeric material being formed from at least one polymerizable material including (a) at least one oxyperm segment and (b) at least one ionoperm segment. The lens displays a balance of oxygen permeability and ion permeability sufficient to maintain good corneal health, adequate movement of the lens on the eye and wearer comfort during extended wear periods.

Yet another embodiment of the invention is a method of using a contact lens having both an oxygen transmission pathway and an ion transmission pathway from inner to outer surface as an extended wear lens. The method includes (a) applying the lens to the ocular environment and (b) allowing the lens to remain in intimate contact with the ocular environment for a period of at least 24 hours without substantial adverse impact on corneal health or wearer comfort. A preferred method includes additional steps of (c) removing the lens from the ocular environment; (d) disinfecting the lens; (e) applying the lens to the ocular environment; and (f) allowing the lens to remain in intimate contact with the ocular environment for a period of at least an additional 24 hours. In a preferred embodiment, the lens is worn for a continous period of at least seven days without substantial adverse impact on corneal health or wearer comfort.

OUTLINE OF DESCRIPTION OF THE PREFERRED EMBODIMENTS

I. DEFINITION OF TERMS
II. CORE POLYMER AND LENS
   A. Oxyperm polymerizable materials
   B. Ionoperm polymerizable materials
   C. Weight ratio of oxyperm to ionoperm polymerizable materials
   D. Morphology
   E. Bulk Water Content
   F. Ion and Water Permeability
      1. Ionoflux Ion Permeability Measurements
      2. Ionoton Ion Permeability Measurements
      3. Hydrodell Water Permeability Measurements
   G. Oxygen Permeability and Transmissibility
   H. Mechanical On-eye Movement Parameters
      1. Tensile Modulus and Short Relaxation Time
      2. Tangent Delta
      3. Parameter Combinations
   I. Examples of suitable materials
      1. Material "A"
      2. Material "B"
      3. Material "C"
      4. Material "D"
III. OPHTHALMICALLY COMPATIBLE SURFACES
IV. UTILITY
   A. Ophthalmic lenses
   B. Contact lenses
V. METHODS OF USE AS EXTENDED-WEAR LENSES
VI. METHODS OF MANUFACTURE OF LENSES

DESCRIPTION OF THE PREFERRED EMBODIMENTS

One embodiment of the present invention is an ophthalmically compatible, transparent lens suited to extended periods of continuous contact with ocular tissue and tear fluids. A particularly preferred embodiment of the invention is an extended-wear vision correction lens suited for safe and comfortable long term wear without removal. In order to properly describe the invention and to delineate the metes and bounds of the claims, a set of basic terms will be defined at the outset.

I. DEFINITION OF TERMS

An "ophthalmic lens", as used herein, refers to lenses which are placed in intimate contact with the eye or tear fluid, such as contact lenses for vision correction (e.g., spherical, toric, bifocal), contact lenses for modification of eye color, ophthalmic drug delivery devices, ocular tissue protective devices (e.g., ophthalmic healing promoting lenses), and the like. A particularly preferred ophthalmic lens is an extended-wear contact lens, especially extended-wear contact lenses for vision correction.

A "polymerizable material which is capable of polymerizing to form a polymer having a high oxygen permeability", as used herein, refers to monomers, oligomers, macromers, and the like, and mixtures thereof, which are capable of polymerizing with like or unlike polymerizable materials to form a polymer which displays a relatively high rate of oxygen diffusion therethrough. For convenience of reference, these materials will be referred to herein as "oxyperm polymerizable materials" and the resultant polymers will be referred to herein as "oxyperm polymers".

The "oxygen transmissibility" of a lens, as used herein, is the rate at which oxygen will pass through a specific ophthalmic lens. Oxygen transmissibility, Dk/t, is conventionally expressed in units of barrers/mm, where t is the average thickness of the material [in units of mm] over the area being measured and "barrer" is defined as:

$$[(cm^3\ oxygen)(mm)/(cm^2)(sec)(mm\ Hg)] \times 10^{-9}$$

The "oxygen permeability", Dk, of a lens material does not depend on lens thickness. Oxygen permeability is the rate at which oxygen will pass through a material. Oxygen permeability is conventionally expressed in units of barrers, where "barrer" is defined as:

$$[(cm^3\ oxygen)(mm)/(cm^2)(sec)(mm\ Hg)] \times 10^{-10}$$

These are the units commonly used in the art. Thus, in order to be consistent with the use in the art, the unit "barrer" will have the meanings as defined above. For example, a lens having a Dk of 90 barrers ("oxygen permeability barrers") and a thickness of 90 microns (0.090 mm) would have a Dk/t of 100 barrers/mm ("oxygen transmissibility barrers"/mm).

A "polymerizable material which is capable of polymerizing to form a polymer having a high ion permeability", as used herein, refers to monomers, oligomers, macromers, and the like, and mixtures thereof, which are capable of polymerizing with like or unlike polymerizable materials to form a polymer which displays a relatively high rate of ion or water permeation therethrough. For convenience of reference, these materials will be referred to herein as "ionoperm polymerizable materials" and the resultant polymers will be referred to herein as "ionoperm polymers".

A "macromer", as used herein, refers to a polymerizable material which has a molecular weight of at least about 800 grams/mol. The term "macromer", as used herein, also encompasses oligomers.

A "monomer", as used herein refers to a polymerizable material which has a molecular weight of less than about 800 grams/mol.

A "phase", as used herein, refers to a region of substantially uniform composition which is a distinct and physically separate portion of a heterogeneous polymeric material. However, the term "phase" does not imply that the material described is a chemically pure substance, but merely that certain bulk properties differ significantly from the properties of another phase within the material. Thus, with respect to the polymeric components of a lens, an ionoperm phase refers to a region composed of essentially only ionoperm polymer (and water, when hydrated), while an oxyperm phase refers to a region composed of essentially only oxyperm polymer.

A "continuous phase" as used herein, refers to a region of substantially uniform composition which forms a continuous pathway from one surface of an article to another surface of an article.

"Co-continuous phases", as used herein, refers to at least two regions, each of substantially uniform composition which differs from the other, and each of which forms a continuous pathway from one surface of an article to another surface of an article. Thus, an ophthalmic lens having co-continuous phases of oxyperm polymer and ionoperm polymer will have two continuous pathways or sets of continuous pathways extending from the inner surface of the lens to the outer surface of the lens.

"Morphology", as used herein, refers to the structure and relationship of the phases of a material.

"Ophthalmically compatible" as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of lipid adsorption, and will not cause substantial wearer discomfort during the prescribed period of wear.

"Ocular environment" as used herein, refers to ocular fluids (e.g., tear fluid) and ocular tissue (e.g., the cornea) which may come into intimate contact with a contact lens used for vision correction, drug delivery, wound healing, eye color modification, or other ophthalmic applications.

"Hydrophilic" as used herein, describes a material or portion thereof which will more readily associate with water than with lipids.

A "hydrophilic surface" as used herein, refers to a surface which is more hydrophilic and lipophobic than the bulk or core material of an article. Thus, an ophthalmic lens having a hydrophilic surface describes a lens having a core material having a certain hydrophilicity surrounded, at least in part, by a surface which is more hydrophilic than the core.

The "outer surface" of a lens, as used herein, refers to the surface of the lens which faces away from the eye during wear. The outer surface, which is typically substantially convex, may also be referred to as the front curve of the lens. The "inner surface" of a lens, as used herein, refers to the surface of the lens which faces towards the eye during wear. The inner surface, which is typically substantially concave, may also be referred to as the base curve of the lens.

"TRIS" as used herein, refers to 3-methacryloxypropyltris (trimethylsiloxy) silane, which is represented by CAS No. 17096-07-0. The term "TRIS" also includes dimers of 3-methacryloxypropyltris(trimethylsiloxy) silane.

"Molecular weight" of a polymeric material (including monomeric or macromeric materials), as used herein, refers to the number-average molecular weight unless otherwise specifically noted or unless testing conditions indicate otherwise.

A. Oxyperm Polymerizable Materials

Oxyperm polymerizable materials include a wide range of materials which may be polymerized to form a polymer displaying a relatively high oxygen diffusion rate therethrough. In addition, these materials must be relatively ophthalmically compatible. These oxyperm polymerizable materials include, without limitation thereto, siloxane-containing macromers and monomers, fluorine-containing macromers and monomers, and carbon-carbon triple bond-containing macromers and monomers. The oxyperm macromer or monomer may also contain hydrophilic groups.

Preferred oxyperm polymers are those formed from a siloxane-containing macromer. Macromers having dialkyl siloxane groups, especially dimethyl siloxanes, are particularly preferred. These macromers are broadly referred to as poly(dimethyl siloxanes) (also, PDMS). The siloxane-containing macromer may also include hydrophilic groups. Examples of suitable siloxane-containing macromers include, without limitation thereto, the Materials A, B, C, and D as described herein.

The oxygen transmissibility (Dk/t) of the lens is preferably at least 70 barrers/mm, more preferably at least 75 barrers/mm, and most preferably at least 87 barrers/mm. The lens center thickness is typically more than about 30 microns, preferably about 30 to about 200 microns, more preferably about 40 to about 150 microns, even more preferably about 50 to about 120 microns, and most preferably about 60 to about 100 microns.

The oxygen transmissibility of the extended-wear lens from the outer surface to the inner surface must be sufficient to prevent any substantial corneal swelling during the period of extended wear. It is known that the cornea swells approximately 3% to 4% during overnight periods of sleep when the eyelids are closed, as a result of oxygen deprivation. It is also known that wearing a typical contact lens, such as ACUVUE (Johnson & Johnson), for a period of about 8 hours (overnight wear) causes corneal swelling of about 11%. However, a preferred extended-wear contact lens will produce, after wear of about 24 hours, including normal sleep periods, corneal swelling of less than about 8%, more preferably less than about 6%, and most preferably less than about 4%. A preferred extended-wear contact lens will produce, after wear of about 7 days, including normal sleep periods, corneal swelling of less than about 10%, more preferably less than about 7%, and most preferably less than about 5%. Thus, the extended-wear lens must have oxyperm polymer in an amount sufficient to produce oxygen diffusion pathways from the outer surface to the inner surface of the lens which are sufficient to yield the above properties relating to corneal swelling. Preferably, the extended-wear lens has a continuous phase of oxyperm polymer extending from the outer surface to the inner surface of the lens.

B. Ionoperm Polymerizable Materials

Ionoperm polymerizable materials include a wide range of materials which may be polymerized to form a polymer displaying a relatively high ion diffusion rate therethrough. In addition, these materials must be relatively ophthalmically compatible. These ionoperm polymerizable materials include, without limitation thereto, acrylates and methacrylates, such as 2-hydroxyethyl methacrylate, acrylamide, methacrylamide, and dimethylacrylamide; poly(alkylene glycols), such as poly(ethylene glycol); N-vinyl pyrrolidones such as N-vinyl-2-pyrrolidone; and the like and mixtures thereof. Other ionoperm materials are disclosed in the specific embodiments of Materials A–D, described below.

C. Weight Ratios

The ratios of oxyperm to ionoperm polymerizable materials may vary substantially, depending on the selected balance of oxygen permeability and ion permeability for the chosen end-use of the molded polymeric article. Preferably, the volumetric ratio of oxyperm to ionoperm material (including water) in the fully hydrated lens is about 40 to about 60 to about 60 to about 40. However, weight percentages, based on the total weight of the lens, will be defined because weight percentages are more conveniently utilized in lens fabrication. Preferably, the extended-wear contact lenses having substantially only ionoperm and oxyperm materials will have about 60 to about 85 weight percent oxyperm polymerizable material and about 15 to about 40 weight percent ionoperm polymerizable material in the prepolymerization mixture, based on total polymerizable material weight. More preferably, the prepolymerization mixture will contain about 70 to about 82 weight percent oxyperm polymerizable material and about 18 to about 30 weight percent ionoperm polymerizable material, based on total polymerizable material weight.

A wide variety of additional polymerizable materials may be included in the mixture prior to polymerization. Cross-linking agents, such as ethylene glycol dimethacrylate (EGDMA), may be added to improve structural integrity and mechanical strength. Antimicrobial polymerizable materials such as poly(quaternary ammonium) salts may be added to inhibit microbial growth on the lens material. Also, additional ionoperm monomers or macromers and oxyperm polymerizable materials may be added to adjust the oxygen permeability and ion permeability of the final molded article. An especially advantageous polymerizable material is TRIS, which may act both to increase oxygen permeability and to improve the modulus of elasticity.

A preferred prepolymerization mixture will include (a) about 30 to 60 weight percent oxyperm macromer, (b) about 20 to 40 weight percent ionoperm polymerizable material, and (c) about 1 to 35 weight percent TRIS, based on the total lens weight. More preferably, the amount of TRIS is about 10 to 33 weight percent, based on the total prepolymerization mixture weight.

In a preferred embodiment, the prepolymerization mixture includes less than about 5 weight percent cross-linking agent, based on the total prepolymerization mixture weight. More preferably, the prepolymerization mixture includes less than about 2 weight percent cross-linking agent, based on the total prepolymerization mixture weight. Even more preferably, the prepolymerization mixture includes substantially no cross-linking agent. In a a particularly preferred embodiment, the prepolymerization mixture includes no added cross-linking agent.

The previously described ranges for oxyperm polymerizable materials, ionoperm polymerizable materials, and TRIS are offered to enable the reader to better comprehend the invention. However, it should be noted that the specific weight or volume percentages of oxyperm and ionoperm polymerizable materials are not the most critical factors to consider in preparing a good extended-wear ophthalmic lens. More importantly, the lens must have sufficient ion permeability for good on-eye movement and sufficient oxygen permeability for good corneal health during the extended wear period.

D. Morphology

One requirement of the lens material is that the lens allow a high visible light transmission from the outer to inner surface of the lens. A lens morphology which includes large phase separated regions will reduce visible light transmission and cause substantial undesirable image distortion, thereby destroying the value of the lens as a vision correction device. Thus, the lens must have a morphology which allows at least about 80%, more preferably about 90%, visible light transmission and does not produce any significant undesirable image distortion.

In one preferred embodiment, the lens material has at least two phases: the phases including at least one oxyperm phase and at least one ionoperm phase. While there may be two distinct phases, it is believed that there may be a transition phase, or interphase, in which the material composition and the material properties are a blend of those of the oxyperm and ionoperm materials. Thus, there may exist a distinct oxyperm phase or plurality of distinct oxyperm phases, a distinct ionoperm phase or a plurality of distinct ionoperm phases, and an amphipathic phase mixture or blend of oxyperm and ionoperm phases. In one preferred embodiment, the glass transition temperature (Tg) of the oxyperm phase is less than about −115° Celsius.

The existence of separate oxyperm and ionoperm phases, rather than a complete blend of oxyperm and ionoperm phases, is believed to be advantageous in promoting the diffusion of oxygen and ions. Oxygen will diffuse predominantly through the oxyperm polymer, while the ionoperm polymer provides a higher barrier to oxygen diffusion. Similarly, ions will diffuse well through the ionoperm polymer, but the oxyperm polymer provides a higher resistance to ion diffusion. Thus, one homogeneous oxyperm/ionoperm phase will provide undesirable resistance to both oxygen and ion diffusion, while two separate oxyperm and ionoperm phases will provide low resistance pathways for transmission of both oxygen and ions or water. Thus, the ideal extended-wear lens has a pathway or series of pathways from the outer surface to the inner surface for transmission of oxygen therethrough, and an analogous continuous pathway or series of pathways for transmission of water or ions therethrough. In a particularly preferred embodiment, the lens has two co-continuous phases, one an oxyperm phase and the other an ionoperm phase, allowing for permeation of water or ions and oxygen between the front and base curves of the lens.

E. Bulk Water Content

The measurement of water content is difficult because the removal of adhered surface droplets, without affecting the bulk lens water content, is difficult. In addition, water may evaporate from the lens surface quickly, thereby lowering the water content from the equilibrium level. Accordingly, a discussion of the bulk water content of a lens warrants a discussion of the measurement technique used to determine the water content.

The preferred bulk water content of the hydrated lens will be a function of the lens material properties. The material properties are dependent on the prepolymerization macromers and monomers and polymerization conditions. Thus, the preferred water content for a lens including a fluorine-containing oxyperm material may be different from that of a lens including a siloxane-containing oxyperm material. Accordingly, while general ranges for bulk water content are offered for a better understanding of the invention, the invention is not generally limited to specific bulk water contents.

One method of measuring the water content of a lens formed in accordance with the present invention, referred to herein as the "Bulk Technique" is as follows. First the lens is thoroughly hydrated in a physiological saline solution, such that the water in the lens is in equilibrium with the surrounding water. Next the lens is gently blotted between two lint-free blotting cloths to remove surface moisture. The lens is quickly placed on an aluminum weighing pan and the first wet weight, $W_1$, is measured. Next, the aluminum pan with lens is placed in a oven at 36° C. for a period of at least 24 hours. After heat treating, the pan with lens is removed, placed in a desiccator, and allowed to cool to room temperature (about 22° C.). The pan with lens is weighed again to determine the dry weight, $W_d$. The lens is re-equilibrated in physiological saline solution and a second wet weight $W_2$ is determined thereon. The wet weights ($W_1$ and $W_2$) are averaged to yield an average wet weight, $W_w$. The bulk water content is determined by the following equation:

Percent water content=$(W_w-W_d)/W_w \times 100$

A preferred lens bulk water content, determined by the "Bulk Technique" is less than about 32 weight percent. More preferably, the lens has a water content of about 10 to 30 weight percent, based on the total lens weight. A particularly preferred lens water content is about 15 to about 25 weight percent.

F. Ion and Water Permeability

Unexpectedly, it has been determined that the ion permeability through the lens correlates well with on-eye movement. As discussed earlier, it is known that on-eye movement of the lens is required to ensure good tear exchange, and ultimately, to ensure good corneal health. While the invention is not bound by theory presented herein, it may be useful to discuss some theory for a better understanding of ways to practice the invention.

It is theorized that water permeability is an exceptionally important feature for an extended-wear lens which includes oxyperm polymers such as those disclosed herein. Siloxane-containing oxyperm materials tend to adhere strongly to the eye, thereby stopping on-eye movement. The ability to pass water through the lens is believed to allow a siloxane-containing polymeric lens to move on the eye, where the movement occurs via forces exerted by water being sqeezed out of the lens. The water permeability of the lens is also believed important in replenishing lens water content once pressure is removed. Further, the permeability of ions is believed to be directly proportional to the permeability of water. Thus, ion permeability is a predictor of on-eye movement.

However, regardless of whether the water permeability theory is a correct understanding of the actual on-eye movement phenomenon, it has been unexpectedly found that above a certain threshhold of ion permeability through a lens, from the inner surface of the lens to the outer, or vice versa, the lens will move on the eye, and below the threshhold the lens will adhere to the eye. Thus, the present innovative extended-wear contact lenses provide a balance between the relatively high oxygen permeability (and associated high binding capacity) of oxyperm materials with the low binding capacity (high on-eye movement) of ionoperm materials. It is believed that this is accomplished by providing a plurality of continuous ion transmission pathways for ion and water movement through the lens.

It should be noted that ions may move through the lens via these ion pathways by a number of means. For example, ions may diffuse through the lens because of concentration differences from one surface to another. Ions may also be forced through the ion pathways by the mechanical action of blinking, with the concomittent compression forces on the lens essentially squeezing water out of the lens. In addition, the charge nature of the surfaces may provide an electromotive force which drives ion permeation through the lens. At times, one of these driving forces may be larger than the others, while at other times the relative magnitude may reverse. This discussion is presented to clarify that the invention is not restricted by the method or driving force by which ions move through the lens.

Neither the measurement of water permeability nor ion permeability through an ophthalmic lens is considered a routine matter of testing in the industry. Accordingly, a discussion of the preferred ion or water permeability ranges warrants a discussion of the measurement techniques used to determine the permeability.

The water permeability of a lens may be determined from the rate of water permeation through the lens, from one surface to another surface. The water permeability of a lens may be determined by positioning a lens between two reservoirs holding solutions having known, and different, initial concentrations of radiolabeled water (e.g., tritiated water), and then measuring concentration of radiolabeled water in the "receiving" reservoir (the reservoir towards which the net flow of radiolabeled water is positive) as a function of time.

The relative ion permeability of a lens may be determined from the rate of ion permeation through the lens, from one surface to another surface. The rate of ion permeation may be determined by positioning a lens between two reservoirs holding solutions having known, and different, initial ion concentrations, and then measuring conductivity in the "receiving" reservoir (the reservoir towards which the net flow of ions is positive) as a function of time. The concentration of ions, such as sodium, can be measured accurately using a pH meter and an ion-selective electrode. Ions are believed to be transmitted through a lens, from inner to outer surfaces and vice versa, primarily by the diffusion of ions through water pathways in the lens. Ion permeability through a lens is believed to be directly proportional to water permeability through a lens.

1. Ionoflux Measurement Technique

The following technique, referred to herein as the "Ionoflux Technique", is a preferred method for determining the ion permeability of a lens. This technique may be used to determine the likelihood of adequate on-eye movement.

The "Ionoflux Technique" involves the use of a conductometer (LF 2000/C, catalog no. 35 300105, Wissenschaftlich-Technische Werkstätten GmbH (WTW), Germany), an electrode equipped with a temperature sensor (LR 01/T, catalog no. 302 520, WTW), a donor chamber containing a salt solution, a receiving chamber containing about 60 ml of deionized water, a stir bar and a thermostat.

The donor chamber is specially designed for sealing a contact lens thereto, so that the donor solution does not pass around the lens (i.e., ions may only pass through the lens). The donor chamber is composed of a glass tube which is threaded at the end which is immersed in the receiving solution. The glass tube includes a centrally located hole of about 9 mm in diameter. A lid, which is threaded to mate with the glass tube, holds a lens-retaining member which includes a centrally located hole of about 8 mm in diameter. The lens-retaining member includes a male portion adapted to mate with and seal the edges of the inner (concave) surface of a lens and a female portion adapted to mate with and seal the edges of the outer (convex) surface of a lens.

The lens to be measured is placed in the lens-retaining member, between the male and female portions. The male and female portions include flexible sealing rings which are positioned between the lens and the respective male or female portion. After positioning the lens in the lens-retaining member, the lens-retaining member is placed in the threaded lid. The lid is screwed onto the glass tube to define the donor chamber. The donor chamber is filled with 16 ml of 0.1 molar NaCl solution. The receiving chamber is filled with 60 ml of deionized water. The leads of the conductivity meter are immersed in the deionized water of the receiving chamber and a stir bar is added to the receiving chamber. The receiving chamber is placed in a thermostat and the temperature is held at about 35° C. Finally, the donor chamber is immersed in the receiving chamber.

Measurements of conductivity are taken every 20 minutes for about three hours, starting 10 minutes after immersion of the donor chamber into the receiving chamber. The Ionoflux Diffusion Coefficient, D, is determined by applying Fick's law as follows:

$$D = -n'/(A \times dc/dx)$$

where
- n'=rate of ion transport [mol/min]
- A=area of lens exposed [mm$^2$]
- D=Ionoflux Diffusion Coefficient[mm$^2$/min]
- dc=concentration difference [mol/L]
- dx=thickness of lens [mm]

An Ionoflux Diffusion Coefficient of greater than about $1.5 \times 10^{-6}$ mm$^2$/min is preferred for achieving sufficient on-eye movement. More preferably, the Ionoflux Diffusion Coefficient is greater than about $2.6 \times 10^{-6}$ mm$^2$/min, while most preferably, the Ionoflux Diffusion Coefficient is greater than about $6.4 \times 10^{-6}$ mm$^2$/min. It must be emphasized that the Ionoflux Diffusion Coefficient correlates with ion permeability through the lens, and thereby is a predictor of on-eye movement.

2. Ionoton Measurement Technique

The following technique, referred to herein as the "Ionoton Technique", is another preferred method for determining the relative ion permeability of a lens. The technique is based on measurement of the diffusion of sodium chloride through a lens.

The "Ionoton Technique" involves the use of a pH meter (Beckman, VWR catalog no. BK123142), a VSC-1 Diffusion Cell Drive Console (Crown-Bio, Somerville, N.J.), a DCB-100B Diffusion Cell (Crown-Bio), and a 6 cm sodium ion-specific electrode (Microelectronics, Londonderry, N.H., catalog no. MI-414P). The technique is not limited to the aforementioned instruments or materials; equivalent instruments or materials may be used.

First, a contact lens is mounted onto an orifice of the DCB-100B cell chamber, the donor chamber. Next, the connecting cell chamber (receptor chamber) is placed against the cell chamber containing the contact lens and tightly clamped on the clamp holder supplied with the VSC-1 Drive Console. Then, a phosphate-buffered saline (PBS, Mediatech catalog no. 21-031-LV) is placed into the receptor side of the cell chamber. Stir bars are added to each cell chamber. The 6 cm electrode is placed into the PBS saline receptor side. After the electrode has equilibrated in the PBS saline, the pH meter is placed in the mV function to establish the 0 mV point. PBS which has been saturated with sodium chloride is added to the donor chamber.

The millivolt signal is recorded at 5, 10, 15, 30, 60, 120, and 180 minute intervals. The millivolt signal is converted to a sodium ion concentration by a standard curve of sodium ion concentration vs. millivolt signal. The Ionoton Ion Permeability Coefficient, P, is then determined in accordance with the following equation:

$$\ln(1 - 2C(t)/C(0)) = 2APt/Vd$$

where:
- C(t) concentration of sodium ions at time t in the receiving cell
- C(0)=initial concentration of sodium ions in donor cell
- A=membrane area, i.e., lens area exposed to cells
- V=volume of cell compartment (3.0 ml)
- d=average lens thickness in the area exposed
- P=permeability coefficient The average thickness of the lens in the exposed test area may be determined by averaging a number of readings, e.g., 10 readings, with a low-pressure thickness-measuring instrument, such as a Mitotoya micrometer VL-50, or equivalents thereof. The Ionoton Ion Permeability Coefficient, P, having units of cm$^2$/second, may be determined from the slope of a plot of time (t) v.$\ln(1 - 2C(t)/C(0)) \times (-2At/Vd)$.

An Ionoton Ion Permeability Coefficient, P, of greater than about $0.2 \times 10^{-6}$ cm$^2$/sec is preferred, while greater than about $0.3 \times 10^{-6}$ cm$^2$/sec is more preferred and greater than about $0.4 \times 10^{-6}$ cm$^2$/sec is most preferred. It must be emphasized that the Ionoton Ion Permeability Coefficient correlates with ion permeability through the lens, and thereby is a predictor of on-eye movement.

3. Hydrodell Water Permeability Technique

The following technique, referred to herein as the "Hydrodell Technique" is a preferred method for determining the water permeability of a lens. This technique may be used to determine the likelihood of adequate on-eye movement.

The Hydrodell Technique involves the measurement of the rate of transfer of the radiolabeled solutes THO ($^3$H—HO or tritiated water) and $^{14}$C-glucose across the contact lens using a two-chamber apparatus. $^{14}$C-glucose is used in this measurement technique to reveal any leak in the system during testing. The lens is mounted between chambers, which are stirred at a controllable rate. Chamber I contains a solution with a high concentration of labeled solute. Chamber II, the "receiving chamber" contains an identical solution but without the labeled solute. Samples of the solution in chambers I and II are taken at intervals over the test period. The radioactivity in the samples is measured. The permeability of the lens is calculated from the measured radioactivity, the sample times, the chamber volumes and the lens area exposed to the solutions. A more detailed description of the Hydrodell Technique follows.

a. Solution Preparation

Dulbecco's phosphate buffered saline (DPBS) is prepared by first dissolving, sequentially, about 160 g sodium chloride (NaCl), about 4 grams potassium chloride (KCl), about 23 grams disodium hydrogen orthophosphate ($Na_2HPO_4$), about 4 grams potassium dihydrogen orthophosphate ($KH_2PO_4$), and about 10 grams sodium azide in a liter of reverse-osmosis (MilliQ) water. Then, the pH is adjusted to about 7.3 by adding appropriate amounts of HCl. Finally, the buffer solution is diluted to 1:20 (50 ml buffer solution with 950 ml reverse-osmosis water). and allowed to degas either in a screw-capped container overnight or under vacuum.

A Cold Glucose buffer solution is prepared by adding about 0.1 grams D-glucose to one liter of DPBS, followed by sterilization via filtration through a 0.2 $\mu$l millipore filter and storage at 4° C. until use.

The Chamber I solution is prepared by adding about 6 $\mu$l THO (TR53, 1.0 mCi/ml activity, available from Amersham Australia, located in North Ryde NSW Australia) and about 16 $\mu$l $^{14}$C-glucose THO (in ethanol, available from Amersham Australia) to about 12 ml of the Cold Glucose buffer solution. Preferably, this solution is used within about 24 hours of preparation. The Chamber II solution is DPBS.

b. Apparatus Preparation

The chambers have a volume sufficient to hold about 12 ml of solution during testing. While the exact shape of the chambers is not critical, both chambers have rectangular cross-sections for ease of construction. The chambers may be made from a variety of water-proof rigid materials, preferably clear (e.g., acrylic plates, FX Plastics, Marrickville NSW Australia) so that samples may be observed during testing. Each chamber has a circular aperture of about 7 mm diameter appropriate for mounting a lens between the chambers for contact with solutions held withing the chambers. Some affixing means, such as a set of mounting bolts, are necessary to securely affix one chamber to the other with the lens mounted in between.

A test contact lens is mounted symmetrically over the aperture of Chamber II. Folds and wrinkles are manually removed from the lens. Chamber I is positioned adjacent the aperature and mounted lens of Chamber II, and the chambers are secured to one another using mounting bolts.

About 12 ml ($V_2$) of DPBS is placed in Chamber II. About 12 ml of the Chamber I labeled solution is placed in Chamber I, at which point time t=0 is established. Stirrers are added to both chambers and the stirrer speed is set at about 1200 rpm.

c. Sampling

Sampling generally starts at time $t_0$=5 minutes. The final sample time, $t_f$, is usually at about 50 minutes for high water content lenses and about 120 minutes for low water content lenses, although these times are not critical.

At time $t_0$=5 minutes, two samples of about 0.2 ml volume are pipetted from Chamber I, and two 0.2 ml aliquots of DPBS are added to Chamber I to restore the volume. These samples are placed into plastic counting tubes with about 4 ml Ultima Gold™ cocktail (available from Packard Instrument Co., Meriden, Conn.) and about 0.9 ml DPBS.

Also at time $t_0$, one sample of about 1.0 ml volume is pipetted from Chamber II and one 1.0 ml aliquot of DPBS is added to Chamber II to restore the volume. The sample is placed into a plastic counting tube with about 4 ml Ultima Gold™ cocktail.

At intermediate times between $t_0$ and $t_f$ (e.g., every 10 minutes), one sample of about 1.0 ml volume is pipetted from Chamber II and one 1.0 ml aliquot of DPBS is added to Chamber II to restore the volume. Each sample is placed into a plastic counting tube with about 4 ml Ultima Gold™ cocktail.

At time $t_f$, two samples of about 0.2 ml volume are pipetted from Chamber I. These samples are placed into plastic counting tubes with about 4 ml Ultima Gold™ cocktail and about 0.9 ml DPBS.

Also at time $t_f$, two samples of about 1.0 ml volume are pipetted from Chamber II. These samples are placed into plastic counting tubes with about 4 ml Ultima Gold™ cocktail.

d. Measurements

The activity of the samples are measured by liquid scintillation counting, or other appropriate technique. Liquid scintillation counting may be advantageously accomplished by using protocol number 6 for $^3H/^{14}C$ on a Tri-Carb Liquid Scintillation Analyzer (1900TR, available from Packard Instrument Co.).

Three standards containing about $10^4$ to $10^5$ cpm THO in reversed-osmosis (MilliQ) water are prepared. Three standards containing about $10^4$ to $10^5$ cpm $^{14}$C glucose in reversed-osmosis (MilliQ) water are also prepared. A blank containing MilliQ water is prepared.

The scintillation analyzer settings are LLA=0 KeV and ULA=12 KeV for $^3$H ("1") in channel 1 and LLB=12 KeV and ULB=156 KeV for $^{14}$C ("2") in channel 2. The standards and blank are counted three times during each counting of samples, and the counts are averaged. The following denote the relevant measured sample activities:

$b_1$=measured activity of blank sample in channel 1

$b_2$=measured activity of blank sample in channel 2

$S'_{11}$=measured activity of standard $^3$H sample in channel 1

$S'_{12}$=measured activity of standard $^{14}$C sample in channel 2

$S'_{21}$=measured activity of standard $^3$H sample in channel 1

$S'_{22}$=measured activity of standard $^{14}$C sample in channel 2

$y_1$=measured activity of test sample (both $^3$H and $^{14}$C) in channel 1

$Y_2$=measured activity of test sample (both $^3$H and $^{14}$C) in channel 2 e. Water Permeability Calculation

In order to calculate the actual activity of a sample, the measured activities of the isotopes, $^3$H and $^{14}$C, must first be corrected to remove the cross-contamination error due to the presence of both isotopes in one sample. Without explaining the mathematical derivations, the following stepwise procedure is offered as an example of one method of determining water permeability from the above measurements:

(1) Calculate $S_{11}$, $S_{12}$, $S_{21}$, and $S_{22}$, from the following equations:

$$S_{11}=S'_{11}-b_1$$

$$S_{12}=S'_{12}-b_1$$

$$S_{21}=S'_{21}-b_2$$

$$S_{22}=S'_{22}-b_2$$

(2) Calculate $a_{12}$ and $a_{21}$ from the following equations:

$$a_{12}=S_{12}/S_{22}$$

$$a_{21}=S_{21}/S_{11}$$

(3) Calculate corrected concentrations of $^3H$ ("1") and $^{14}C$ ("2") from the following equations:

$$c_1 = [(y_1-b_1)-a_{12}(y_2-b_2)]/(1-a_{12}a_{21})V$$

$$c_2 = [(y_2-b_2)-a_{21}(y_1-b_1)]/(1-a_{12}a_{21})V$$

where V is the volume of the test sample.

(4) Calculate water permeability for an interval from $t_1$ to $t_2$ as follows:

$$P = V_{II}[c_{II}(t_2)-c_{II}(t_1)]/A(c_I-c_{II})(t_1-t_2)$$

where $V_{II}$ is the volume of Chamber II, $c_{II}(t_2)$ is the concentration of $^3H$ in Chamber II at time $t_2$, $c_{II}(t_1)$ is the concentration of $^3H$ in Chamber II at time $t_1$, A is the area of lens exposure, $c_I$ is the average concentration of $^3H$ in Chamber I over the time period $t_1$ to $t_2$ and $c_{II}$ is the average concentration of $^3H$ in Chamber II over the time period $t_1$ to $t_2$.

The ophthalmic lenses of one embodiment of the present invention have a Hydrodell Water Permeability Coefficient of greater than about $0.2 \times 10^{-6}$ cm$^2$/min. The ophthalmic lenses in a preferred embodiment of the invention have Hydrodell Water Permeability Coefficient of greater than about $0.3 \times 10^{-6}$ cm$^2$/min. The ophthalmic lenses in a preferred embodiment of the invention have Hydrodell Water Permeability Coefficient of greater than about $0.4 \times 10^{-6}$ cm$^2$/min.

G. Oxygen Transmissibility and Permeability

As mentioned earlier, the cornea receives oxygen primarily from the corneal surface which is exposed to the environment, in contrast to other tissues which receives oxygen from blood flow. Thus, an ophthalmic lens which may be worn on the eye for extended periods of time must allow sufficient oxygen to permeate through the lens to the cornea to sustain corneal health. One result of the cornea receiving an inadequate amount of oxygen is that the cornea will swell. In a preferred embodiment, the oxygen transmissibility of the present ophthalmic lenses is sufficient to prevent any clinically significant amount of corneal swelling from occurring.

A preferred ophthalmic lens material will have an oxygen transmissibility, Dk/t, of at least 70 (cm$^3$ oxygen)(mm)/mm-cm$^2$ 33 (sec/mm Hg)$\times 10^{-9}$ or [barrers/mm], more preferably at least 75 barrers/mm, and most preferably at least 87 barrers/mm.

The oxygen permeability of a lens and oxygen transmissibility of a lens material may be determined by the following technique. Oxygen fluxes (J) are measured at 34 C. in a wet cell (i.e., gas streams are maintained at about 100% relative humidity) using a Dk1000 instrument (available from Applied Design and Development Co., Norcross, Ga.), or similar analytical instrument. An air stream, having a known percentage of oxygen (e.g., 21%), is passed across one side of the lens at a rate of about 10 to 20 cm$^3$/min., while a nitrogen stream is passed on the opposite side of the lens at a rate of about 10 to 20 cm$^3$/min. The barometric pressure surrounding the system, $P_{measured}$, is measured. The thickness (t) of the lens in the area being exposed for testing is determined by measuring about 10 locations with a Mitotoya micrometer VL-50, or similar instrument, and averaging the measurements. The oxygen concentration in the nitrogen stream (i.e., oxygen which diffuses through the lens) is measured using the DK1000 instrument. The oxygen permeability of the lens material, $D_k$, is determined from the following formula:

$$D_k = Jt/(P_{oxygen})$$

where
  J = oxygen flux [microliters $O_2$/cm$^2$-minute]
  $P_{oxygen} = (P_{measured}-P_{water\,vapor}) \times (\%O_2$ in air stream) [mm Hg] = partial pressure of oxygen in the air stream
  $P_{measured}$ = barometric pressure [mm Hg]
  $P_{water\,vapor}$ = 0 mm Hg at 34 C. (in a dry cell) [mm Hg]
  $P_{water\,vapor}$ = 40 mm Hg at 34 C. (in a wet cell) [mm Hg]
  t = average thickness of the lens over the exposed test area [mm]

where $D_k$ is expressed in units of barrers, i.e., [(cc oxygen)(mm)/cm$^2$]$\times$[sec/mm Hg]$\times 10^{-10}$.

The oxygen transmissibility ($D_k$/t) of the material may be calculated by dividing the oxygen permeability ($D_k$) by the average thickness (t) of the lens.

H. Mechanical On-eye Movement Parameters

On-eye movement of a lens may be predicted from the mechanical properties of a lens, the ion or water permeability through the lens, or both the mechanical properties and ion or water permeability. In fact, on-eye movement may be predicted more accurately from a combination of mechanical properties and ion or water permeability.

1. Tensile Modulus and Short Relaxation Time

Tensile mechanical testing may be performed on lens materials to determine mechanical properties. A procedure for preparing a test sample from a lens for subsequent mechanical testing includes the following steps:

1. Cut a parallel-sided strip through the center of the lens. A suitable width for the strip is about 3.1 mm.
2. Immerse the test strip in a phosphate-buffered saline solution (approximating ocular fluid osmolality) for a period of about 24 hours before testing.
3. Conduct mechanical testing with the test strip immersed in phosphate-buffered saline at ambient temperature (about 23° C.).

Tensile modulus may be measured by applying a strain rate of about 100% per minute to the test strip and recording the resultant stress. However, the procedure may be used at differing strain rates.

Stress relaxation is measured by applying a constant strain of about 5% to the test strip and recording the resultant stress for about 5 minutes. A useful mechanical testing instrument for this type of testing is the Vitrodyne V-200 from Liveco Biomechanical Instruments, located in Burlington, Vt.

In order to analyze stress relaxation data, a three element Maxwell-Wiechert model (a spring and two spring-dashpot elements in parallel) may be assumed for the polymer material. For this model the stress relaxation modulus is given by the following equation:

$$E(t) = E_0 + E_1 \exp(-t/t_1) + E_2 \exp(-t/t_2)$$

Stress v. time curves may be normalized to the maximum (initial) stress induced in the samples. These curves may be analyzed by a variety of commercially available software (for example, ORIGIN software) by fitting the double exponential equation:

$$y(t) = y_0 + A_1 \exp(-t/t_1) + A_2 \exp(-t/t_2)$$

in order to obtain the stress relaxation parameters $y_0$, $t_1$, $A_1$, $t_2$, and $A_2$.

It has been determined that the tensile modulus (modulus of elasticity, E) and the short relaxation time constant ($t_1$)

correlate well with on-eye movement. In order to have appropriate on-eye movement, a lens preferably has a tensile modulus of less than about 3 MPa. More preferably, E is about 0.4 to about 2.5 MPa while a particularly preferred E is about 0.5 to about 1.5 MPa.

A preferred short relaxation time constant ($t_1$) is greater than about 3.5 seconds. More preferably, $t_1$ is greater than about 4 seconds, while a particularly preferred $t_1$ is greater than about 4.5 seconds.

2. Tangent Delta

Lenses may also be evaluated by dynamic mechanical analysis (DMA) methods. It has been determined that a factor known as tan δ (i.e., tangent delta), also known as mechanical loss factor, correlates well with on-eye movement. It has been observed that lens materials which move on the eye exhibit a distinct increase in tan δ with increasing frequency from about 0.1 to 10 Hz when these materials are tested by dynamic mechanical analysis. The tan δ of a preferred lens material is above about 0.2 at 0.1 Hz and increases to about 0.25 or more at about 10 Hz. A tan δ of about 0.3 or greater at 10 Hz is more preferred, while a tan δ of about 0.5 or greater at 10 Hz is even more preferred.

DMA measurements may be determined in accordance with the following procedure. A disk of lens material having a diameter of about 3.0 mm and a thickness of about 0.50 mm is formed. The disk is placed in a Perkin-Elmer DMA-7 instrument. The disk is immersed in a solution buffered to a pH of about 7.2 and held isothermally for a period of about 10 minutes or more prior to testing, at a temperature of about 23 to 35° C. The instrument is set to a compression measuring mode and the strain on the sample is adjusted to about 2% to 4%, depending on the sample response. The amplitude of compression is about 2 to 4 μm. Measurements of the modulus of elasticity and tan δ are taken at frequencies of about 0.1, about 1, and about 10 Hz.

3. Parameter Combinations

In order to assure appropriate movement of the lens on the eye, one may select materials which have a combination of the above-discussed properties. Therefore, a preferred group of extended-wear contact lens materials have (a) a modulus of elasticity (E) of about 1.5 MPa or less, (b) a short time relaxation constant ($t_1$) of greater than about 4 seconds, and (c) an Ionoton Ion Permeability Coefficient of greater than about $0.3 \times 10^{-6}$ cm$^2$/sec and/or an Ionoflux Diffusion Coefficient greater than about $6.4 \times 10^{-6}$ mm$^2$/min.

I. Examples of Suitable Materials

1. Material "A"

One embodiment of a suitable core material of the present ophthalmic lenses is a copolymer formed from the following monomeric and macromeric components:

(a) about 5 to about 94 dry weight percent of a macromer having the segment of the formula

CP-PAO-DU-ALK-PDMS-ALK-DU-PAO-CP where

PDMS is a divalent poly(disubstituted siloxane),

ALK is an alkylene or alkylenoxy group having at least 3 carbon atoms,

DU is a diurethane-containing group,

PAO is a divalent polyoxyalkylene, and

CP is selected from acrylates and methacrylates, wherein said macromer has a number-average molecular weight of 2000 to 10,000;

(b) about 5 to about 60 weight percent methacryloxypropyltris(trimethylsiloxy)silane;

(c) about 1 to about 30 weight percent of an acrylate or methacrylate monomer; and (d) 0 to 5 weight percent cross-linking agent, with the weight percentages being based upon the dry weight of the polymer components.

A preferred polysiloxane macromer segment is defined by the formula

CP-PAO-DU-ALK-PDMS-ALK-DU-PAO-CP where

PDMS is a divalent poly(disubstituted siloxane);

CP is an isocyanatoalkyl acrylate or methacylate, preferably isocyanatoethyl methacrylate, where the urethane group is bonded to the terminal carbon on the PAO group;

PAO is a divalent polyoxyalkylene (which may be substituted), and is preferably a polyethylene oxide, i.e., $(-CH_2-CH_2-O-)_m CH_2 CH_2-$ where m may range from about 3 to about 44, more preferably about 4 to about 24;

DU is a diurethane, preferably including a cyclic structure, where an oxygen of the urethane linkage (1) is bonded to the PAO group and an oxygen of the urethane linkage (2) is bonded to the ALK group;

and ALK is an alkylene or alkylenoxy group having at least 3 carbon atoms, preferably a branched alkylene group or an alkylenoxy group having 3 to 6 carbon atoms, and most preferably a sec-butyl (i.e., $-CH_2CH_2CH(CH_3)-$) group or an ethoxypropoxy group (e.g., $-O-(CH_2)_2-O-(CH_2)_3-$).

It will be noted that the DU group can be formed from a wide variety of diisocyanates or triisocyanates, including aliphatic, cycloaliphatic or aromatic polyisocyanates. These isocyanates include, without limitation thereto, ethylene diisocyanate; 1,2-diisocyanatopropane; 1,3-diisocyanatopropane; 1,6-diisocyanatohexane; 1,2-diisocyanatocyclohexane; 1,3-diisocyanatocyclohexane; 1,4-diisocyanatobenzene, bis(4-isocyanatocyclohexyl) methane; bis(4-isocyanatocyclohexyl)methane, bis(4-isocyanatophenyl)methane; 1,2- and 1,4-toluene diisocyanate; 3,3-dichloro-4,4'-diisocyanatobiphenyl; tris(4-isocyanatophenyl)methane; 1,5-diisocyanatonaphthalene; hydrogenated toluene diisocyanate; 1-isocyanatomethyl-5-isocyanato-1,3,3-trimethylcyclohexane (i.e., isophorone diisocyanate); 1,3,5-tris(6-isocyanatohexyl) biuret; 1,6-diisocyanato-2,2,4-(2,4,4)-trimethylhexane; 2,2'-diisocyanatodiethyl fumarate; 1,5-diisocyanato-1-carboxypentane; 1,2-, 1,3-, 1,6-, 1,7-, 1,8-, 2,7- and 2,3-diisocyanatonaphthalene; 2,4- and 2,7-diisocyanato-1-methylnaphthalene; 1,4-diisocyanatomethylcyclohexane; 1,3-diisocyanato-6(7)-methylnaphthalene; 4,4'-diisocyanatobiphenyl; 4,4'-diisocyanato-3,3'-dimethoxybisphenyl; 3,3'- and 4,4'-diisocyanato-2,2'-dimethylbisphenyl; bis(4-isocyanatophenyl) ethane; bis(4-isocyanatophenyl ether); 1,2- or 1,4-toluene diisocyanate; and mixtures thereof. Preferably DU is formed from isophorone diisocyanate or toluene diisocyanate, and more preferably, isophorone diisocyanate, where one isomeric diurethane structure of isophorone diisocyanate is defined above.

A preferred Material A macromer segment has the following formula:

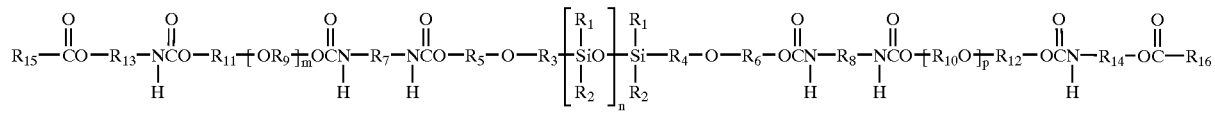

wherein:
- $R_1$ and $R_2$ are lower alkyl ($C_1$–$C_6$), preferably $C_1$–$C_3$ alkyl, more preferably methyl;
- $R_3$, $R_4$, $R_5$, and $R_6$ are lower alkylene ($C_1$–$C_6$), preferably $C_1$–$C_3$ alkylene, more preferably $C_2$–$C_3$ alkylene, and preferably, where the total number of carbon atoms in $R_3$ and $R_5$, or $R_4$ and $R_6$ is greater than 4;
- $R_7$ and $R_8$ are linear or branched alkylene or an bivalent cycloalkylene, preferably bivalent cycloalkylene;
- $R_9$, $R_{10}$, $R_{11}$, and $R_{12}$ are $C_1$–$C_2$ alkylene, preferably $C_2$ alkylene;
- $R_{13}$ and $R_{14}$ are lower alkenylene ($C_1$–$C_6$), preferably $C_1$–$C_3$ alkenylene, more preferably ethylene; and
- $R_{15}$ and $R_{16}$ are linear or branched lower alkenylene, preferably $C_2$–$C_3$ alkenylene;
- m and p, independently of one another, may range from about 3 to about 44, more preferably about 4 to about 24; and
- n may range from about 13 to about 80, more preferably, about 20 to about 50, and even more preferably about 24 to about 30.

The polysiloxane macromer may be synthesized by the following preferred process. At about room temperature (about 20–25° C.), poly(dimethylsiloxane) dialkanol having hydroxyalkyl (e.g., hydroxy-sec-butyl) or hydroxyalkoxy (e.g., hydroxyethylpropoxy) end groups and having a molecular weight of about 2000 to 3000 (preferably about 2200, i.e., having about 28 repeating siloxane groups) is reacted with isophorone diisocyanate at about a 1:2 molar ratio, using about 0.2 weight percent (based on polydimethylsilane) dibutyltin dilaurate added as a catalyst. The reaction is carried out for about 36 to 60 hours. To this mixture is added poly(ethylene glycol) having a molecular weight of about 400 to 1200 (more preferably about 500 to 700) at about a 2:1 or 2.1:1 molar ratio with respect to the PDMS, about 0.4 to 0.5 weight percent dibutyltin dilaurate (based on polyethylene glycol weight), and chloroform sufficient to ensure substantial mixture homogeneity. The mixture is agitated for about 12 to 18 hours, then held at a temperature of about 44 to 48° C. for about 6 to 10 hours. Excess chloroform is evaporated therefrom at about room temperature to produce a composition having about 50 weight percent solids. Then, isocyanatoethyl methacrylate is added to the mixture in about a 2:1 to 2.3:1 molar ratio with respect to PDMS. The mixture is agitated at room temperature for about 15 to 20 hours. The resulting solution contains a polysiloxane macromer having the composition described above and a number-average molecular weight of about 2000 to 10,000, more preferably about 3000 to 5000.

An advantageous polymeric material formed from the Material A macromer of the present invention is a copolymer of the aforementioned Material A macromer; an acrylated or methacrylated siloxane monomer, preferably methacryloxypropyltris (trimethylsiloxy) silane (referred to herein as "Tris"); a hydrophilic monomer, preferably 2-hydroxyethyl methacrylate (HEMA); and preferably, a cross-linking agent such as ethylene glycol dimethacrylate (EGDMA). The final copolymer composition includes about 10 to 90, preferably 70 to 90, weight percent polysiloxane macromer; about 5 to 60, preferably about 8 to 20, weight percent siloxane monomer; about 1 to 30, preferably about 1 to 5, weight percent acrylate or methacrylate monomer; and 0 to about 5, preferably up to about 2 weight percent cross-linking agent (e.g., EGDMA) based on a total dry copolymer weight. A more preferred composition includes about 80 to 84 polysiloxane macromer, about 12 to 15 weight percent TRIS, about 3 to about 4 weight percent 2-hydroxyethyl methacrylate, and about 0.7 to about 1.2 weight percent ethylene glycol dimethacrylate.

The advantageous copolymers of the present invention may be formed from the previously-described polysiloxane macromer in the following manner. A monomeric solution is formed by adding Tris, HEMA, DAROCUR® 1173 (a photoinitator available from Ciba-Geigy Corporation), and optionally, EGDMA to the polysiloxane macromer solution. The resulting polymer precursor solution preferably contains about 83 to about 95 weight percent polysiloxane macromer solution, about 5 to about 10 weight percent Tris, about 0.5 to about 5 weight percent HEMA, about 0.1 to about 1.0 weight percent DAROCUR® 1173, and about 0.1 to about 1.0 weight percent EGDMA. More preferably, the monomer solution contains about 87 to about 93 weight percent polysiloxane macromer solution, about 7 to about 8 weight percent Tris, about 2 to about 4 weight percent HEMA, about 0.3 to about 0.7 weight percent DAROCUR® 1173, and about 0.3 to about 0.7 weight percent EGDMA. The monomer solution is preferably agitated for about 8 to about 24 hours prior to the polymerization step.

Contact lenses may be prepared from the monomer solution by applying the monomer solution to appropriate lens molds and applying sufficient ultraviolet (UV) radiation to initiate polymerization. The ultraviolet light may be applied for a period of a few minutes to about 5 hours, depending on the intensity of light applied. Subsequent to polymerization, the contact lens may be extracted with a solvent, e.g., isopropanol, to remove unreacted monomers.

Thus, generally, one embodiment of the present invention is a method of forming a molded polymeric article suitable for ophthalmic applications (especially a contact lens), including the following steps:
- (a) contacting a poly(dialkylsiloxane) dialkanol with a diisocyanate compound in the presence of a first catalyst at conditions sufficient to cause reaction of said dialkanol with said diisocyanate, thereby forming a first mixture;
- (b) contacting said first mixture with poly(alkylene glycol), a second catalyst, and sufficient solvent to ensure mixture homogeneity, thereby forming a second mixture;
- (c) evaporating sufficient solvent from said second mixture to generate a third mixture having a solids content of about 40 to 60 weight percent;
- (d) adding isocyanatoalkyl methacrylate to said third mixture, thereby forming a fourth mixture containing a polysiloxane macromer;

(e) adding to said fourth mixture 3-methacryloxypropyltris(trimethylsiloxy)silane (TRIS), a hydrophilic monomer, a cross-linking agent and a photoinitiator, thereby forming a fifth mixture;

(f) placing said fifth mixture into a mold; and (g) applying sufficient radiation to copolymerize said monomers, thereby forming said polymeric material into a molded polymeric article.

The hydrophilic copolymers of the present invention are especially advantageous in the formation of "soft" contact lenses. In the use of the copolymers in the contact lens field, the lenses have a water content of about 10 to about 50 weight percent, more preferably about 10 to about 30 weight percent, and most preferably about 15 to about 22 weight percent, based on total hydrophilic polymer weight. Preferably, the fully-hydrated contact lens has an oxygen transmissibility ($D_k/t$) of greater than 70 barrers/mm (i.e., [(cc oxygen)(mm)/cm$^2$]×[sec/mm Hg]×$10^{-10}$), more preferably greater than about 75 barrers/mm, and most preferably greater than about 87 barrers/mm.

2. Material "B"

Polysiloxane-comprising perfluoroalkyl ethers

The Material "B" macromer is defined by formula (I):

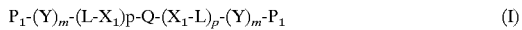

$$P_1\text{-}(Y)_m\text{-}(L\text{-}X_1)p\text{-}Q\text{-}(X_1\text{-}L)_p\text{-}(Y)_m\text{-}P_1 \quad (I)$$

where each P1, independently of the others, is a free-radical-polymerizable group;

each Y, independently of the others, is —CONHCOO—, —CONHCONH—, —OCONHCO—, —NHCONHCO—, —NHCO—, —CONH—, —NHCONH—, —COO—, —OCO—, —NHCOO— or —OCONH—;

m and p, independently of one another, are 0 or 1;

each L, independently of the others, is a divalent radical of an organic compound having up to 20 carbon atoms;

each $X_1$, independently of the others, is —NHCO—, CONH—, —NHCONH—, —COO—, —OCO—, —NHCOO— or —OCONH—; and Q is a bivalent polymer fragment consisting of the segments:

(a) —(E)$_k$—Z—CF$_2$—(OCF$_2$)$_x$—(OCF$_2$CF$_2$)$_y$—OCF$_2$—Z—(E)$_k$—, where x+y is a number in the range of 10 to 30;

each Z, independently of the others, is a divalent radical having up to 12 carbon atoms or Z is a bond;

each E, independently of the others, is —(OCH$_2$CH$_2$)$_q$—, where q has a value of from 0 to 2, and where the link —Z—E— represents the sequence —Z—(OCH$_2$CH$_2$)$_q$—; and k is 0 or 1;

(b)
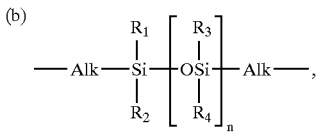

where n is an integer from 5 to 100;

Alk is alkylene having up to 20 carbon atoms;

80–100% of the radicals $R_1$, $R_2$, $R_3$ and $R_4$, independently of one another, are alkyl and 0–20% of the radicals $R_1$, $R_2$, $R_3$ and $R_4$, independently of one another, are alkenyl, aryl or cyanoalkyl; and (c) $X_2$—R—$X_2$, where R is a divalent organic radical having up to 20 carbon atoms, and each $X_2$, independently of the others, is —NHCO—, —CONH—, —NHCONH—, —COO—, —OCO—, —NHCOO— or OCONH—;

with the provisos that there must be at least one of each segment (a), (b), and (c) in Q, that each segment (a) or (b) has a segment (c) attached to it, and that each segment (c) has a segment (a) or (b) attached to it.

The number of segments (b) in the polymer fragment Q is preferably greater than or equal to the number of segments (a). The ratio between the number of segments (a) and (b) in the polymer fragment Q is preferably 3:4, 2:3, 1:2 or 1:1. The molar ratio between the number of segments (a) and (b) in the polymer fragment Q is more preferably 2:3, 1:2 or 1:1.

The mean molecular weight of the polymer fragment Q is in the range of about 1000 to about 20000, preferably in the range of about 3000 to about 15000, particularly preferably in the range of about 5000 to about 12000.

The total number of segments (a) and (b) in the polymer fragment Q is preferably in the range of 2 to about 11, particularly preferably in the range of 2 to about 9, and in particular in the range of 2 to about 7. The smallest polymer unit Q is preferably composed of one perfluoro segment (a), one siloxane segment (b) and one segment (c).

In a preferred embodiment of the polymer fragment Q, which preferably has a composition in the abovementioned ratios, the polymer fragment Q is terminated at each end by a siloxane segment (b).

The compositions in a bivalent polymer fragment Q always correspond above and below to a mean statistical composition. This means that, for example, even individual block copolymer radicals containing identical recurring units are included, so long as the final mean statistical composition is as specified.

$X_1$ is preferably —NHCONH—, —NHCOO— or —OCONH—, particularly preferably —NHCOO— or —OCONH—.

The $X_2$—R—$X_2$ segment is preferably a radical derived from a diisocyanate, where each $X_2$, independently of the other, is NHCONH—, —NHCOO— or —OCONH—, in particular —NHCOO— or —OCONH—.

Z is preferably a bond, lower alkylene or —CONH-arylene, in which the —CO— moiety is linked to a CF$_2$ group. Z is particularly preferably lower alkylene, in particular methylene.

q is preferably 0, 1, 1.5 or 2, particularly preferably 0 or 1.5.

The perfluoroalkoxy units OCF$_2$ and OCF$_2$CF$_2$ with the indices x and y in segment (a) can either have a random distribution or be in the form of blocks in a chain. The sum of the indices x+y is preferably a number in the range of 10 to 25, particularly preferably of 10 to 15. The ratio x:y is preferably in the range of 0.5 to 1.5, in particular in the range of 0.7 to 1.1.

A free-radical-polymerizable group $P_1$ is, for example, alkenyl, alkenylaryl or alkenylarylenealkyl having up to 20 carbon atoms. Examples of alkenyl are vinyl, allyl, 1-propen-2-yl, 1-buten-2-, -3- and -4-yl, 2-buten-3-yl, and the isomers of pentenyl, hexenyl, octenyl, decenyl and undecenyl. Examples of alkenylaryl are vinylphenyl, vinylnaphthyl or allylphenyl. An example of alkenylarylenealkyl is o-, m-, or p-vinylbenzyl.

$P_1$ is preferably alkenyl or alkenylaryl having up to 12 carbon atoms, particularly preferably alkenyl having up to 8 carbon atoms, in particular alkenyl having up to 4 carbon atoms.

Y is preferably —COO—, —OCO—, —NHCONH—, —NHCOO—, —OCONH—, NHCO— or —CONH—, particularly preferably —COO—, —OCO—, NHCO— or —CONH—, and in particular, —COO— or —OCO—.

In a preferred embodiment, the indices, m and p, are not simultaneously zero. If p is zero, m is preferably 1.

L is preferably alkylene, arylene, a saturated bivalent cycloaliphatic group having 6 to 20 carbon atoms, arylenealkylene, alkylenearylene, alkylenearylenealkylene or arylenealkylenearylene.

Preferably, L is a divalent radical having up to 12 carbon atoms, particularly preferably a divalent radical having up to 8 carbon atoms. In a preferred embodiment, L is furthermore alkylene or arylene having up to 12 carbon atoms. A particularly preferred embodiment of L is lower alkylene, in particular lower alkylene having up to 4 carbon atoms.

The divalent radical R is, for example, alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

In a preferred embodiment, R is alkylene, arylene, alkylenearylene, arylenealkylene or arylenealkylenearylene having up to 14 carbon atoms or a saturated divalent cycloaliphatic group having 6 to 14 carbon atoms. In a particularly preferred embodiment, R is alkylene or arylene having up to 12 carbon atoms or a saturated bivalent cycloaliphatic group having 6 to 14 carbon atoms.

In a preferred embodiment, R is alkylene or arylene having up to 10 carbon atoms or a saturated bivalent cycloaliphatic group having 6 to 10 carbon atoms.

In a particularly preferred meaning, R is a radical derived from a diisocyanate, for example from hexane 1,6-diisocyanate, 2,2,4-trimethylhexane 1,6-diisocyanate, tetramethylene diisocyanate, phenylene 1,4-diisocyanate, toluene 2,4-diisocyanate, toluene 2,6-dilsocyanate, m-or p-tetramethylxylene diisocyanate, isophorone diisocyanate or cyclohexane 1,4-diisocyanate.

In a preferred meaning, n is an integer from 5 to 70, particularly preferably 10 to 50, in particular 14 to 28.

In a preferred meaning, 80–100%, preferably 85–100%, in particular 90–100%, of the radicals $R_1$, $R_2$, $R_3$ and R4 are, independently of one another, lower alkyl having up to 8 carbon atoms, particularly preferably lower alkyl having up to 4carbon atoms, especially lower alkyl having up to 2 carbon atoms. A further particularly preferred embodiment of $R_1$, $R_2$, $R_3$ and $R_4$ is methyl.

In a preferred meaning, 0–20%, preferably 0–15%, in particular 0–10%, of the radicals $R_1$, $R_2$, $R_3$ and $R_4$ are, independently of one another, lower alkenyl, unsubstituted or lower alkyl- or lower alkoxy-substituted phenyl or cyano (lower alkyl).

Arylene is preferably phenylene or naphthylene, which is unsubstituted or substituted by lower alkyl or lower alkoxy, in particular 1,3-phenylene, 1,4-phenylene or methyl-1,4-phenylene, 1,5-naphthylene or 1,8-naphthylene.

Aryl is a carbocyclic aromatic radical which is unsubstituted or substituted preferably by lower alkyl or lower alkoxy. Examples are phenyl, tolyl, xylyl, methoxyphenyl, t-butoxyphenyl, naphthyl and phenanthryl.

A saturated bivalent cycloaliphatic group is preferably cycloalkylene, for example cyclohexylene or cyclohexylene (lower alkylene), for example cyclohexylenemethylene, which is unsubstituted or substituted by one or more lower alkyl groups, for example methyl groups, for example trimethylcyclohexylenemethylene, for example the bivalent isophorone radical.

For the purposes of the present invention, the term "lower" in connection with radicals and compounds, unless defined otherwise, denotes, in particular, radicals or compounds having up to 8 carbon atoms, preferably having up to 4 carbon atoms.

Lower alkyl has, in particular, up to 8 carbon atoms, preferably up to 4 carbon atoms, and is, for example, methyl, ethyl, propyl, butyl, tert-butyl, pentyl, hexyl or isohexyl.

Alkylene has up to 12 carbon atoms and can be straight-chain or branched. Suitable examples are decylene, octylene, hexylene, pentylene, butylene, propylene, ethylene, methylene, 2-propylene, 2-butylene, 3-pentylene, and the like.

Lower alkylene is alkylene having up to 8 carbon atoms, particularly preferably up to 4 carbon atoms. Particularly preferred meanings of lower alkylene are propylene, ethylene and methylene.

The arylene unit in alkylenearylene or arylenealkylene is preferably phenylene, unsubstituted or substituted by lower alkyl or lower alkoxy, and the alkylene unit therein is preferably lower alkylene, such as methylene or ethylene, in particular methylene. These radicals are therefore preferably phenylenemethylene or methylenephenylene.

Lower alkoxy has, in particular, up to 8 carbon atoms, preferably up to 4 carbon atoms, and is, for example, methoxy, ethoxy, propoxy, butoxy, tert-butoxy or hexyloxy.

Arylenealkylenearylene is preferably phenylene(lower alkylene)phenylene having up to 8, in particular up to 4, carbon atoms in the alkylene unit, for example phenyleneethylenephenylene or phenylenemethylenephenylene.

The macromers of the formula (I) can be prepared by processes known per se, for example as follows:

In a first step, a perfluoropolyalkyl ether derivative of formula (IV):

$$X_3-(E)_k-Z-CF_2-(OCF_2)_x-(OCF_2CF_2)_y-OCF_2-Z-(E)_k-X_3 \quad (IV)$$

in which $X_3$ is —OH, —NH$_2$, —COOH, —COCl, —NCO or —COOR$_5$, where -COOR$_5$ is generally an activated ester in which $R_5$ is alkyl or aryl which is unsubstituted or substituted by halogen or :25 cyano, and the variables Z, E, k, x and y are as defined above, is preferably reacted with two equivalents of a bifunctional radical of formula (V):

$$X_4-R-X_4 \quad (V)$$

in which R is as defined above and $X_4$ is a functional radical which is coreactive with an $X_3$ and is preferably —OH—, —NH$_2$, COOH, —COCl, —COOR$_5$ or —NCO; in the presence or absence of a suitable catalyst, where the reaction of $X_3$ with $X_4$ gives a group $X_2$; after which a reactive derivative of formula (VI):

$$X_4-R-X_2-(E)_k-Z-CF_2-(OCF_2)_x-(OCF_2CF_2)_y-OCF_2-Z-(E)_k-X_2-R-X_4 \quad (VI)$$

is obtained which is then preferably reacted with two equivalents of an α,ω-substituted siloxane of formula (VII):

$$X_3Alk-\underset{R_2}{\overset{R_1}{\underset{|}{\overset{|}{Si}}}}-\left[O\underset{R_4}{\overset{R_3}{\underset{|}{\overset{|}{Si}}}}\right]_n-AlkX_3 \quad (VII)$$

where the variables $R_1$, $R_2$, $R_3$, $R_4$, n, $X_3$ and Alk are as defined above, in the presence or absence of a suitable catalyst, giving a compound of formula (VIII):

$$X_3\text{—Sil—}X_2\text{—R—}X_2\text{—PFPE—}X_2\text{—R—}X_2\text{—Sil—}X_3 \quad \text{(VIII)}$$

in which PFPE is $(E)_k\text{—Z—CF}_2\text{—(OCF}_2)_x\text{—(OCF}_2\text{CF}_2)_y\text{—CF}_2\text{—Z—}(E)_k$, Sil is the siloxane radical

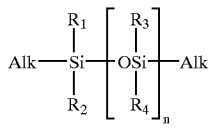

and the other variables are as defined above; after which the reactive intermediate of the formula (VIII) is preferably reacted with two equivalents of a compound of the formula (IXa) or (IXb):

$$P\text{—}(Y)_m\text{—L—}X_4 \quad \text{(IXa)}$$

$$P_1\text{—}Y_2 \quad \text{(IXb)}$$

in the presence or absence of a catalyst, to give the macromer of the formula (I):

$$P_1\text{—}(Y)_m\text{—}(L\text{—}X_1)_p\text{—Q—}(X_1\text{—L})_p\text{—}(Y)_m\text{—}P_1 \quad \text{(I)}$$

in which $Y_2$ is a functional radical which is coreactive with $X_3$ and is preferably —OH, —NH$_2$, —COOH, —COCl, —COOR$_5$, —CONCO or —NCO, and the variables are as defined above, and in which $X_1$ is formed from the reaction of $X_3$ with $X_4$ and Y is formed from the reaction of $Y_2$ with $X_3$.

The starting materials of formula (IV) for the preparation of the perfluoroalkyl ethers are known and many are commercially available. For example, U.S. Pat. No. 3,810,875 and European Patent No. 0211237 (U.S. Pat. No. 4,746,575) describe such compounds. Ausimont, Italy, markets perfluoroalkyl ether dimethanols under the name Fomblin, for example Fomblin ZDOL and Fomblin ZDOL-TX. Further Fomblin derivatives of the formula (IV) are commercially available, including, for example, Fomblin ZDISOC, in which the radical —Z—$X_3$ in the formula (IV) is CONH—C$_6$H$_3$(CH$_3$)—NCO; Fomblin ZDEAL, in which the radical Z—$X_3$ in the formula (IV) is —COOR$_5$; and Fomblin ZDIAC, in which the radical —Z—$X_3$ in the formula (IV) is —COOH.

Bifunctional radicals having a substitution pattern as per formula (V) exist in large numbers and are commercially available. Examples include, without limitation thereto: diisocyanates, such as isophorone diisocyanate and 2,2,4-trimethylhexane 1,6-diisocyanate; diols, such as glycol and cyclohexane-1,2-diol; dicarboxylic acids, such as adipic acid and maleic acid; diamines, such as ethylenediamine and hexamethylenediamine, diesters, such as diethyl phthalate and dibutyl malonate; derivatives containing various functional groups, such as 2-aminoethanol, monomethyl malonate, glycolic acid, salicylic acid, glycine and glycine methyl ester.

Preference is given to bifunctional derivatives of the formula (V) which have different reactivities irrespective of the nature of their functional radicals $X_4$. In the case of identical radicals $X_4$, this is achieved, for example, through different steric requirements in the direct vicinity of a radical $X_4$. Examples thereof are isophorone diisocyanate, 2,2,4-trimethylhexane 1,6-diisocyanate and toluene 2,4-diisocyanate. The advantage of using bifunctional derivatives of formula (V) of different reactivity is that the chain length of polymer Q (number of segments (a), (b) and (c)) is easily adjustable and controllable.

α,ω-substituted siloxanes of formula (VII) are likewise commercially available, for example α, ω-hydroxypropyl-terminated polydimethylsiloxane KF6001 from Shin-Etsu.

The novel compounds can be prepared in the presence or absence of a solvent. It is advantageous to use a substantially inert solvent, i.e., one which does not participate in the reaction. Suitable examples thereof are ethers, such as tetrahydrofuran (THF), diethyl ether, diethylene glycol dimethyl ether or dioxane, halogenated hydrocarbons, such as chloroform or methylene chloride, bipolar aprotic solvents, such as acetonitrile, acetone, dimethylformamide (DMF) or dimethyl sulfoxide (DMSO), hydrocarbons, such as hexane, petroleum ether, toluene or xylene, and furthermore pyridine or N-methylmorpholine.

In the preparation of novel compounds, the reactants are advantageously employed in stoichiometric amounts. The reaction temperature can be, for example, from –30° C. to 150° C., preferably from 0° to room temperature. The reaction times are in the range of about 15 minutes to 7 days, preferably about 12 hours. If necessary, the reaction is carried out under argon or nitrogen as protective gas. In urethane-forming reactions, a suitable catalyst, for example, dibutyltin dilaurate (DBTDL), is advantageously added.

The present Material "B" furthermore relates to a polymer comprising a product of the polymerization of at least one compound of formula (I) as defined above and, if desired, at least one vinylic comonomer (a). In a preferred composition of a novel copolymer, the proportion by weight of a compound of formula (I) is in the range of 100 to 0.5%, in particular in the range of 80 to 10%, preferably in the range of 70 to 30%, based on the total polymer.

In a preferred polymer comprising a product of the polymerization of at least one compound of the formula (I), comonomer (a) is absent and the polymer is a homopolymer.

A comonomer (a) present in the novel polymer can be hydrophilic or hydrophobic or a mixture thereof. Suitable comonomers are, in particular, those which are usually used in the production of contact lenses and biomedical materials. A hydrophobic comonomer (a) is taken to mean a monomer which typically gives a homopolymer which is insoluble in water and can absorb less than 10% by weight of water. Analogously, a hydrophilic comonomer (a) is taken to mean a monomer which typically gives a homopolymer which is soluble in water or can absorb at least 10% by weight of water. Suitable hydrophobic comonomers (a) are, without limitation thereto, $C_1$–$C_{18}$alkyl and $C_3$–$C_{18}$cycloalkyl acrylates and methacrylates, $C_3$–$C_{18}$alkylacrylamides and -methacrylamides, acrylonitrile, methacrylonitrile, vinyl $C_1$–$C_{18}$alkanoates, $C_2$–$C_{18}$alkenes, $C_2$–$C_{18}$haloalkenes, styrene, (lower alkyl)styrene, lower alkyl vinyl ethers, $C_2$–$C_{10}$perfluoroalkyl acrylates and methacrylates and correspondingly partially fluorinated acrylates and methacrylates, $C_3$–$C_{12}$perfluoroalkylethylthiocarbonylaminoethyl acrylates and methacrylates, acryloxy- and methacryloxyalkylsiloxanes, N-vinylcarbazole, $C_1$–$C_{12}$alkyl esters of maleic acid, fumaric acid, itaconic acid, mesaconic acid and the like.

Preference is given, for example, to acrylonitrile, $C_1$–$C_4$alkyl esters of vinylically unsaturated carboxylic acids having 3 to 5 carbon atoms or vinyl esters of carboxylic acids having up to 5 carbon atoms.

Examples of suitable hydrophobic comonomers (a) are methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tristrimethylsilyloxysilylpropyl methacrylate (TRIS), 3-methacryloxy propylpentamethyldisiloxane and bis(methacryloxypropyl) tetramethyldisiloxane.

Preferred examples of hydrophobic comonomers (a) are methyl methacrylate, TRIS and acrylonitrile.

Suitable hydrophilic comonomers (a) are, without this being an exhaustive list, hydroxyl-substituted lower alkyl acrylates and methacrylates, acrylamide, methacrylamide, (lower alkyl)acrylamides and -methacrylamides, ethoxylated acrylates and methacrylates, hydroxyl-substituted (lower alkyl)acrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino(lower alkyl)- (where the term "amino" also includes quaternary ammonium), mono(lower alkylamino)(lower alkyl) and di(lower alkylamino)(lower alkyl) acrylates and methacrylates, allyl alcohol and the like. Preference is given, for example, to N-vinyl-2-yrrolidone, acrylamide, methacrylamide, hydroxyl-substituted lower alkyl acrylates and methacrylates, hydroxy-substituted (lower alkyl) acrylamides and -methacrylamides and vinylically unsaturated carboxylic acids having a total of 3 to 5 carbon atoms.

Examples of suitable hydrophilic comonomers (a) are hydroxyethyl methacrylate (HEMA), hydroxyethyl acrylate, hydroxypropyl acrylate, trimethylammonium 2-hydroxy propylmethacrylate hydrochloride (Blemer® QA, for example from Nippon Oil), dimethylaminoethyl methacrylate (DMAEMA), dimethylaminoethylmethacrylamide, acrylamide, methacrylamide, N,N-dimethylacrylamide (DMA), allyl alcohol, vinylpyridine, glycerol methacrylate, N-(1,1-dimethyl-3-oxobutyl)acrylamide, N-vinyl-2-pyrrolidone (NVP), acrylic acid, methacrylic acid and the like.

Preferred hydrophilic comonomers (a) are trimethylammonium 2-hydroxy propylmethacrylate hydrochloride, 2-hydroxyethyl methacrylate, dimethylaminoethyl methacrylate, trimethylammonium 2-hydroxypropylmethacrylate hydrochloride, N,N-dimethylacrylamide and N-vinyl-2-pyrrolidone.

The novel polymers are synthesized in a manner known per se from the corresponding monomers (the term monomer here also including a macromer according to the definition of the formula (I)) by a polymerization reaction customary to the person skilled in the art. Usually, a mixture of the abovementioned monomers is warmed with addition of a free-radical former. Examples of such free-radical formers are azoisobutyronitrile (AIBN), potassium peroxodisulfate, dibenzoyl peroxide, hydrogen peroxide and sodium percarbonate. If, for example, said compounds are warmed, free radicals form with homolysis, and can then initiate, for example, a polymerization.

A polymerization reaction can particularly preferably be carried out using a photoinitiator. In this case, the term photopolymerization is used. In the photopolymerization, it is appropriate to add a photoinitiator which can initiate free-radical polymerization and/or crosslinking by using light. Examples thereof are customary to the person skilled in the art; suitable photoinitiators are, in particular, benzoin methyl ether, 1-hydroxycyclohexylphenyl ketone, Darocur and Irgacur products, preferably Darocur® 1173 and Irgacur® 2959. Also suitable are reactive photoinitiators, which can be incorporated, for example, into a macromer, or can be used as a specific comonomer (a). Examples thereof are given in European Patent No. 0632329. The photopolymerization can then be initiated by actinic radiation, for example light, in particular UV light having a suitable wavelength. The spectral requirements can, if necessary, be controlled appropriately by addition of suitable photosensitizers.

A polymerization can be carried out in the presence or absence of a solvent. Suitable solvents are in principle all solvents which dissolve the monomers used, for example water, alcohols, such as lower alkanols, for example ethanol or methanol, furthermore carboxamides, such as dimethylformamide, dipolar aprotic solvents, such as dimethyl sulfoxide or methyl ethyl ketone, ketones, for example acetone or cyclohexanone, hydrocarbons, for example toluene, ethers, for example THF, dimethoxyethane or dioxane, halogenated hydrocarbons, for example trichloroethane, and also mixtures of suitable solvents, for example mixtures of water and an alcohol, for example a water/ethanol or water/methanol mixture.

A polymer network can, if desired, be reinforced by addition of a crosslinking agent, for example a polyunsaturated comonomer (b). In this case, the term crosslinked polymers is used. The invention, therefore, furthermore relates to a crosslinked polymer comprising the product of the polymerization of a macromer of the formula (I), if desired with at least one vinylic comonomer (a) and with at least one comonomer (b).

Examples of typical comonomers (b) are allyl (meth)acrylate, lower alkylene glycol di(meth)acrylate, poly(lower alkylene) glycol di(meth)acrylate, lower alkylene di(meth)acrylate, divinyl ether, divinyl sulfone, di- and trivinylbenzene, trimethylolpropane tri(meth)acrylate, pentaerythritol tetra(meth)acrylate, bisphenol A di(meth)acrylate, methylenebis(meth)acrylamide, triallyl phthalate and diallyl phthalate.

The amount of comonomer (b) used is expressed in a proportion by weight based on the total polymer and is in the range from 20 to 0.05%, in particular in the range from 10 to 0.1%, preferably in the range from 2 to 0.1%.

3. Material "C"

Material "C" polymers are formed by polymerizing polymerizable macromers which contain free hydroxyl groups. Macromers which are built up, for example, from an aminoalkylated polysiloxane which is derivatized with at least one polyol component containing an unsaturated polymerizable side chain are disclosed. Polymers can be prepared on the one hand from the macromers according to the invention by homopolymerization. The macromers mentioned furthermore can be mixed and polymerized with one or more hydrophilic and/or hydrophobic comonomers. A special property of the macromers according to the invention is that they function as the element which controls microphase separation between selected hydrophilic and hydrophobic components in a crosslinked end product. The hydrophilic/hydrophobic microphase separation is in the region of less than 300 nm. The macromers are preferably crosslinked at the phase boundaries between, for example, an acrylate comonomer on the one hand and an unsaturated polymerizable side chain of polyols bonded to polysiloxane on the other hand, by covalent bonds and additionally by reversible physical interactions, for example hydrogen bridges. These are formed, for example, by numerous amide or urethane groups. The continuous siloxane phase which exists in the phase composite has the effect of producing a surprisingly high permeability to oxygen.

The present embodiment of the invention relates to a macromer comprising at least one segment of the formula (I):

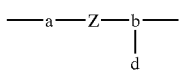
(I)

in which
(a) is a polysiloxane segment,
(b) is a polyol segment which contains at least 4 C atoms, Z is a segment (c) or a group $X_1$,
(c) is defined as $X_2$—R—$X_2$, wherein
R is a bivalent radical of an organic compound having up to 20 C atoms and
each $X_2$ independently of the other is a bivalent radical which contains at least one carbonyl group,
$X_1$ is defined as $X_2$, and
(d) is a radical of the formula (II):

$$X_3\text{—}L\text{—}(Y)_k\text{—}P_1 \quad (II)$$

in which
$P_1$ is a group which can be polymerized by free radicals;
Y and $X_3$ independently of one another are a bivalent radical which contains at least one carbonyl group;
k is 0 or 1; and
L is a bond or a divalent radical having up to 20 C atoms of an organic compound.

A polysiloxane segment (a) is derived from a compound of the formula (III):

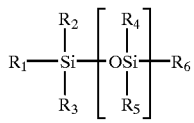

in which
n is an integer from 5 to 500;
99.8–25% of the radicals $R_1$, $R_2$, $R_3$, $R_4$, $R_5$ and $R_6$ independently of one another are alkyl and 0.2–75% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk—NH—alk—NH, or alk—$(OCH_2)_m$—$(OCH_2)p$—$OR_7$,
$R_7$ is hydrogen or lower alkyl, alk is alkylene, and
m and p independently of one another are an integer from 0 to 10, one molecule containing at least one primary amino or hydroxyl group.

The alkylenoxy groups —$(OCH_2CH_2)_m$ and —$(OCH_2)_p$ in the siloxane of the formula (III) are either distributed randomly in a ligand alk—$(OCH_2CH_2)_m$—$(OCH_2)_p$—$OR_7$ or are distributed as blocks in a chain. A polysiloxane segment (a) is linked a total of 1–50 times, preferably 2–30 times, and in particular 4–10 times, via a group Z with a segment (b) or another segment (a), Z in an a-Z-a sequence always being a segment (c). The linkage site in a segment (a) with a group Z is an amino or hydroxyl group reduced by one hydrogen.

In a preferred embodiment, a polysiloxane segment is derived from a compound of the formula (III) in which the radicals $R_1$, $R_2$, $R_3$, $R_4$, $R_5$ and $R_6$ are a total of 1–50 times, more preferably 2–30 times, and in particular 4–10 times, independently either terminally or pendently aminoalkyl or hydroxyalkyl, the other variables being as defined above.

In a preferred embodiment, a polysiloxane segment is derived from a compound of the formula (III) in which 95–29% of the radicals $R_1$, $R_2$, $R_3$, $R_4$, $R_5$ and $R_6$ independently of one another are alkyl and 5–71% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk-NH-alk-$NH_2$ or alk—$(OCH_2CH_2)_m$ $(OCH_2)_p$—$OR_7$, and in which the variables are as defined above.

In a preferred meaning, n is an integer from 5 to 400, more preferably 10 to 250 and particularly preferably 12 to 125.

In a preferred meaning, the two terminal radicals $R_1$ and $R_6$ are aminoalkyl or hydroxyalkyl, the other variables being as defined above. P In another preferred meaning, the radicals $R_4$ and $R_5$ are 1–50 times, more preferably 2–30 times and in particular 4–10 times pendently aminoalkyl or hydroxyalkyl and the other variables are as defined above.

In another preferred meaning, the radicals $R_1$, $R_2$, $R_3$, $R_4$, $R_5$ and $R_6$ are a total of 1–50 times, more preferably 2–30 times and in particular 4–10 times, independently both terminally and pendently aminoalkyl or hydroxyalkyl and the other variables are as defined above.

If Z is $X_1$, $X_1$ is a bivalent group which contains at least one carbonyl group. A carbonyl group mentioned is flanked in any manner, if appropriate, by —O—, —CONH—, —NHCO— or —NH—.

Examples of bivalent groups Z are typically carbonyls, esters, amides, urethanes, ureas or carbonates.

$X_1$ is preferably an ester, amide, urethane or urea group, in particular an ester or amide group.

$X_2$ is defined in the same way as $X_1$ and is preferably an ester, amide, urethane, carbonate or urea group, more preferably an ester, amide, urethane or urea group and in particular an amide, urethane or urea group.

If Z in formula (I) is $X_1$, a polyol segment b is preferably understood as meaning a polyol derived from a carbohydrate, carbohydrate monolactone or carbohydrate dilactone. A carbohydrate is understood as meaning a mono-, di-, tri-, tetra-, oligo- or polysaccharide. A carbohydrate lactone is understood as meaning the lactone of an aldonic or uronic acid. An aldonic or uronic acid is, for example, a carboxylic acid formed by oxidation of a mono-, di-, tri- tetra-, oligo- or polysaccharide. Examples of aldonic acid lactones are gluconolactone, galactonolactone, lactobionolactone or maltoheptaonolactone; examples of uronic acid lactones are glucuronic acid lactone, mannuronic acid lactone or iduronic acid lactone. An example of a carbohydrate dilactone is D-glucaro-1,4:6,3-dilactone.

A carbohydrate lactone reacts, for example, with a primary amino group or a hydroxyl group of segment (a) to form a covalent amide or ester bond of the type $X_1$. Such linkages are the constituent of a further preferred embodiment of macromers according to the invention. Such macromers have an alternating distribution of segments of type (a) and (b) which are interrupted by $X_1$.

This embodiment of the invention preferably relates to a macromer of the formula (IV):

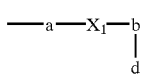
(IV)

in which the variables are as defined above.

An embodiment of the invention furthermore preferably relates to a macromer according to formula (V):

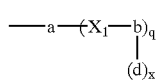
(V)

in which
the polysiloxane segment (a) contains q pendent ligands
x is 0, 1 or 2,
q has an average numerical value of 1–20, preferably 1–10, and in particular 1–5, and
the segments (b) in a macromer according to the formula (V) are linked in total (per molecule) with up to 20, preferably with up to 15, and in particular with up to 6 polymerizable segments (d).

An embodiment of the invention furthermore preferably relates to a macromer according to formula (VI):

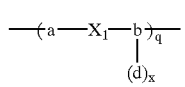
(VI)

in which
a linear sequence is present,
x is 0, 1 or 2,
q has an average numerical value of 1–20, preferably 1–10, and in particular 1–5, and
the segments (b) in a macromer according to the formula (VI) are linked in total (per molecule) with up to 20, preferably with up to 15, and in particular with up to 6 polymerizable segments (d).

An embodiment of the invention furthermore very preferably relates to a macromer according to formula (VII):

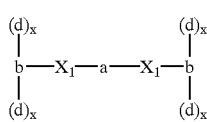
(VII)

in which x is 0, 1 or 2, and
the average number of segments (d) per molecule of the formula (VII) is preferably in the range from 2 to 5, and very preferably is in the range from 3 to 4.

A polyol segment (b) is derived from a polyol which carries no lactone group if the group Z is a segment (c). Examples of such polyols are a 1,2-polyol, for example the reduced monosaccharides, for example mannitol, glucitol, sorbitol or iditol, a 1,3-polyol, for example polyvinyl alcohol (PVA), which is derived from partly or completely hydrolysed polyvinyl acetate, and furthermore aminoterminal PVA telomers, aminopolyols, aminocyclodextrins, aminomono-, -di-, -tri-, -oligo- or -polysaccharides or cyclodextrin derivatives, for example hydroxypropylcyclodextrin. An abovementioned carbohydrate dilactone can be reacted, for example, with preferably 2 equivalents of an amino-terminal PVA telomer to give a polyol macromer which carries, in the central part, the carbohydrate compound derived from the dilactone. Such polyols of this composition are likewise understood to be a suitable polyol.

As illustrated in formula (I), a segment (b) carries at least one vinylic polymerizable segment (d), a linkage of a segment (d) via the bivalent radical $X_3$ thereof to an amino or hydroxyl group, of a segment (b), reduced by a hydrogen atom being intended.

A vinylic polymerizable segment (d) is incorporated either terminally or pendently preferably 1–20 times, more preferably 2–15 times, and in particular 2–6 times, per macromer molecule according to the invention.

A vinylic polymerizable segment (d) is incorporated terminally and also pendently as desired (as a terminal/pendent mixture) preferably 1–20 times, more preferably 2–15 times and in particular 2–6 times, per macromer molecule according to the invention.

A group $P_1$ which can be polymerized by free radicals is, for example, alkenyl, alkenylaryl or alkenylarylenealkyl having up to 20 C atoms. Examples of alkenyl are vinyl, allyl, 1-propen-2-yl, 1-buten-2- or -3- or -4-yl, 2-buten-3-yl and the isomers of pentenyl, hexenyl, octenyl, decenyl or undecenyl. Examples of alkenylaryl are vinylphenyl, vinylnaphthyl or allylphenyl. An example of alkenylarylenealkyl is vinylbenzyl.

$P_1$ is preferably alkenyl or alkenylaryl having up to 12 C atoms, more preferably alkenyl having up to 8 C atoms and in particular alkenyl having up to 4 C atoms.

L is preferably alkylene, arylene, a saturated bivalent cycloaliphatic group having 6 to 20 carbon atoms, arylenealkylene, alkylenearylene, alkylenearylenealkylene or arylenealkylenearylene. In a preferred meaning, L furthermore is preferably a bond.

In a preferred meaning, L is a divalent radical having up to 12 C atoms, and more preferably a divalent radical having up to 8 C atoms. In a preferred meaning, L furthermore is alkylene or arylene having up to 12 C atoms. A very preferred meaning of L is lower alkylene, in particular lower alkylene having up to 4C atoms.

Y is preferably a carbonyl, ester, amide or urethane group, in particular a carbonyl, ester or amide group, and very preferably a carbonyl group.

In another preferred meaning, Y is absent, i.e., k is 0.

In a preferred meaning, $X_3$ is a urethane, urea, ester, amide or carbonate group, more preferably a urethane, urea, ester or amide group, and in particular a urethane or urea group. A vinylic polymerizable segment (d) is derived, for example, from acrylic acid, methacrylic acid, methacryloyl chloride, 2-isocyanatoethyl methacrylate (IEM), allyl isocyanate, vinyl isocyanate, the isomeric vinylbenzyl isocyanates or adducts of hydroxyethyl methacrylate (HEMA) and 2,4-tolylene diisocyanate (TDI) or isophorone diisocyanate (IPDI), in particular the 1:1 adduct. The invention furthermore preferably relates to a macromer in which a segment (d) is incorporated either terminally or pendently or as a terminal/pendent mixture 5 times. The invention furthermore preferably relates to a macromer in which a segment (d) is incorporated terminally 5 times.

The diradical R is, for example, alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

In a preferred meaning, R is alkylene, arylene, alkylenearylene, arylenealkylene or arylenealkylenearylene having up to 14 carbon atoms or a saturated bivalent cycloaliphatic group having 6 to 14 carbon atoms.

In a preferred meaning, R is alkylene, arylene, alkylenearylene or arylenealkylene having up to 14 carbon atoms, or a saturated bivalent cycloaliphatic group having 6 to 14 carbon atoms. In a preferred meaning, R is alkylene or arylene having up to 12 carbon atoms, or a saturated bivalent cycloaliphatic group having 6 to 14 carbon atoms.

In a preferred meaning, R is alkylene or arylene having up to 10 carbon atoms, or is a saturated bivalent cycloaliphatic group having 6 to 10 carbon atoms.

In a very preferred meaning, a segment (c) is derived from a diisocyanate, for example from hexane 1,6-diisocyanate, 2,2,4-trimethylhexane 1,6-diisocyanate, tetramethylene diisocyanate, phenylene 1,4-diisocyanate, toluene 2,4-diisocyanate, toluene 2,6-diisocyanate, m- or p-tetramethylxylene diisocyanate, isophorone diisocyanate or cyclohexane 1,4-diisocyanate.

A preferred embodiment of segment (c) is furthermore derived from a diisocyanate in which the isocyanate groups have different reactivities. The different reactivity is influenced, in particular, by the spatial requirements and/or electron density in the neighbourhood of an isocyanate group.

The average molecular weight of a macromer according to the invention is preferably in the range from about 300 to about 30,000, very preferably in the range from about 500 to about 20,000, more preferably in the range from about 800 to about 12,000, and particularly preferably to in the range from about 1000 to about 10,000.

A preferred embodiment of the macromer has a segment sequence of the formula (VIII):

b-Z-a-{c-a})$_r$-(Z-b)$_t$ (VIII)

in which
r is an integer from 1 to 10, preferably from 1 to 7, and in particular from 1 to 3;
t is 0 or 1, and preferably 1;
a linear (c-a) chain which may or may not be terminated by a segment (b) is present (t=1); and
the above preferences apply to the total number of segments (d), which are preferably bonded to a segment (b).

A preferred embodiment of the macromer has a segment sequence of formula (IX):

b-Z-a-{c-a-(Z-b)$_t$}$_r$ (IX)

in which
the sequence (c-a)-(Z-b)t hangs pendently r times on the segment (a) and may or may not be terminated by a segment (b);
r is an integer from 1 to 10, preferably from 1 to 7, and in particular from 1 to 3;
t is 0 or 1, and is preferably 1;
Z is a segment (c) or a group $X_1$; and
the above preferences apply to the total number of segments (d), which are preferably bonded to a segment (b).

Another preferred embodiment of the macromer has a segment sequence of formula (X):

b-c-{a-c}$_s$-B (X)

in which
s is an integer from 1 to 10, preferably from 1 to 7, and in particular from 1 to 3;
B is a segment (a) or (b); and
the above preferences apply to the number of segments (d), which are bonded to a segment (b).

Another preferred embodiment of the macromer has a segment sequence of the formula (XI):

B-(c-b)$_s$-Z-a-(b)$_t$ (XI)

in which
the structures are linear,
s is an integer from 1 to 10, preferably from 1 to 7, and in particular from 1 to 3;

B is a segment (a) or (b);
t is 0 or 1, and
the above preferences apply to the number of segments (d), which are bonded to a segment (b).

The ratio of the number of segments (a) and (b) in a macromer according to the Material "C" embodiment of the invention is preferably in a range of (a):(b)=3:4, 2:3, 1:2, 1:1, 1:3 or 1:4. The total sum of segments (a) and (b) or, where appropriate, (a) and (b) and (c) is in a range from 2 to 50, preferably 3 to 30, and in particular in the range from 3 to 12.

Alkyl has up to 20 carbon atoms and can be straight-chain or branched. Suitable examples include dodecyl, octyl, hexyl, pentyl, butyl, propyl, ethyl, methyl, 2-propyl, 2-butyl or 3-pentyl.

Arylene is preferably phenylene or naphthylene, which is unsubstituted or substituted by lower alkyl or lower alkoxy, in particular 1,3-phenylene, 1,4-phenylene or methyl-1,4-phenylene; or 1,5-naphthylene or 1,8-naphthylene.

Aryl is a carbocyclic aromatic radical, which is unsubstituted or substituted by preferably lower alkyl or lower alkoxy. Examples are phenyl, toluyl, xylyl, methoxyphenyl, t-butoxyphenyl, naphthyl or phenanthryl.

A saturated bivalent cycloaliphatic group is preferably cycloalkylene, for example cyclohexylene or cyclohexylene-lower alkylene, for example cyclohexylenemethylene, which is unsubstituted or substituted by one or more lower alkyl groups, for example methyl groups, for example trimethylcyclohexylenemethylene, for example the bivalent isophorone radical. The term "lower" in the context of this invention in connection with radicals and compounds, unless defined otherwise, means, in particular, radicals or compounds having up to 8 carbon atoms, preferably having up to 4 carbon atoms.

Lower alkyl has, in particular, up to 8 carbon atoms, preferably up to 4 carbon atoms, and is, for example, methyl, ethyl, propyl, butyl, tert-butyl, pentyl, hexyl or isohexyl.

Alkylene has up to 12 carbon atoms and can be straight-chain or branched. Suitable examples include decylene, octylene, hexylene, pentylene, butylene, propylene, ethylene, methylene, 2-propylene, 2-butylene or 3-pentylene.

Lower alkylene is alkylene having up to 8, and particularly preferably having up to 4carbon atoms. Particularly preferred examples of lower alkylenes are propylene, ethylene and methylene.

The arylene unit of alkylenearylene or arylenealkylene is preferably phenylene, which is unsubstituted or substituted by lower alkyl or lower alkoxy, and the alkylene unit of this is preferably lower alkylene, such as methylene or ethylene, in particular methylene. Such radicals are therefore preferably phenylenemethylene or methylenephenylene.

Lower alkoxy has, in particular, up to 8 carbon atoms, preferably up to 4 carbon atoms, and is, for example, methoxy, ethoxy, propoxy, butoxy, tert-butoxy or hexyloxy.

Partly fluorinated alkyl is understood as meaning alkyl in which up to 90%, preferably up to 70%, and in particular up to 50%, of the hydrogens are replaced by fluorine.

Arylenealkylenearylene is preferably phenylene-lower alkylene-phenylene having up to 8, and in particular having up to 4 carbon atoms in the alkylene unit, for example phenylenethylenephenylene or phenylenemethylenephenylene.

A monosaccharide in the context of the present invention is understood as meaning an aldopentose, aldohexose, aldotetrose, ketopentose or ketohexose.

Examples of an aldopentose are D-ribose, D-arabinose, D-xylose or D-lyose; examples of an aldohexose are D-allose, D-altrose, D-glucose, D-mannose, D-gulose, D-idose, D-galactose, D-talose, L-fucose or L-rhamnose; examples of a ketopentose are D-ribulose or D-xylulose; examples of a tetrose are D-erythrose or threose; and examples of a ketohexose are D-psicose, D-fructose, D-sorbose or D-tagatose. Examples of a disaccharide are trehalose, maltose, somaltose, cellobiose, gentiobiose, saccharose, lactose, chitobiose, N,N-diacetylchitobiose, palatinose or sucrose. Raffinose, panose or maltotriose may be mentioned as an example of a trisaccharide. Examples of an oligosaccharide are maltotetraose, maltohexaose, chitoheptaose and furthermore cyclic oligosaccharides, such as cyclodextrins.

Cyclodextrins contain 6 to 8 identical units of α-1,4-glucose. Some examples are α-, β- and γ-cyclodextrin, derivatives of such cyclodextrins, for example hydroxypropylcyclodextrins, and branched cyclodextrins.

The macromers according to this embodiment of invention can be prepared by processes known per se, for example as follows.

In a first step, a polysiloxane containing at least one primary amino- or hydroxyalkyl group is reacted with a carbohydrate lactone, an amide or ester bond being formed and a compound of the formula (XIIa) or (XIIb) being formed:

$$(a\text{-}Z\text{-}b)_q \tag{XIIa}$$

$$a\text{-}(Z\text{-}b)q \tag{XIIb}$$

in which the variables are as defined above and Z is a group XI, after which the compound (XII) is reacted with an unsaturated polymerizable compound of the formula (XII):

$$X_4\text{-}L\text{-}(Y)_k\text{-}P_1 \tag{XII}$$

in which $X_4$ is a group which is coreactive with a hydroxyl or amino group of segment (b), an $X_3$ group of a segment (d) according to formula (II) being formed from such a reaction, where $X_4$ is preferably —COOH, —COOR$_{10}$, —COCl or —NCO, in which $R_{10}$ is alkyl, or is aryl which is unsubstituted or substituted by lower alkyl or lower alkoxy, and the other variables are as defined above, after which a macromer according to the formula (IV) or (V) is formed

(IV)

(V)

in which the segments (d) are incorporated terminally or pendently.

Another process starts from a polysiloxane (a) which contains terminal primary amino- or hydroxyalkyl groups and is reacted with a carbohydrate dilactone to form linear structures of the formula (XIV):

(XIV)

in which the variables are as defined and preferred above, after which a compound of the formula (XIV) is reacted with a compound of the formula (XIII) analogously to the above process to give a macromer of the formula (VI):

(VI)

in which the variables are as defined and preferred above.

Another process starts from a polysiloxane (a) which contains terminal primary amino- or hydroxyalkyl groups and is initially reacted with a bifunctional compound of the formula (XV):

$$X_4\text{—}R\text{—}X_4 \tag{XV}$$

in which $X_4$ is a group which is coreactive with a hydroxyl or amino group of segment (a), an $X_2$ group of a segment (c) being formed from such a reaction, where $X_4$ is preferably —COOH, —COOR$_{10}$, —COCl or —NCO, in which $R_{10}$ is alkyl, or aryl which is unsubstituted or substituted by lower alkyl or lower alkoxy, and R is as defined above, after which this intermediate is reacted with a polyol which carries no lactone group to give a compound of the formula (XVI):

$$b\text{-}c\text{-}\{a\text{-}c\}_s\text{-}b \tag{XVI}$$

in which the variables are as defined and preferred above, after which the compound of the formula (XVI) is reacted with a compound of the formula (XIII) to give a macromer of the formula (X):

$$b\text{-}c\text{-}\{a\text{-}c\}_2\text{—}B \tag{X}$$

in which s is an integer from 1 to 10, preferably from 1 to 7, and in particular from 1 to 3; B is a segment (a) or (b); and the above preferences apply to the number of segments (d) which are bonded to a segment (b).

Another process starts from a bifunctional compound of the formula (XV):

$$X_4\text{—}R\text{—}X_4 \tag{XV}$$

in which is reacted with an excess of polysiloxane (a) to give an -a-(c-a)$_r$- sequence, in which the above meanings apply, after which, in a second step, the intermediate is reacted with a polyol which carries no lactone to give a compound of the formula (XVII):

$$b\text{-}Z\text{-}a\text{-}\{c\text{-}a\}_r\text{-}Z\text{-}b \tag{XVII}$$

after which the compound (XVII) is reacted with the compound (XIII) to give a macromer of the formula (VIII):

$$b\text{-}Z\text{-}a\text{-}\{c\text{-}a\}_r\text{-}(Z\text{-}b)_t \tag{VIII}$$

in which r is an integer from 1 to 10, preferably from 1 to 7, and in particular from 1 to 3; t is 0 or 1, and is preferably 1; in which a linear (c-a) chain, which may or may not be terminated by a segment (b), is present (t=1); and the above preferences apply to the total number of segments (d), which are preferably bonded to a segment (b).

Another process starts from a carbohydrate lactone which is reacted in a first step with a compound of the formula (XIII), the lactone function being retained, after which the intermediate is reacted with a polysiloxane containing at least one amino or hydroxyl group to give a compound of the formula (IV) or (V):

$$a\text{—}X_1\text{—}b \atop | \atop d \qquad (IV)$$

$$a\text{—}(X_1\text{—}b)_q\text{—} \atop | \atop (d)_x \qquad (V)$$

in which q is typically 1 or 2, and in which the above meanings and preferences otherwise apply, and the segments (d) are incorporated terminally or pendently.

The present embodiment of the invention furthermore relates to the intermediates which are novel and which occur during synthesis of the macromers according to the invention.

The invention therefore furthermore relates to a compound of the formula (XIIa):

$$(a\text{-}Z\text{-}b)_q \qquad (XIIa)$$

in which q is greater than 1,
(a) is derived from a polysiloxane as defined by formula (I) above and
(b) is derived from a carbohydrate dilactone.

An embodiment of the invention furthermore relates to a compound of the formula (XIIb):

$$a\text{-}(Z\text{-}b)_q \qquad (XIIb)$$

in which Z, (b) and q are as defined and preferred above, but with the proviso that a segment (a) is derived from a compound of the formula (III):

$$R_1\text{—}\underset{R_3}{\overset{R_2}{\underset{|}{\overset{|}{Si}}}}\text{—}\left[\underset{R_5}{\overset{R_4}{\underset{|}{\overset{|}{OSi}}}}\right]_n\text{—}R_6 \qquad (III)$$

in which n is an integer from 5 to 500;
99.8–25% of the radicals $R_1$, $R_2$, $R_3$, $R_4$, $R_5$ and $R_6$ independently of one another are alkyl and
0.2–75% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk-NH-Alk-$NH_2$ or alk—$(OCH_2CH_2)_m$—$(OCH_2)_p$—$OR_7$ in which $R_7$ is hydrogen or lower alkyl, alk is alkylene and
m and p independently of one another are an integer from 0 to 10, one molecule containing at least one primary amino or hydroxyl group and at least one partly fluorinated alkyl group.

The invention furthermore relates to a compound of the formula (XVI):

$$b\text{-}c\text{-}\{a\text{-}c\}_s\text{-}b \qquad (XVI)$$

in which a segment (b) is derived from a polyol which carries no lactone and the other variables are as defined and preferred above.

An embodiment of the invention furthermore relates to a compound of the formula (XVII):

$$b\text{-}Z\text{-}a\text{-}\{c\text{-}a\}_r\text{-}Z\text{-}b \qquad (XVII)$$

in which a segment (b) is derived from a polyol which carries no lactone and the other variables are as defined and preferred above.

A siloxane (a) containing at least one primary amino or hydroxyl group is, for example, commercially obtainable. Examples are KF-6002, KF-8003, X-22-161C (Shin Etsu) or GP4 (Genesee). Other siloxanes can be synthesized with the aid of published processes.

A polyol (b) required for the synthesis is as a rule commercially obtainable. Examples are gluconolactone or lactobionolactone. Otherwise, they can be synthesized with the aid of a published process.

The compounds according to the invention can be prepared in the presence or absence of a solvent. A solvent which is largely inert, i.e., does not participate in the reaction, is advantageously used. Suitable examples of these are ethers, such as tetrahydrofuran (THF), 1,2-dimethoxyethane, diethylene glycol dimethyl ether or dioxane, halogenated hydrocarbons, such as chloroform or methylene chloride, bipolar aprotic solvents, such as acetonitrile, acetone, dimethylformamide (DMF) or dimethyl sulfoxide (DMSO), hydrocarbons, such as toluene or xylene, and furthermore pyridine or N-methylmorpholine.

The reactants are advantageously employed in stoichiometric amounts for the preparation of the compounds according to the invention. The reaction temperature can be, for example, from –30° C. to 50° C. The range from 0° C. to 40° C. is a preferred temperature range. The reaction times here are in the range from about 15 minutes to 7 days, preferably in the region of about 12 hours. If necessary, the reaction is carried out under argon or nitrogen as an inert gas. A suitable catalyst is advantageously added for urethane-forming reactions, for example dibutyltin dilaurate (DBTDL).

The present invention furthermore relates to a polymer comprising a polymerization product of at least one macromer according to the invention as defined above and, if appropriate, at least one vinylic comonomer (a).

The preferred composition of a polymer according to the invention comprises a weight content, with respect to the total polymer, of a macromer according to the invention in the range from 100 to 0.5%, in particular in the range from 80 to 10%, and preferably in the range from 70 to 30%.

In a preferred polymer comprising a polymerization product of at least one macromer according to the invention, comonomer (a) is absent and the polymer is preferably a homopolymer.

A comonomer (a) which is contained in a polymer according to the invention can by hydrophilic or hydrophobic or a mixture of both. Suitable comonomers include, in particular, those which are usually used for the preparation of contact lenses and biomedical materials. A hydrophobic comonomer (a) is understood as meaning monomers which typically give, as a homopolymer, polymers which are water-insoluble and can absorb less than 10% by weight of water.

Analogously, a hydrophilic comonomer (a) is understood as meaning a monomer which typically gives, as a homopolymer, a polymer which is water-soluble or can absorb at least 10% by weight of water.

Suitable hydrophobic comonomers (a) include, without this list being exhaustive, $C_1$–$C_{18}$alkyl and $C_3$–$C_{18}$cycloalkyl acrylates and methacrylates, $C_3$–$C_{18}$alkylacrylamides and -methacrylamides, acrylonitrile, methacrylonitrile, vinyl $C_1$–$C_{18}$alkanoates, $C_2$–$C_{18}$alkenes, $C_2$–$C_{18}$haloalkenes, styrene, lower alkyl styrene, lower alkyl vinyl ethers, $C_2$–$C_{10}$perfluoroalkyl acrylates and methacrylates or correspondingly partly fluorinated acrylates and methacrylates, $C_3$–$C_{12}$perfluoroalkyl-ethyl-thiocarbonylaminoethyl acrylates and methacrylates, acryloxy- and methacryloxy-alkylsiloxanes, N-vinylcarbazole and $C_1$–$C_{12}$alkyl esters of maleic acid, fumaric acid, itaconic acid, mesaconic acid and the like. Preferred comonomers are, for example, acrylonitrile, $C_1$–$C_4$alkyl esters of vinylically unsaturated carboxylic acids having 3 to 5 carbon atoms, or vinyl esters of carboxylic acids having up to 5 carbon atoms.

Examples of suitable hydrophobic comonomers (a) include methyl acrylate, ethyl acrylate, propyl acrylate, isopropyl acrylate, isobutyl acrylate (IBA), isooctyl acrylate (OA), isodecyl acrylate (DA), cyclohexyl acrylate, 2-ethylhexyl acrylate (EHA), methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl (meth)acrylate (HFBMA and HFBA), tris-trimethylsilyloxy-silyl-propyl methacrylate (TRIS), 3-methacryloxypropylpentamethyldisiloxane and bis(methacryloxypropyl) tetramethyldisiloxane. Preferred examples of hydrophobic comonomers (a) are methyl methacrylate, IBA, HFBA, HFBMA, OA, EHA, DA, TRIS and acrylonitrile.

Suitable hydrophilic comonomers (a) include, without this list being conclusive, hydroxyl-substituted lower alkyl acrylates and methacrylates, acrylamide, methacrylamide, lower alkylacrylamides and -methacrylamides, ethoxylated acrylates and methacrylates, hydroxyl-substituted lower alkylacrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino-lower alkyl (where the term "amino" also includes quaternary ammonium), mono-lower alkylamino-lower alkyl and di-lower alkylamino-lower alkyl acrylates and methacrylates, allyl alcohol and the like. Preferred comonomers are, for example, N-vinyl-2-pyrrolidone, acrylamide, methacrylamide, hydroxyl-substituted lower alkyl acrylates and methacrylates, hydroxyl-substituted lower alkylacrylamides and -methacrylamides and vinylically unsaturated carboxylic acids having a total of 3 to 5 carbon atoms.

Examples of suitable hydrophilic comonomers (a) include hydroxyethyl methacrylate (HEMA), hydroxyethyl acrylate, hydroxypropyl acrylate, trimethylammonium 2-hydroxypropyl methacrylate hydrochloride (Blemer®QA, for example from Nippon Oil), dimethylaminoethyl methacrylate (DMAEMA), dimethylaminoethyl methacrylamide, acrylamide, methacrylamide, N,N-dimethylacrylamide (DMA), allyl alcohol, vinylpyridine, glycerol methacrylate, N-(1,1-dimethyl-3-oxobutyl)acrylamide, N-vinyl-2-pyrrolidone (NVP), acrylic acid, methacrylic acid and the like.

Preferred hydrophilic comonomers (a) are 2-hydroxyethyl methacrylate, dimethylaminoethyl methacrylate, trimethylammonium-2-hydroxypropyl methacrylate hydrochloride, N,N-dimethylacrylamide and N-vinyl-2-pyrrolidone.

The polymers according to the invention are built up in a manner known per se from the corresponding monomers (the term monomers here also including a macromer according to the invention) by a polymerization reaction with which the expert is familiar. Usually, a mixture of the abovementioned monomers is heated, with the addition of an agent which forms free radicals. Such an agent which forms free radicals is, for example, azoisobutyronitrile (AIBN), potassium peroxodisulfate, dibenzoyl peroxide, hydrogen peroxide or sodium percarbonate. If the compounds mentioned are heated, for example, free radicals are then formed, by homolysis, and can then, for example, initiate a polymerization.

A polymerization reaction can particularly preferably be carried out using a photoinitiator. Photopolymerization is the term used in this case. For photopolymerization, a photoinitiator which can initiate free radical polymerization and/or crosslinking by the use of light is suitably added. Examples of this are familiar to the expert, and specifically, suitable photoinitiators are benzoin methyl ether, 1-hydroxycyclohexyl phenyl ketone and Darocur and Irgacur types, preferably Darocur 1173® and Darocur 2959®. Reactive photoinitiators which can be incorporated, for example, into a macromer or can be used as a special comonomer (a) are also suitable. Examples of these are to be found in EP 632 329. The photopolymerization can then be triggered off by actinic radiation, for example light, in particular UV light of a suitable wavelength. The spectral requirements can be controlled accordingly, if appropriate, by addition of suitable photosensitizers.

Polymerization can be carried out in the presence or absence of a solvent. Suitable solvents are in principle all solvents which dissolve the monomers used, for example water, alcohols, such as lower alkanols, for example ethanol or methanol, and furthermore carboxylic acid amides, such as dimethylformamide, dipolar aprotic solvents, such as dimethyl sulfoxide or methyl ethyl ketone, ketones, for example acteone or cyclohexanone, hydrocarbons, for example toluene, ethers, for example THF, dimethoxyethane or dioxane, and halogenated hydrocarbons, for example trichloroethane, and also mixtures of suitable solvents, for example mixtures of water with an alcohol, for example a water/ethanol or a water/methanol mixture.

If appropriate, a polymer network can be intensified by addition of a so-called crosslinking agent, for example a polyunsaturated comonomer (b). The invention furthermore relates to a polymer comprising the polymerization product of a macromer according to the invention with, if appropriate, at least one vinylic comonomer (a) and with at least one comonomer (b).

Examples of typical comonomers (b) are, for example, allyl(meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth)acrylate, methylenebis(meth)acrylamide, triallyl phthalate or diallyl phthalate.

The amount of comonomer (b) used is expressed in the weight content with respect to the total polymer and is in the range from 20 to 0.05%, in particular in the range from 10 to 0.1%, and preferably in the range from 2 to 0.1%.

4. "Material D"

Another advantageous embodiment of the present invention relates to the use of a siloxane-containing macromer which is formed from a poly(dialkylsiloxane) dialkoxyalkanol having the following structure:

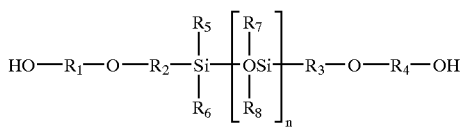

where n is an integer from about 5 to about 500, preferably about 20 to 200, more preferably about 20 to 100;

the radicals $R_1$, $R_2$, $R_3$, and $R_4$, independently of one another, are lower alkylene, preferably $C_1$–$C_6$ alkylene, more preferably $C_1$–$C_3$ alkylene, wherein in a preferred embodiment, the total number of carbon atoms in $R_1$ and $R_2$ or in $R_3$ and $R_4$ is greater than 4; and $R_5$, $R_6$, $R_7$, and $R_8$ are, independently of one another, are lower alkyl, preferably $C_1$–$C_6$ alkyl, more preferably $C_1$–$C_3$ alkyl.

The general structure of the Material D macromer follows:

ACRYLATE -LINK-ALK-O-ALK-PDAS-ALK-O-ALK-LRNK-ACRYLATE where the ACRYLATE is selected from acrylates and methacrylates; LINK is selected from urethanes and dirurethane linkages, ALK-O-ALK is as defined above ($R_1$—O—$R_2$ or $R_3$O—$R_4$), and PDAS is a poly(dialkylsiloxane).

For example, a Material D macromer may be prepared by reacting isophorone diisocyanate, 2-hydroxyethyl (meth)acrylate and a poly(dialkylsiloxane) dialkoxyalkanol in the presence of a catalyst.

A preferred Material D macromer may be prepared by reacting a slight excess of isocyanatoalkyl methacrylate, especially isocyanatoethyl methacrylate (IEM), with a poly(dialkylsiloxane) dialkoxyalkanol, preferably poly(dimethylsiloxane) dipropoxyethanol, in the presence of a catalyst, especially an organotin catalyst such as dibutyltin dilaurate (DBTL).

The primary resulting structure is as follows:

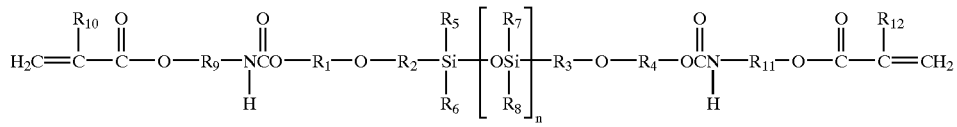

where $R_9$ and $R_{11}$ are alkylene; preferably $C_{1-6}$ alkylene, more preferably ethylene; $R_{10}$ and $R_{12}$ are methyl or hydrogen.

The "Material D" prepolymer mixture may be formed by mixing the aforementioned siloxane-containing macromer with one or more hydrophilic monomers and a thermoinitiator or a photoinitiator such as Darocur®1173. A solvent, such as hexanol, is preferably added to homogenize the mixture. Preferably, an appropriate amount of TRIS is added to lower the modulus of elasticity to a desired level. The ionoperm monomer or monomers may be selected from any of the aforementioned ionoperm or hydrophilic monomers. Preferably, the ionoperm monomer is selected from the group consisting of acrylates, methacrylates, acrylamides, methacrylamides and mixtures thereof. More preferably, the ionoperm monomers are selected from dimethylacrylamide (DMA) and methacrylic acid (MAA).

A preferred "Material D" prepolymer mixture, in weight percentages based on total mixture weight, includes about 35 to 60% Materal D macromer; about 6 to 25% TRIS; about 15 to 35% ionoperm monomer; about 0.1 to 1% photoinitiator; and about 10 to 20% solvent. A more preferred "Material D" prepolymer mixture, in weight percentages based on total mixture weight, includes the following: about 40 to 55% Materal D macromer; about 8 to 16% TRIS; about 20 to 30% dimethylacrylamide; about 0.2 to 2% methacrylic acid; about 0.1 to 1% photoinitiator; and about 10 to 20% solvent. A particularly preferred "Material D" prepolymer mixture, in weight percentages based on total mixture weight, includes the following: about 44 to 50% Materal D macromer; about 10 to 12% TRIS; about 22 to 26% dimethylacrylamide; about 0 to 1% methacrylic acid; about 0.2 to 0.6% photoinitiator; and about 10 to 20% solvent.

The prepolymer mixture may be formed into lenses and other ophthalmic devices by any of a number of techniques known in the art and disclosed herein. Preferably, the prepolymer mixture is conveyed into a concave half of a lens mold, the convex mold half is mated with the concave mold half, and an appropriate amount of radiation is applied to initiate polymerization. While ultraviolet (UV) radiation is preferred, a number of other energy sources known in the art and disclosed herein may also be used.

The Material D ophthalmic lens is preferably a polymerization product of the following macromeric and monomeric components, based on total weight of polymerizable material:

(a) about 45 to about 65 percent Material D macromer;

(b) about 5 to about 25 percent TRIS; and (c) about 20 to about 40 percent ionoperm monomer.

The Material D ophthalmic lens is more preferably a polymerization product of the following macromeric and monomeric components, based on total weight of polymerizable material:

(a) about 50 to about 60 percent Material D macromer;

(b) about 10 to about 20 percent TRIS; and (c) about 25 to about 35 percent ionoperm monomer.

In a preferred embodiment, the Material D ophthalmic lens is a polymerization product of the following macromeric and monomeric components, based on total weight of polymerizable material:

(a) about 50 to about 60 percent Material D macromer;

(b) about 10 to about 20 percent TRIS;

(c) about 25 to about 35 percent DMA; and (d) up to about 2 percent MAA.

In another preferred embodiment, about 0.2 to 1.0 weight percent MAA is used, together with the components (a), (b), and (c) in the above-cited amounts.

III. OPHTHALMICALLY COMPATIBLE SURFACES

The ophthalmic lenses of the present invention have a surface which is biocompatible with ocular tissue and ocular fluids during the desired extended period of contact. In one preferred embodiment, the ophthalmic lenses of the present invention include a core material, as defined above, surrounded, at least in part, by a surface which is more hydrophilic and lipophobic than the core material. A hydrophilic surface is desirable in order to enhance the compatibility of the lens with the ocular tissues and tear fluids. As surface hydrophilicity increases, undesirable attraction and adherence of lipids and proteinaceous matter typically decreases. There are factors other than surface hydrophilicity, such as immunological response which may contribute to deposit accumulation on the lens. Deposition of lipids and proteinaceous matter causes haze on the lens, thereby reducing visual clarity. Proteinaceous deposits may also cause other problems, such as irritation to the eye. After extended periods of continuous or intermittent wear, the lens must be removed from the eye for cleaning, i.e., deposit removal. Therefore, increased surface hydrophilicity, and concomittent reductions in deposits of biological matter, allows increased wear time.

"Surface treatment processes" as used herein, refers to processes to render a surface more ophthalmically compatible, in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified.

There are a variety of methods disclosed in the art for rendering a surface of a material hydrophilic. For example, the lens may be coated with a layer of a hydrophilic polymeric material. Alternatively, hydrophilic groups may be grafted onto the surface of the lens, thereby producing a monolayer of hydrophilic material. These coating or grafting processes may be effected by a number of processes, including without limitation thereto, exposing the lens to plasma gas or immersing the lens in a monomeric solution under appropriate conditions.

Another set of methods of altering the surface properties of a lens involves treatment prior to polymerization to form the lens. For example, the mold may be treated with a plasma (i.e., an ionized gas), a static electrical charge, irradiation, or other energy source, thereby causing the prepolymerzation mixture immediately adjacent the mold surface to differ in composition from the core of the prepolymerization mixture.

A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

In a preferred embodiment, the lens is plasma treated in the presence of a mixture of (a) a $C_{1-6}$ alkane and (b) a gas selected from the group consisting of nitrogen, argon, oxygen, and mixtures thereof. In a more preferred embodiment, the lens is plasma treated in the presence of a mixture of methane and air.

IV. UTILITY

A. Ophthalmic Lenses

The novel polymers or crosslinked polymers can be converted into ophthalmic moldings in a manner known in the art, in particular into contact lenses, for example by carrying out the photopolymerization or photocrosslinking of the novel polymers in a suitable contact lens mold. Examples of novel ophthalmic moldings, in addition to contact lenses, include without limitation thereto, contact lenses for vision correction, contact lenses for eye color modification, ophthalmic drug delivery devices, ophthalmic wound healing devices, and the like.

B. Contact Lenses

A specific embodiment of the invention is directed to contact lenses which comprise essentially a novel polymer or polymeric network. Such contact lenses have a range of unusual and extremely advantageous properties. Amongst these properties are, for example, their excellent compatibility with the human cornea (if necessary after suitable surface treatment (coating)) and with tear fluid, which is based on a balanced ratio between water content and water permeability, oxygen permeability and mechanical and adsorptive properties. This balance of desirable properties results in high comfort and the absence of irritation and allergenic effects. Owing to their favorable permeability properties with respect to various salts, nutrients, water and diverse other components of tear fluid and gases ($CO_2$ and $O_2$), the novel contact lenses have no effect, or virtually no effect, on the natural metabolic processes in the cornea. In contrast to many other siloxane-containing contact lenses, the present innovative extended-wear lenses have chemical and mechanical properties and ion permeability sufficient to avoid the undesired binding effect. Furthermore, the novel contact lenses have high dimensional stability and shelf life.

It must be emphasized that this balance of properties, especially the high ion permeability in combination with the high oxygen permeability, is key to producing a true extended-wear contact lens. The high oxygen permeability is required to prevent corneal swelling, thereby reducing the likelihood of ocular damage and wearer discomfort during periods of extended wear. The high ion permeability enables the lens to move on the eye such that corneal health is not substantially altered and wearer comfort is acceptable during a period of extended, continuous contact with ocular tissue and ocular fluids.

The preferred extended-wear contact lenses of the present invention are those which are comfortable over the period of extended wear. If the lens diameter is too small, the eyelids will not cover any portion of the lens when the eye is open. Thus, the eyelids will contact the edge of the lens each time the eyelid is closed. This repeated eyelid-lens interaction typically causes irritation, wearer discomfort, and lens dislodgement. Accordingly, the preferred contact lens diameters are those which are sufficiently large to minimize eyelid-lens interaction and the associated irritation. Preferably, the contact lens has a diameter of about 12 to about 16 millimeters, more preferably about 13 to 15 mm, and most preferably about 13.5 to 14.8 mm.

V. METHODS OF USE AS EXTENDED-WEAR LENSES

The above-described ophthalmic lenses have special utility as extended-wear contact lenses. Contact lenses having sufficient oxygen and water transmission rates from inner (base curve) to outer (front curve) surface may be continuously worn for long periods of time without substantial corneal swelling or wearer discomfort. The method of wear includes (a) applying the lens to the eye and (b) allowing the lens to remain in intimate contact with the eye and tear fluids for a period of at least 24 hours without substantial adverse impact on corneal health or wearer comfort.

A preferred method includes additional steps of (c) removing the lens from the ocular environment; (d) treating the lens (i.e., disinfecting or cleaning the lens); (e) re-applying the lens to the eye; and (f) allowing the lens to remain in intimate contact with the eye and tear fluids for a period of at least an additional 24 hours without substantial adverse impact on corneal health or wearer comfort.

In a preferred embodiment, the lens is worn for a continuous period of at least four (4) days without substantial corneal swelling or wearer discomfort. In another preferred embodiment, the lens is worn for a continuous period of at least seven (7) days without substantial corneal swelling or wearer discomfort. In another preferred embodiment, the lens is worn for a continuous period of at least 14 days without substantial corneal swelling or wearer discomfort. In yet another preferred embodiment, the lens is worn for a continuous period of at least 30 days without substantial corneal swelling or wearer discomfort

VI. METHODS OF MANUFACTURE

The ophthalmic lens may be manufactured, generally, by thoroughly mixing the oxyperm and ionoperm polymerizable materials applying an appropriate amount of the mixture to a lens mold cavity, and initiating polymerization. Photoinitiators, such as those commercially available photoinitiators disclosed above, may be added to the prepolymerization mixture to aid in initiating polymerization. Polymerization may be initiated by a number of well known techniques, which, depending on the polymerizable material, may include application of radiation such as microwave, thermal, e-beam and ultraviolet. A preferred method of initiating polymerization is by application of ultraviolet radiation.

It has been discovered that the ion and/or water permeability of some of the aforementioned core materials may be increased by initiating and completing polymerization in an atmosphere which is substantially free of oxygen. Suitable gases which are readily commercially available include, without limitation thereto, nitrogen and carbon dioxide. Thus, in a preferred embodiment, the oxyperm and ionoperm polymerizable materials are polymerized in an atmosphere having less than about 10000 ppm oxygen. More preferably, the atmosphere surrounding the polymerizable material contains less than about 1000 ppm oxygen. Even more preferably, the surrounding atmosphere contains less than about 100 ppm oxygen, while the most preferred oxygen content is less than about 20 ppm.

In the aforementioned embodiment, the prepolymer mixture must be degassed prior to polymerization. The degassing may be accomplished by a number of techniques known in the art. One technique for degassing the prepolymer mixture involves the use of a series of freezing and thawing steps which are repeated until the appropriate gas concentration level is achieved in the prepolymer mixture. This freeze/thaw method involves cooling the prepolymer mixture until the mixture solidifies, applying a vacuum to the solidified prepolymer mixture, discontinuing the vacuum, and thawing the prepolymer mixture until the mixture is again in liquid form. While this degassing technique is advantageous in a laboratory setting, other degassing techniques known in the art may be more advantageous for commercial lens manufacturing processes.

Alternatively, the atmosphere surrounding the lens mold may be include oxygen, under certain conditions. For example, if the lens mold halves seal adequately to one another and the lens mold material has a low rate of oxygen permeability (e.g., polypropylene), it is possible to polymerize a degassed prepolymer mixture in a mold surrounded by ambient air without reaching prepolymer oxygen concentrations sufficiently high to substantially reduce ion or water permeability of the final lens. Thus, in another preferred embodiment of double-sided molding, the lens is formed by the following steps: (1) the prepolymer mixture is degassed, (2) a lens mold half is filled with the prepolymer mixture, (3) the mold halves are sealed to one another, and (4) the polymerization is initiated to form the lens, where the lens mold halves are formed from a material having a low oxygen permeability and steps (2)–(4) may occur in the presence or absence of oxygen. In this embodiment, it is preferred that the lens molds are stored in an inert substantially oxygen-free atmosphere, e.g., nitrogen or carbon dioxide, prior to use.

An essential feature of the manufacturing methods of the present innovative lenses is that a balance of high oxygen permeability and high ion permeability is achieved. Manufacturing techniques and conditions which result in lowering either the oxygen permeability or the ion permeability below levels sufficient to maintain good corneal health and on-eye movement during periods of extended wear are unacceptable to produce the innovative extended-wear contact lenses of the present invention.

Preferably, the manufacturing method produces a contact lens having a Dk/t of at least 70 barrers/mm and a Ionoton Ion Permeability Coefficient of at least $0.2 \times 10^{-6}$ cm$^2$/sec. More preferably, the manufacturing method produces a contact lens having a Dk/t of at least 75 barrers/mm and a Ionoton Ion Permeability Coefficient of at least $0.3 \times 10^{-6}$ cm$^2$/sec. The manufacturing method preferably provides a contact lens having a Dk/t of at least 87 barrers/mm and a Ionoton Ion Permeability Coefficient of at least $0.4 \times 10^{-6}$ cm$^2$/sec.

The previous disclosure will enable one having ordinary skill in the art to practice the invention. In order to better enable the reader to understand specific embodiments and the advantages thereof, reference to the following examples is suggested. However, the following examples should not be read to limit the scope of the invention.

Examples A–D are arranged in accordance with the materials defined above. Thus, Examples A-1, A-2, etc. relate to Material "A" as defined above, Examples B-1, B-2, etc. relate to Material "B" as defined above, Examples C-1, C-2, etc. relate to Material "C" and Examples D-1, D-2, etc. relate to Material "D". Temperatures are stated in degrees Celsius unless otherwise specified.

Examples E, F and G are directed to demonstrating a correlation between on-eye movement and the Ionoton Ion Permeability Coefficient, the Ionoflux Ion Permeability Coefficient, and the Hydrodell Water Permeability Coefficient, respectively.

EXAMPLE A-1

A polysiloxane macromer is prepared by reacting, at room temperature (about 21 C.), one mole equivalent (about 100 grams) of poly(dimethylsiloxane) dialkanol (Shin Etsu Chemical Co., Tokyo, Japan) having hydroxyethyl propoxy end groups with 2 mole equivalents (about 21.2 grams) of isophorone diisocyanate (Aldrich Chemical Co., Milwaukee, Wis.) in the presence of about 0.2 grams dibutyltin dilaurate catalyst (Pfaltz & Bauer, Inc., Waterbury, Conn.). After about 48 hours reaction time, 2.02 mole equivalents (about 38.7 grams) of poly(ethylene glycol) ("PEG" about 610 g/mol Mn, Dow Chemical Corp., Midland, Mich.) and about 0.17 grams of dibutyltin dilaurate (about 0.43% by weight PEG) are added to 80 grams of the reaction product from the prior step. Sufficient chloroform (Aldrich Chemical Co.) is added to the mixture to make the mixture homogeneous. This mixture is stirred at room temperature for about 15 hours. Next, the mixture is stirred for about 8 hours at a temperature of about 44 to 48 C., with the temperature held substantially constant by a surrounding oil bath. The chloroform is then evaporated, in order to achieve a final concentration of about 50% by weight solids, by stirring the mixture at room temperature for about 8 hours. Then, about 2.14 mole equivalents (about 10.4 grams) of isocyanatoethyl methacrylate ("IEM" Monomer Polymer, Inc., Feasterville, Pa.) is added to the mixture. Finally, the mixture is covered with aluminum foil and stirred at room temperature for about 17 hours, yielding a polysiloxane-containing macromer having a number-average molecular weight (Mn) of about 4000 grams per mole.

The macromeric solution is then polymerized, in the presence of about 0.5 weight percent DAROCUR® 173 photoinitiator (Ciba-Geigy Corporation, Ardsley, N.Y.) to form contact lenses. Polypropylene contact lens molds are filled with the copolymer precursor solution. Ultraviolet light (about 300 to 400 nm) at about 3–6 mW/cm$^2$ is applied to the solution in the mold for about 3 hours at room temperature. The UV light, in conjunction with the photoinitiator, causes polymerization, thereby allowing the solution to form a contact lens having the shape of the mold. The lenses are extracted with isopropanol to remove the remaining chloroform solvent and any unreacted components. The product is a polysiloxane-containing polymeric contact lens.

Prior to taking oxygen permeability measurements, the lenses are hydrated by placing the lenses in isotonic buffered saline solution for at least eight hours. After hydration, if necessary because of handling, each lens is cleaned with MIRAFLOW® Daily Cleaner (CIBA Vision Corporation, Duluth, Ga.) to remove grease and lipids prior to testing. Excess MIRAFLOW® cleaner is removed by rinsing with saline or purified water.

Oxygen fluxes (J) are measured at 34 C. in a wet cell (i.e., gas streams are maintained at about 100% relative humidity) using a Dk1000 instrument. Oxygen transmissibility, $D_k/t$, is determined as outlined in the portions of the specification relating to oxygen permeability and transmissibility.

EXAMPLE A-2

A polysiloxane macromer is first prepared substantially in accordance with the procedure described in Example A-1.

A copolymer precursor solution is prepared by mixing about 180 grams polysiloxane-containing macromer, about 15 grams 3-methacryloxypropyltris (trimethylsiloxy) silane (Shin Etsu), about 4 grams 2-hydroxyethyl methacrylate ("HEMA"), about one gram ethylene glycol dimethacrylate ("EDGMA"), and about one gram DAROCUR® 1173 photoinitiator at room temperature for about 16 hours.

The copolymer precursor solution is then polymerized to form contact lenses. Polypropylene contact lens molds are filled with the copolymer precursor solution. Ultraviolet light (about 300 to 400 nm) at about 3–6 mW/cm$^2$ is applied to the solution in the mold for about 3 hours at room temperature. The LV light causes polymerization, thereby allowing the solution to form a contact lens having the shape of the mold. The lens are extracted with isopropanol to remove remaining chloroform solvent and any unreacted components. A preferred resulting polymer contains about 81.8 weight percent polysiloxane macromer, about 13.6% TRIS, about 3.6% 2-hydroxyethyl methacrylate, and about 0.9% EDGMA. [059–87]

The contact lens is degassed by placing the lens under suitable vacuum for a period sufficient to remove substantially all gas from the lens matrix. Fully hydrated degassed contact lenses having this composition have a Dk of about 87 barrers, a water content of about 19 weight percent, and a modulus of elasticity of about 2.5 MPa.

EXAMPLE A-3

A contact lens is prepared substantially in accordance with the procedure described in Example A-2, but having the final composition of about 19.5 weight percent polysiloxane macromer, about 47% TRIS, and about 33.5% N,N-dimethylacrylamide. Fully hydrated contact lenses having this composition have a Dk of about 49 barrers, a water content of about 30 weight percent, and a modulus of elasticity of about 2.4 MPa.

EXAMPLE A-4

A contact lens is prepared substantially in accordance with the procedure described in Example A-2, but having the final composition of about 30 weight percent polysiloxane macromer, about 50% TRIS and about 20% N,N-dimethylacrylamide. Fully hydrated contact lenses having this composition have a Dk of about 76 barrers, a water content of about 20 weight percent, and a modulus of elasticity of about 1.3 MPa.

EXAMPLE A-5

A contact lens is prepared substantially in accordance with the procedure described in Example A-2, but having the final composition of about 30 weight percent polysiloxane macromer, about 40% TRIS and about 30% N,N-dimethylacrylamide. Fully hydrated contact lenses having this composition have a Dk of about 55 barrers, a water content of about 30 weight percent, and a modulus of elasticity of about 3.5 MPa.

EXAMPLE A-6

A contact lens is prepared substantially in accordance with the procedure described in Example A-2, but having the final composition of about 30 weight percent polysiloxane macromer, about 60% TRIS and about 10% N,N-dimethylacrylamide. Fully hydrated contact lenses having this composition have a Dk of about 110 barrers, a water content of about 8.7 weight percent, and a modulus of elasticity of about 2.6 MPa.

EXAMPLE A-7

A contact lens is prepared substantially in accordance with the procedure described in Example A-2, but having the final composition of about 30 weight percent polysiloxane macromer and about 70% TRIS. Fully hydrated contact lenses having this composition have a Dk of about 128 barrers and a water content of about 4.9 weight percent.

EXAMPLE A-8

A contact lens is prepared substantially in accordance with the procedure described in Example A-2, but having the final composition of about 30 weight percent polysiloxane macromer, about 45% TRIS, 5% fluoroacrylate, and about 20% N,N-dimethylacrylamide. Fully hydrated contact lenses having this composition have a Dk of about 69 barrers, a water content of about 20 weight percent, and a modulus of elasticity of about 1.4 MPa.

EXAMPLE A-9

A contact lens is prepared substantially in accordance with the procedure described in Example A-2, but having the final composition of about 82 weight percent polysiloxane macromer, about 14.4% TRIS, and about 3.7% 2-hydroxyethyl methacrylate. Fully hydrated contact lenses having this composition have a Dk of about 96 barrers, a water content of about 19 weight percent, and a modulus of elasticity of about 1.8 MPa.

EXAMPLE A-10

A polysiloxane macromer is prepared substantially in accordance with the procedures described in Example A-1, but the polyethylene glycol has a molecular weight of about 660.

A contact lens is prepared substantially in accordance with the procedure described in Example 2, but having the final composition of about 81.9 weight percent polysiloxane macromer, about 13.6% TRIS, about 3.7% 2-hydroxyethyl methacrylate, and about 0.8% ethylene glycol dimethacrylate. Fully hydrated contact lenses having this composition have a Dk of about 81 barrers, a water content of about 20 weight percent, and a modulus of elasticity of about 1.4 MPa.

EXAMPLE A-11

A contact lens is prepared substantially in accordance with the procedure described in Example A-2, but having the final composition of about 82 weight percent polysiloxane macromer, about 8.6% TRIS, about 4.9% fluoroacrylate, about 3.5% 2-hydroxyethyl methacrylate, and about 1% EDGMA. Fully hydrated contact lenses having this composition have a Dk of about 77 barrers, a water content of about 22 weight percent, and a modulus of elasticity of about 1.3 MPa.

EXAMPLE A-12

A contact lens is prepared substantially in accordance with the procedure described in Example A-1, but the polysiloxane macromer used has hydroxy-sec-butyl end groups as opposed to hydroxyethylpropoxy end groups. The fully hydrated contact lens, after degassing, has a Dk of about 70 barrers, about a 22 weight percent water content, and a modulus of elasticity of about 2.4 MPa.

EXAMPLE B-1

Macromer Synthesis 51.5 g (50 mmol) of the perfluoropolyether Fomblin® ZDOL (from Ausimont S.p.A, Milan) having a mean molecular weight of 1030 g/mol and containing 1.96 meq/g of hydroxyl groups according to end-group titration is introduced into a three-neck flask together with 50 mg of dibutyltin dilaurate. The flask contents are evacuated to about 20 mbar with stirring and subsequently decompressed with argon. This operation is repeated twice. 22.2 g (0.1 mol) of freshly distilled isophorone diisocyanate kept under argon are subsequently added in a counterstream of argon. The temperature in the flask is kept below 30° C. by cooling with a waterbath. After stirring overnight at room temperature, the reaction is complete. Isocyanate titration gives an NCO content of 1.40 meq/g (theory: 1.35 meq/g).

202 g of the $\alpha,\omega$-hydroxypropyl-terminated polydimethylsiloxane KF-6001 from Shin-Etsu having a mean molecular weight of 2000 g/mol (1.00 meq/g of hydroxyl groups according to titration) are introduced into a flask. The flask contents are evacuated to approx. 0.1 mbar and decompressed with argon. This operation is repeated twice. The degassed siloxane is dissolved in 202 ml of freshly distilled toluene kept under argon, and 100 mg of dibutyltin dilaurate (DBTDL) are added. After complete homogenization of the solution, all the perfluoropolyether reacted with. isophorone diisocyanate (IPDI) is added under argon. After stirring overnight at room temperature, the reaction is complete. The solvent is stripped off under a high vacuum at room temperature. Microtitration shows 0.36 meq/g of hydroxyl groups (theory 0.37 meq/g). 13.78 g (88.9 mmol) of 2-isocyanatoethyl methacrylate (IEM) are added under argon to 247 g of the $\alpha,\sigma$-hydroxypropyl-terminated polysiloxane-perfluoropolyether-polysiloxane three-block copolymer (a three-block copolymer on stoichiometric average, but other block lengths are also present). The mixture is stirred at room temperature for three days. Microtitration then no longer shows any isocyanate groups (detection limit 0.01 meq/g). 0.34 meq/g of methacryl groups are found (theory 0.34 meq/g).

The macromer prepared in this way is completely colourless and clear. It can be stored in air at room temperature for several months in the absence of light without any change in molecular weight.

EXAMPLE B-2

Macromer Synthesis

The first step of the macromer synthesis described under Example B-1 is repeated. An isocyanate titration of the perfluoropolyether reacted with IPDI gives a content of 1.33 meq/g of NCO (theory 1.35 meq/g).

In a second step, 87.1 g of the $\alpha,\sigma$-hydroxypropyl-terminated polydimethylsiloxane TegomerH-Si2111 (Th. Goldschmidt AG, Essen) having a mean molecular weight of 890 g/mol (2.25 meq/g of hydroxyl groups according to titration) are dissolved in 87 ml of toluene. After the reaction has been carried out as indicated under B-1 and the solvent has been removed, a hydroxyl group content of 0.66 meq/g is determined by microtitration (theory 0.60 meq/g). The resultant intermediate is in turn reacted with a stoichiometric amount of isocyanatoethyl methacrylate. Microtitration then no longer shows any isocyanate groups (detection limit 0.01 meq/g). 0.56 meq/g of methacryl groups are found (theory 0.53 meq/g). The macromer prepared in this way is completely colourless and clear and has a long shelf life.

EXAMPLE B-3

Macromer Synthesis

The first step of the macromer synthesis described under Example B-1 is repeated, but using a different perfluoropolyether: Fomblin® ZDOLTX (from Ausimont S.p.A., Milan). This material is terminated by O—$CF_2$—$CH_2$—($OCH_2CH_2$)$_n$—OH (where n=0, 1 or 2). The material used has a mean molecular weight of 1146 g/mol, and contains 1.72 meq/g of hydroxyl groups according to end-group analysis. An isocyanate titration of the perfluoropolyether reacted with IPDI shows a content of 1.23 meq/g of NCO (theory 1.25 meq/g).

In the second step, a stoichiometric amount of Tegomer Hi-Si211 and toluene are again added. After the reaction has been carried out as indicated under Example B-1 and the solvent has been removed, a hydroxyl group content of 0.63 meq/g is determined by microtitration (theory 0.58 meq/g). The resultant intermediate is in turn reacted with a stoichiometric amount of isocyanatoethyl methacrylate. Microtitration then no longer shows any isocyanate groups (detection limit 0.01 meq/g). 0.55 meq/g of methacryl groups are found (theory 0.51 meq/g). The macromer prepared in this way is completely colourless and clear and has a long shelf life.

EXAMPLE B-4

Macromer Synthesis

The first step of the macromer synthesis described under Example B-1 is repeated, but 5.0 g of Fomblin/ZDOL and 2.18 g of IPDI are employed. When the reaction is complete, microtitration shows an isocyanate group content of 1.31 meq/g of hydroxyl groups (theory 1.36 meq/g).

The second step of the synthesis described under Example B-1 is likewise carried out analogously, the stoichiometric ratio between isocyanate-terminated perfluoropolyether and hydroxypropyl-terminated polysiloxane being 2:3. After the reaction has been completed and the solvent has been removed, microtitration shows a content of 0.2 meq/g of hydroxyl groups (theory 0.1 8 meq/g).

The third step of the synthesis described under Example B-1 is likewise carried out analogously, IEM being employed in a precisely stoichiometric ratio. After the reaction, free isocyanate groups can no longer be detected (detection limit 0.01 meq/g). 0.19 meq/g of methacryl groups are found (theory 0.19 meq/g).

EXAMPLE B-5

Production of Contact Lenses 13.0 g of macromer from Example B-1 are dissolved in 5.6 g of ethanol (Fluka, puriss. p.a.) (70% by weight solution). After complete homogenization of the solution, 5.2 g of 3-tris(trimethylsiloxy)silylpropyl methacrylate (TRIS from Shin-Etsu, product No. KF-2801), 7.8 g of freshly distilled dimethylacrylamide (DMA) and 160 mg of photoinitiator Darocur® 1173 (Ciba) are added. This solution is filtered through a Teflon membrane having a pore width of 0.45 mm under an argon pressure of from 1 to 2 atm. The filtered solution is frozen in a flask in liquid nitrogen, the flask is evacuated under a high vacuum, and the solution is returned to room temperature with the flask sealed. This degassing operation is repeated twice. The flask containing the macromer/comonomer solution is then transferred into a glove box with an inert-gas atmosphere, where the solution is pipetted into dust-free contact-lens moulds made from polypropylene. The moulds are closed, and the polymerization reaction is effected by UV irradiation (15 mW/cm2, 5 min.), with simultaneous crosslinking. The moulds are then opened and placed in ethanol, causing the resultant lenses to swell out of the moulds. The lenses are extracted for 24 hours with constantly replenished distilled dichloromethane and subsequently dried in a high vacuum. The dried lenses are equilibrated in phosphate-buffered physiological saline solution in autoclave-resistant vials and then autoclaved at 120° C. for 30 minutes. All physical data measurements are carried out on autoclaved lenses.

The lenses produced in this way are characterized by the following values: oxygen permeability (Dk) 77 barrer (determined by the "wet" method described below), water content of the equilibrated lenses 32 percent by weight, elongation at break at 35° C. 360%, modulus of elasticity 30° C. 0.5MPa (measured using a Minimat from Polymer Laboratories, UK).

"Wet" measurement of the oxygen permeability

The oxygen permeability of a material is determined by the coulometric method. To this end, pre-autoclaved lenses are clamped in a holder and then covered on the upper side with a 2cm layer of water. A gas mixture comprising 21% of oxygen and 79% of nitrogen is passed continuously through the water layer with swirling. The oxygen which diffuses through the lens is measured using a coulometric detector. The reference values are those measured on commercially available contact lenses using this method. Cibasoft/(CIBA-Vision, HEMA lens) gives a measurement of approx. 7–10 barrer, and Excelens/(CIBA-Vision, PVA lens) gives a measurement of approx. 22 barrer.

Unfortunately, the oxygen permeability of, for example, contact lenses is frequently given to in the literature as a straight Dk value without further definition and frequently without giving any reference material. These are usually values determined on dry material (dry measurement). A comparative measurement of the oxygen permeability of polymer B-5 shows the differences:

a) "wet" measurement: 77 barrer b) dry measurement: 158 barrer

EXAMPLE B-6

The process described under Example B-5 for the production of contact lenses is repeated, but the mixture of comonomers has the following composition (in per cent by weight):

55% of macromer from Example B-1

22% of TRIS 22.5% of DMA 0.5% of Blemer® QA

EXAMPLE B-7

The process described under Example B-5 for the production of contact lenses is repeated, but the mixture of comonomers has the following composition (in percent by weight):

55% of macromer from Example B-1

22% of TRIS

23% of DMA

EXAMPLE B-8

Analogously to EXAMPLE B-5 (in weight percent):

40% of macromer from Example B-1

30% of TRIS

30% of DMA

EXAMPLE B-9

The process described under B-5 for the production of contact lenses is repeated, but a 70% by weight solution of the macromer in toluene is used instead of the 75% by weight solution in ethanol described above. The mixture of comonomers has the following composition (in per cent by weight):

55% of macromer from Example B-1

22% of TRIS

23% of DMA

EXAMPLE B-10

The process described under B-5 for the production of contact lenses is repeated, but a 70% by weight solution of the macromer in octamethylcyclotetrasiloxane is used instead of the 75% by weight solution in ethanol described above. The mixture of comonomers has the following composition (in per cent by weight):

55% of macromer from Example B-1

22% of TRIS

23% of DMA

Physical measurement data for the contact-lens materials from Examples B-5 to B-10 ($O_2$Dk value, wet method) are presented in TABLE B-I:

TABLE B-I

| Example | Water Content [%] | Dk [barrer] | Modulus of Elasticity [MPa] | Elongation at Break [%] |
|---|---|---|---|---|
| B-5 | 32 | 77 | 0.5 | 360 |
| B-6 | 23.8 | 110 | 1.1 | 160 |
| B-7 | 19.5 | 110 | 0.6 | 130 |
| B-8 | 30.9 | 81 | 0.3 | 300 |
| B-9 | 30 | | | |
| B-10 | 25 | | | |

EXAMPLE B-11

About 10.0 grams of macromer from Example B-1 are dissolved in 3.3 grams of ethanol (Fluka, puriss. p.a.). After complete homogenization of the solution, about 4.0 grams of 3-tris(trimethylsiloxy)silylpropyl methacrylate (TRIS from Shin-Etsu, product no. KF-2801), about 5.9 g. freshly distilled dimethylacrylamide (DMA), about 0.1 g. Blemer® QA (a methacrylate having quaternary ammonium substituents, Linz Chemie) and about 100 mg of photoinitiator Darocur® 1173(Ciba) are added. The solution is filtered through a TEFLON membrane having a pore width of 0.45 mm under an argon pressure of from about 1 to 2 atm.

The filtered solution is frozen in a flask in liquid nitrogen, the flask is evacuated under a high vacuum, and the solution is returned to room temperature with the flask sealed. This degassing operation is repeated twice. The flask containing the macromer/comonomer solution is then transferred into a glove box with an inert gas atmosphere, where the solution is pipetted into dust-free, polypropylene contact lens molds. The molds are closed, and the polymerization reaction is effected by UV irradiation, with simultaneous crosslinking. The molds are then opened and placed in isopropyl alcohol, causing the resultant lenses to swell out of the molds. The lenses are extracted for about 24 hours with nearly continuous replenishing of isopropyl alcohol. Subsequently, the lenses are dried under high vacuum.

The dried contact lenses are equilibrated in autoclave-resistant vials in phosphate-buffered physiological saline solution, and then autoclaved for 30 minutes at about 120° C. Physical measurement data for the autoclaved lens is presented below:

| | |
|---|---|
| Dk [barrer]: | 93 |
| water content [%]: | 20.3% |
| modulus of elasticity [Mpa]: | 0.96 |

EXAMPLE B-12

Lenses are prepared in accordance with the procedures described in Example B-11, but are subsequent surface treated as follows. The dried lenses are transferred into a plasma coating apparatus wherein they are surface treated in a methane/"air" mixture ("air" as used here, denotes 79% nitrogen and 21% oxygen) for a period of about 5 minutes. The apparatus and plasma treatment process have been disclosed by H. Yasuda in "Plasma Polymerization"Academic Press, Orlando, Fla. (1985), pages 319 forward.

The plasma-treated contact lenses are equilibrated in autoclave-resistant vials in phosphate-buffered physiological saline solution, and then autoclaved for 30 minutes at about 120° C. Physical measurement data for the plasma-coated autoclaved lens is presented below:

| | |
|---|---|
| Dk [barrer]: | 88 |
| water content [%]: | 21.8% |
| modulus of elasticity [Mpa]: | 1.03 |

EXAMPLE B-13

Lenses are prepared in accordance with the procedures described in Example B-5, but the mixture comonomers has the following composition, in weight percentages:

| | |
|---|---|
| Macromer of Example B-1: | 60% |
| TRIS: | 25% |
| DMA: | 15% |

EXAMPLE B-14

Lenses are prepared in accordance with the procedures described in Example B-6, with the same comonomer composition, but the comonomers are dispensed into dust-free contact lens molds in ambient air atmosphere.

EXAMPLE C-1

Reaction of α,ω-bis-aminopropyl-dimethylpolysiloxane with D(+)gluconic acid d-lactone:

Before the reaction, the amino-functionalized polydimethylsiloxane employed for the synthesis (X-22-161-C, Shin Etsu, JP) was finely dispersed in acetonitrile, extracted and then subjected to molecular distillation.

The following reactions take place with exclusion of $H_2O$. 200 g of purified amino-functionalized polydimethylsiloxane (0.375 meq of $NH_2$/g; Mn(VPO) 3400–3900(VPO, Vapour Pressure Osmometry)), dissolved in 200 ml of absolute THF, are slowly added dropwise to a suspension of 13.35 g (75 mmol) of D(+)gluconic acid d-lactone in 50 ml of absolute THF and the mixture is stirred at 40° C. for about 24 hours until the lactone has reacted completely. (Monitoring of the reaction by thin layer chromatography (TLC): silica gel; i-propanol/H2O/ethyl acetate 6:3:1; staining with Ce(IV) sulfate/phosphoromolybdic acid solution (CPS reagent)). After the reaction, the reaction solution is concentrated to dryness and the residue is dried under 3 Pa (0.03 mbar) for 48 hours. 213.3 g of α,ω-bis(3-gluconamidopropyl)-poly-dimethylsiloxane are obtained. Titration of the amino groups with perchloric acid shows a conversion of the amino groups of more than 99.8%.

Reaction of α,ω-bis-3 gluconamidopropyl-dimethylpolysiloxane with IEM The product obtained above (213.3 g) is dissolved in 800 ml of absolute THF and the solution is heated to 40° C. with the addition of catalytic amounts of dibutyltin dilaurate (DBTDL). 14 g (90 mmol) of IEM in 20 ml of absolute THF are added dropwise to this solution over a period of about 4 hours. This corresponds to a concentration of 1.2 equivalents of IEM per gluconamide unit. The reaction is carried out in the course of 48 hours (monitoring of the reaction by IR spectroscopy detection of the NCO ties). The reaction solution is concentrated and the product is dried in a brown glass flask under 3 Pa (0.03 mbar) for 24 hours, while cooling with ice. 227.2 g of a colourless rubber-elastic product of high optical transparency remain.

EXAMPLE C-2 to C-7

Further amino propyl-dimethylpolysiloxanes (PDMS) are reacted with a different amount of gluconolactone and concentrations of IEM analogously to Example C-1. The examples are summarized in Table C-I.

TABLE C-I

| | Poly(dimethyl siloxane) [PDMS] | | | | Amount of batch | | |
|---|---|---|---|---|---|---|---|
| Example | Name | Type | Mn | $NH_2$* | PDMS g(mmol of $NH_2$) | Glu g (mmnol) | IEM g (mmol) |
| C-1 | X-22-161-C | term. | 3400 | 2 | 200 (75) | 13.4 (75) | 14.0 (90.0) |
| C-2 | X-22-161-C | term. | 3400 | 2 | 200 (74) | 13.4 (75) | 25.7 (165.0) |
| C-3 | X-22-161-C | term. | 3400 | 2 | 200 (75) | 13.4 (75) | 29.2 (187.5) |
| C-4 | PS 813 | pen. | 1200 | 1 | | | |
| C-5 | GP 4 | pen. | 3150 | 2.6 | | | |
| C-6 | GP 6 | pen. | 5960 | 3 | | | |
| C-7 | KF 8003 | pen. | 9700 | 4.7 | 200 (98) | 17.5 (98) | 18.2 (117.4) |

Legend:
X-22-161-C and KF 8003 are products from Shin Etsu (Japan), PS813 is a product from Petrarch-H ls, GP4 and GP6 are products from Genesee.
*Amino groups per macromer chain
Glu: D(+) gluconic acid d-lactone
term: terminal
pen: pendent

EXAMPLE C-8

The reaction is carried out in accordance with Example C-1, but instead of D(+)gluconic acid d-lactone, 75 mmol of lactobionic acid 1,5-lactone, suspended in 50 ml of absolute THF, are added dropwise to a solution of amino-functionalized polydimethylsiloxane (X-22-161 -C) in 180 ml of absolute THF and 20 ml of DMSO (pure, 99%). Titration of the amino groups with perchloric acid indicates a reaction conversion of 99% (<0.01 meq of NH2/g). Here also, a colourless optically clear macromer is obtained.

EXAMPLE C-9 and C-10

The reactions are carried out analogously to Example C-1. However, the catalyst necessary for addition of the isocyanate onto the hydroxyl groups is varied. Instead of DBTDL, catalytic amounts of 1,4-diazabicyclo[2.2.2]octane (DABCO) or 4-dimethylamino-pyridine (DMAP) are added and the reaction is continued as described under Example C-1. In both cases, an optically clear, colourless rubber-elastic macromer results in a manner corresponding to Example C-1.

EXAMPLE C-11

The reaction is carried out analogously to Example C-1. In a manner corresponding to Example C-8, 0.1 mol of lactobionic acid 1,5-lactone is suspended in 50 ml of absolute THF and the suspension is added dropwise to a solution of amino-functionalized polydimethylsiloxane (KF-8003) in 180 ml of absolute THF and 20 ml of DMSO (pure, 99%). The reaction time is increased to about 48 hours. A residual content of 0.07 meq of $NH_2$/g can be detected, and is reacted completely by addition of the corresponding molar amount of D(+)gluconic acid d-lactone to the reaction solution. The colourless highly transparent product has a residual content of amino groups of <0.01 meq/g.

EXAMPLE C-12

52.09 g (9.78 mmol) of purified amino-functionalized polydimethylsiloxane (X-22-161-C, Shin Etsu JP), dissolved in 110 ml of absolute THF, are initially introduced into the reaction vessel under an inert gas atmosphere, and 1.14 g (6.52 mmol) of D-glucaro-1,4:6,3-dilactone, dissolved in 20 ml of absolute THF, are added. The reaction solution is stirred at room temperature for 15 hours and then worked up in a manner corresponding to Example C- 1. The amine content is 0.134 meq/g. The terminal amino groups of the resulting penta-block macromer are reacted with gluconolactone in the following reaction step. 41.84 g (5.146 meq of NH2) of the above macromer and 0.917 g (5.15 mmol) of D(+)gluconic acid d-lactone are suspended in 300 ml of absolute THF and the suspension is stirred under nitrogen at 40° C. for 18 hours. The filtered solution is then concentrated and the residue is dried under 3 Pa (0.03 mbar) for 48 hours. A highly viscous optically clear substance having a residual content of amino groups of 0.013 meq/g results.

EXAMPLE C-13

Preparation of an amino- and perfluoroalkyl-functionalized polydimethylsiloxane:

3.0 ml of absolute toluene are added to 15 g of poly (dimethylsiloxane-co-methylhydrosiloxane) [Bayer Silopren U-230; 10,000 g/mol; 2.3 mmol of Si-H/g], and 1.72 g (9.2 mmol) of allylphthalimide [CAS Reg. No. 5428-09-1] are then added. The mixture is frozen several times and the flask evacuated and then brought to room temperature again. The flask is then let down with argon. 0.7 ml of a 0.005 molar solution of Lamnoreaux catalyst (prepared in accordance with U.S. Pat. No. 3,220,972, General Electric) in absolute toluene (100 ppm of Pt/mol of Si-H) is added and the mixture is heated to 80° C. After a reaction time of half an hour, a colourless, clear to slightly cloudy solution, the 1H—NMR spectrum of which no longer shows resonances of allylic hydrogen atoms, is obtained.

Thereafter, 6.2 g (15.3 mmol) of degassed allyl 1H,1H, 2H,2H-perfluorooctyl ether are slowly added and the mixture is stirred at 80° C. for 2 hours. A 1H—NMR spectrum now shows a severely weakened resonance of the Si-H function at 4.6 ppm and an intense resonance at 0.5 ppm, which originates from Si—CH$_2$ hydrogen atoms.

3.0 ml of 1-hexene are then added in order to react the remaining excess of Si—H groups, which could otherwise cause crosslinking of the polymer when air later has access. The mixture is further stirred at 80° C. for another half an hour. The reaction mixture is then left to stand overnight. The product is purified over a silica gel column with hexane/ethyl acetate (3:2), the solvent is stripped off and the macromer is dried under a high vacuum. A colourless, clear, viscous product is obtained. The macromer purified in this way is taken up in 20 ml of hexane, 20 ml of methylamine [33% in ethanol] are added and the mixture is heated to 40° C. After 10–15 minutes, a white voluminous precipitate separates out. After 30 minutes, the suspension is cooled and filtered and the precipitate is washed with a little hexane. The filtrate is evaporated and the residue is then dried under a high vacuum. Thereafter, the content of amino groups is determined by titrimetry (perchloric acid).

The resulting macromer is clear and viscous. The amino group content is 78.6% of theory. The total yield of macromer after the chromatographic purification is 75%.

Preparation of a gluconamide:

17.3 g (corresponding to an amine content of 5.4 meq) of this aminoalkyl-substituted product are dissolved in 20 ml of dried THF. The solution is repeatedly frozen, degassed and let down with argon. All the following operations are carried out in an argon atmosphere. 712 mg of D(+)-gluconic acid d-lactone (4 mmol) are then added. Because of the low solubility of the lactone, a suspension is initially obtained. After stirring overnight at 50° C., the solution is clear and the lactone has been used completely. The stoichiometric remaining amount of D(+)-gluconic acid d-lactone (260 mg, 1.46 mmol) is then added and the mixture is stirred again at 50° C. overnight. A trace of unreacted lactone is observed.

Completion of the reaction is monitored by means of thin layer chromatography on silica gel plates with the mobile phase 1-propanol/ethyl acetate/water (6:1:3). The silica gel plates are developed by means of Ce(IV) sulfate/phosphoromolybdic acid solution. Subsequent titration on amino groups yields a residual amino content of <0.1%. After filtration and removal of the solvent by distillation, a highly viscous clear macromer with 0.295 mequivalent of gluconamide per gram of macromer is obtained.

EXAMPLE C-14

Before the polymerization, the acrylates employed, isobutyl acrylate (IBA), N,N-dimethylacrylamide (DMA) and 3-methacryloyloxypropyl-tris(trimethylsilyloxy)silane (TRIS) are each freed from inhibitors by distillation. 0.32 g (2.76 mmol) of IBA, 0.80 g (8.1 mmol) of DMA and 1.44 g (3.4 mmol) of TRIS are weighed into a 50 ml round-bottomed flask and the flask is flushed with N2 for half an hour, while cooling with ice 1.44 g of macromer from Example C-1 are transferred to a round-bottomed flask with a nitrogen attachment, degassed under 3 Pa (0.03 mbar) for 24 hours and then dissolved in 2.7 g of ethanol which has been flushed with N2 for half an hour beforehand. The subsequent preparation of samples and the polymerization are carried out inside a glove box with exclusion of oxygen. The above monomer mixture and the macromer solution from Example C-1 are mixed, with the addition of 0.012 g (0.21 mmol) of Darocur® 1173 and the mixture is subjected to microfiltration (0.45 mm filter). 180 μl of this mixture are introduced into a polypropylene mould, which is then closed with an appropriate lid of polypropylene. The mixture is then irradiated with a UV-A mercury high pressure lamp in a nitrogen atmosphere in a UV oven equipped for this for 5 minutes. The lamps (5 each of the brand TLK40W/10R, Philips) are above and below the holder inserted. The irradiation intensity is 14.5 mW/cm2.

The polypropylene mould is opened and the finished discs or lenses are removed by soaking by means of a solvent mixture of methylene chloride and ethanol (2:3). The lenses and discs are extracted in ethanol at room temperature in special polypropylene cages for 48 hours and then dried at 40° C. under 10 Pa (0.1 mbar) for 24 hours (autoclaving at 120° C., 30 minutes). The discs show an E modulus of 1.1 MPa, a permeability to oxygen of 183 barrier and a hardness (Shore A) of 53.

EXAMPLE C-15 to C-19

Further polymers are prepared in a manner corresponding to Example C-14 (composition in percentages by weight). Table C-II shows examples C-15 to C-19 and the properties of the resulting materials measured on discs.

TABLE C-II

| Example | Water Content [%] | Macromer from Example | Macromer weight percent | DMA weight percent | DMEA weight percent | TRIS weight percent | E modulus [Mpa] | Dk [barrer] |
|---------|---|---|---|---|---|---|---|---|
| C-15 | not measured | C-3 | 32.8 | — | 30 | 37.2 | — | — |
| C-16 | 19.9 | C-3 | 32.9 | 34.3 | — | 32.7 | 0.7 | 84 |
| C-17 | 25.1 | C-3 | 39.3 | 34.3 | — | 36.4 | 0.9 | 72 |
| C-18 | 17.5 | C-3 | 35.7 | 34.3 | — | 30.0 | 0.7 | 100 |
| C-19 | 23.4 | C-3 | 33.3 | 33.3 | — | 33.4 | 0.7 | 96 |

Legend:
DMA: N,N-Dimethylacrylamide
TRIS: 3-Methacryloyloxypropyl-tris(trimethylsilyloxy)silane
DMEA: 2-Dimethylaminoethyl acrylate

EXAMPLE C-20

Uncoated Contact Lens

A contact lens is prepared in a manner corresponding to Example C-14, using the Example C-3 macromer, with the following composition in percentages by weight:

| | |
|---|---|
| Macromer: | 33.3 |
| DMA: | 33.3 |
| TRIS: | 33.4 |

The lens has a Dk of about 94 and a water content of about 20.0 weight percent. The results are presented in TABLE C-III for comparision with coated lens properties.

EXAMPLE C-21

Plasma-treated Contact Lens

Dried lenses prepared in accordance with the procedures described in Example C-20 are transferred into a plasma coating apparatus where the lenses are surface treated in a methane/"air" mixture ("air" as used here, denotes 79% nitrogen and 21% oxygen). The apparatus and plasma treatment process have been disclosed by H. Yasuda in "Plasma Polymerization" Academic Press, Orlando, Fla. (1985), pages 319 forward.

The dried plasma-treated contact lenses are equilibrated in autoclave-resistant vials in phosphate-buffered physiological saline solution, and then autoclaved for 30 minutes at about 120° C. The plasma-treated autoclaved lens has a Dk [barrer] of 90 and a water content of 21.5%. The results are presented in TABLE C-III for comparision with coated lens properties.

TABLE C-III

| Example | Surface type | Dk [barrer] | Water content [%] |
| --- | --- | --- | --- |
| C-20 | untreated | 94 | 20.0 |
| C-21 | plasma-treated | 90 | 21.5 |

EXAMPLE C-22

The synthesis of this polymer corresponds to Example C-14 with the following comonomer composition: Example C-3 macromer/TRIS/DMA: 32.8%/32.6%/34.2% (in percentages by weight) and an addition of 0.4% by weight of trimethylammonium-2-hydroxypropyl methacrylate hydrochloride (Blemer® QA, Nippon Oil Corp.). The polymer has a modulus of 0.9 MPa and a permeability to oxygen of '2 barrier. The water content is 25.1% (after 30 minutes' autoclaving at 120° C.). For comparison, Example C-16 has a water content of 20% with a very similar comonomer composition (no addition of Blemer® QA).

EXAMPLE C-23

The polymer is prepared analogously to Example C-14, but the polymerization is carried out in bulk, which means without addition of ethanol. The composition of the comonomers and the material properties of the polymer synthesized, measured on discs is given below.

| | |
| --- | --- |
| Example C-7 macromer: | 41% |
| IBA: | 23% |
| 1-vinyl-2-pyrrolidone (NVP): | 24% |
| acrylonitrile (AN): | 12% |
| Hardness (shore A): | 68 |

EXAMPLE C-24

The polymerization is carried out in accordance with Example C-14 but with the following changed comonomer composition:

macromer of Example C-7/IBA/TRIS 20%/19%/60% and 1% (in percentages by weight) of bis(3-methacryloyloxypropyl)tetra methyldisiloxane.

An optically clear polymer with an E modulus of 0.4 MPa, a permeability to oxygen of 241 barrier and a hardness (Shore A) of 42 is obtained.

EXAMPLES C-25 through C-27

Contact lenses are prepared in accordance with the procedure described in Example C-1 4. The compositions in weight percentages are as follows:

| Example | Macromer | Macromer weight percent | IBA weight percent | DMA weight percent | TRIS weight percent | HFBA weight percent |
| --- | --- | --- | --- | --- | --- | --- |
| C-25 | C-3 | 36.0 | 8.0 | 20.0 | 36.0 | — |
| C-26 | C-2 | 35.0 | 5.0 | 20.0 | 35.0 | 5.0 |
| C-27 | C-3 | 32.8 | — | 30.0 | 37.2 | — | where
 IBA is isobutylacrylate,
 DMA is N,N-Dimethylacrylamide
 TRIS is 3-methycryloyloxypropyl-tris(trimethylsiloxy) silane
 HFBA is acrylsäure-2,2–3,4,4,4-hexafluorbutylester

EXAMPLE C-28

The polymerization is carried out in accordance with Example C-14 but with the following changed comonomer composition: macromer of Example C-1/DMA/TRIS 33.3%/33.3%/33.3%. An optically clear polymer is obtained.

EXAMPLE D-1

Macromer Synthesis

In a dry box under nitrogen atmosphere, about 200 grams of dry PDMS dipropoxyethanol (Shin-Etsu) is added to a container. Isocyanatoethyl methacrylate (IEM) in an amount equal to about 2 moles per mole PDMS dialkanol is added to the container. About 0.1 weight percent dibutyltin dilaurate (DBTL) catalyst, based on PDMS dialkanol weight, is added to the container along with a stir bar. The container is immersed in an oil bath atop a stir plate, and secured in place with a clamp. A stream of UPC air at about 2 psig is passed over the mixture. The mixture is agitated at room temperature (about 22° C.) for about 24 hours. An iterative procedure follows in which the mixture is analyzed for isocyanate content and IEM is added if the PDMS dialkoxyalkanol has not been completely reacted. The mixture is stirred about 24 hours more. The macromer produced is a siloxane-containing macromer.

EXAMPLE D-2

Lens Fabrication

A prepolymerization mixture is prepared by mixing about 56 grams of the macromer from Example D-1, about 14 grams of TRIS about 29 grams N,N-dimethylacrylamide (DMA), about 1 gram methacrylic acid, about 0.5 grams Darocur® 1173 photoinitiator, and about 20 grams hexanol. The mixture is agitated for about 20 minutes at room temperature.

Next, the mixture is degassed via a series of freezing and thawing steps. The container is placed in a liquid nitrogen bath until the mixture solidifies. A vacuum is applied to the container at a pressure of about 200 millitorr or less for about 5 minutes. Then, the container is placed in a bath of room temperature water until the mixture is liquid again. This process is performed a total of three times.

The mixture is then polymerized to form contact lenses. The prepolymerization mixture is poured into polypropylene contact lens molds in a nitrogen atmosphere. The polymerization is effected by applying UV radiation (abotu 4–6 mW/cm$^2$) for a period of about 15 minutes.

The resulting fully hydrated contact lens has a water content of about 23%. The lens has a Dk of about 115 barrers and a modulus of elasticity of about 2 MPa.

EXAMPLE D-3

Lens Fabrication

A contact lens is prepared in accordance with the procedure described in Example D-2, with the difference being that the composition is about 50% macromer of Example D-1, about 20% TRIS and about 30% DMA.

The resulting fully hydrated contact lens has a water content of about 20%. The lens has a Dk of about 118 barrers and a modulus of elasticity of about 1.8 Mpa.

EXAMPLE E-1

Material A

A contact lens is prepared substantially in accordance with the procedure described in Example A-2. Prior to polymerization, the prepolymerization mixture is degassed by cooling the prepolymer mixture with liquid nitrogen until the mixture solidifies and is near liquid nitrogen temperature, then applying a vacuum (about 0.1 mm Hg) to the solidified prepolymer mixture, discontinuing the vacuum, and thawing the prepolymer mixture until the mixture is again in liquid form. This degassing procedure is performed a total of three times on the prepolymerization mixture.

The prepolymer mixture is cured in a nitrogen atmosphere to form the contact lens. The cured lens has an equilibrium water content of about 19%. Subsequent to curing, the lens is plasma treated for about 10 minutes in an atmosphere of methane and air at a 2:1 $CH_4$:air volume:volume ratio. The working pressure of the gas is about 50 millitorr. The plasma treatment is accomplished in a Plasma Polymerization Apparatus LCVD-20-400A (Plasmacarb, Bedford, Mass.).

The Ionoton Ion Permeability Coefficient of the lens is $0.81\times10^{-3}$ cm$^2$/sec. Clinical examination shows that the lens moves on the human eye. See Table E for a summary of the results.

EXAMPLE E-2

Material B

A contact lens is prepared substantially in accordance with the procedure described in Example B-10. Prior to polymerization, nitrogen gas is bubbled through the prepolymer mixture in order to remove oxygen from the prepolymer mixture.

The prepolymer mixture is cured in a nitrogen atmosphere to form the contact lens. The cured lens has an equilibrium water content of about 26 weight percent. No coating is applied to the surface.

The Ionoton Ion Permeability Coefficient of the lens is $-0.063\times10^{-3}$ cm$^2$/sec. Clinical examination shows that the lens does not move on the human eye. See Table E for a summary of the results.

EXAMPLE E-3

Material B

A contact lens is prepared substantially in accordance with the procedure described in Example B-12. Prior to polymerization, the prepolymerization mixture is degassed by the repeated freeze/thaw procedure of Example E-1.

The prepolymer mixture is cured in a nitrogen atmosphere to form the contact lens. The cured lens has an equilibrium water content of about 30 weight percent. Subsequent to curing, the lens is plasma treated for about 3 minutes in an atmosphere of methane and air at a 2:1 $CH_4$:air volume ratio.

The Ionoton Ion Permeability Coefficient of the lens is $0.50\times10^{-3}$ cm$^2$/sec. Clinical examination shows that the lens moves on the human eye. See Table E for a summary of the results.

EXAMPLE E-4

Material B

A contact lens is prepared substantially in accordance with the procedure described in Example B-12. Prior to polymerization, the prepolymerization mixture is degassed by the repeated freeze/thaw procedure of Example E-1.

The prepolymer mixture is cured in a nitrogen atmosphere to form the contact lens. The cured lens has an equilibrium water content of about 30 weight percent. Subsequent to curing, the lens is plasma treated for about 5 minutes in an atmosphere of methane and air at a 2:1 $CH_4$:air volume ratio.

The Ionoton Ion Permeability Coefficient of the lens is $0.47\times10^{-3}$ cm$^2$/sec. Clinical examination shows that the lens moves on the human eye. See Table E for a summary of the results.

EXAMPLE E-5

Material B

A contact lens is prepared substantially in accordance with the procedure described in Example B-12. Prior to polymerization, the prepolymerization mixture is degassed by the repeated freeze/thaw procedure of Example E-1.

The prepolymer mixture is cured in a nitrogen atmosphere to form the contact less. The cured lens has an equilibrium water content of about 30 weight percent. Subsequent to curing, the lens is plasma treated for about 7.5 minutes in an atmosphere of methane and air at a 2:1 $CH_4$:air volume ratio.

The Ionoton Ion Permeability Coefficient of the lens is $0.35\times10^{-3}$ cm$^2$/sec. Clinical examination shows that the lens moves on the human eye. See Table E for a summary of the results.

EXAMPLE E-6

Material B

A contact lens is prepared substantially in accordance with the procedure described in Example B-11. Prior to polymerization, the prepolymerization mixture is degassed by the repeated freeze/thaw procedure of Example E-1.

The prepolymer mixture is cured in a nitrogen atmosphere to form the contact lens. The cured lens has an equilibrium water content of about 30 weight percent. The lens is not subsequently coated.

The Ionoton Ion Permeability Coefficient of the lens is $1.1\times10^{-3}$ cm$^2$/sec. Clinical examination shows that the lens moves on the human eye. See Table E for a summary of the results.

EXAMPLE E-7

Material C

A contact lens is prepared substantially in accordance with the procedure described in Example C-2 1. Prior to polymerization, the prepolymerization mixture is degassed by the repeated freeze/thaw procedure of Example E-1.

The prepolymer mixture is cured in a nitrogen atmosphere to form the contact lens. Subsequent to curing, the lens is plasma treated for about 5 minutes in an atmosphere of methane and air at a 2:1 $CH_4$:air volume ratio.

The Ionoton Ion Permeability Coefficient of the lens is $2.9 \times 10^{-3}$ $cm^2$/sec. Clinical examination shows that the lens moves on the human eye. See Table E for a summary of the results.

EXAMPLE E-8

Material C

A contact lens is prepared substantially in accordance with the procedure described in Example C-21. Prior to polymerization, the prepolymerization mixture is degassed by the repeated freeze/thaw procedure of Example E-1.

The prepolymer mixture is cured in a nitrogen atmosphere to form the contact lens. Subsequent to curing, the lens is plasma treated for about 7.5 minutes in an atmosphere of methane and air at a 2:1 $CH_4$:air volume ratio.

The Ionoton Ion Permeability Coefficient of the lens is $0.25 \times 10^{-3}$ $cm^2$/sec. Clinical examination shows that the lens moves on the human eye. See Table E for a summary of the results.

EXAMPLE E-9

Material C

A contact lens is prepared substantially in accordance with the procedure described in Example C-20. Prior to polymerization, the prepolymerization mixture is degassed by the repeated freeze/thaw procedure of Example E-1.

The prepolymer mixture is cured in an air atmosphere to form the contact lens. Subsequent to curing, the lens is not surface treated.

The Ionoton Ion Permeability Coefficient of the lens is $0.008 \times 10^{-3}$ $cm^2$/sec. Clinical examination shows that the lens does not move on the human eye. See Table E for a summary of the results.

EXAMPLE E-10

Material D

A contact lens is prepared substantially in accordance with the procedure described in Example D-2. Prior to polymerization, the prepolymerization mixture is degassed by the repeated freeze/thaw procedure of Example E-1.

The prepolymer mixture is cured in a nitrogen atmosphere to form the contact lens. Subsequent to curing, the lens is not surface treated.

The Ionoton Ion Permeability Coefficient of the lens is $1.4 \times 10^{-3}$ $cm^2$/sec. Clinical examination shows that the lens moves on the human eye. See Table E for a summary of the results.

EXAMPLE E-11

Material D

A contact lens is prepared substantially in accordance with the procedure described in Example D-2. Prior to polymerization, the prepolymerization mixture is degassed by the repeated freeze/thaw procedure of Example E-1.

The prepolymer mixture is cured in a nitrogen atmosphere to form the contact lens. Subsequent to curing, the lens is plasma treated for about 7.5 minutes in an atmosphere of methane and air at a 2:1 $CH_4$:air volume ratio.

The Ionoton Ion Permeability Coefficient of the lens is $0.61 \times 10^{-3}$ $cm^2$/sec. Clinical examination shows that the lens moves on the human eye. See Table E for a summary of the results.

EXAMPLE E-12

Material D

A contact lens is prepared substantially in accordance with the procedure described in Example D-2. Prior to polymerization, the prepolymerization mixture is degassed by the repeated freeze/thaw procedure of Example E-1.

The prepolymer mixture is cured in a nitrogen atmosphere to form the contact lens. Subsequent to curing, the lens is plasma treated for about 5 minutes in an atmosphere of methane and air at a 2:1 $CH_4$:air volume ratio.

The Ionoton Ion Permeability Coefficient of the lens is $1.5 \times 10^{-3}$ $cm^2$/sec. Clinical examination shows that the lens moves on the human eye. See Table E-I for a summary of the results.

EXAMPLE E-13

Material D

A contact lens is prepared substantially in accordance with the procedure described in Example D-2. Prior to polymerization, the prepolymerization mixture is degassed by the repeated freeze/thaw procedure of Example E-1.

The prepolymer mixture is cured in an air atmosphere to form the contact lens. Subsequent to curing, the lens is not surface treated.

The Ionoton Ion Permeability Coefficient of the lens is $-0.001 \times 10^{-3}$ $cm^2$/sec. Clinical examination shows that the lens does not move on the human eye. See Table E for a summary of the results.

TABLE E

| Example | Material | Degassing | Curing atmosphere | Surface treatment $CH_4$:air plasma [minutes] | Ionoton Ion Permeability Coefficient [$10^{-3}$ $cm^2$/sec] | On-eye Movement |
|---|---|---|---|---|---|---|
| E-1 | A | 3-cycle freeze/thaw | nitrogen | 10 | 0.81 | YES |
| E-2 | B | nitrogen bubble | nitrogen | no plasma | −0.063 | NO |

TABLE E-continued

| Example | Material | Degassing | Curing atmosphere | Surface treatment $CH_4$:air plasma [minutes] | Ionoton Ion Permeability Coefficient [$10^{-3}$ cm$^2$/sec] | On-eye Movement |
|---------|----------|-----------|-------------------|-----------------------------------------------|--------------------------------------------------------------|-----------------|
| E-3 | B | 3-cycle freeze/thaw | nitrogen | 3 | 0.50 | YES |
| E-4 | B | 3-cycle freeze/thaw | nitrogen | 5 | 0.47 | YES |
| E-5 | B | 3-cycle freeze/thaw | nitrogen | 7.5 | 0.35 | YES |
| E-6 | B | 3-cycle freeze/thaw | nitrogen | no plasma | 1.1 | YES |
| E-7 | C | 3-cycle freeze/thaw | nitrogen | 5 | 2.9 | YES |
| E-8 | C | 3-cycle freeze/thaw | nitrogen | 7.5 | 0.25 | YES |
| E-9 | C | 3-cycle freeze/thaw | air | no plasma | 0.008 | NO |
| E-10 | D | 3-cycle freeze/thaw | nitrogen | no plasma | 1.4 | YES |
| E-11 | D | 3-cycle freeze/thaw | nitrogen | 7.5 | 0.61 | YES |
| E-12 | D | 3-cycle freeze/thaw | nitrogen | 5 | 1.5 | YES |
| E-13 | D | 3-cycle freeze/thaw | air | no plasma | −0.001 | NO |

Considering Examples E-1 through E-13 of Table E, the lowest value of Ionoton Ion Permeability Coefficient for which a lens moves on the eye is 0.25×10$^{-3}$ cm$^2$/sec. The highest value of Ionoton Ion Permeability Coefficient for a lens which bound on the eye is 0.008×10$^{-3}$ cm$^2$/sec. Thus, a contact lens preferably has an Ionoton Ion Permeability Coefficient greater than about is 0.008×10$^{-3}$ cm$^2$/sec., more preferably greater than about 0.25×10$^{-3}$ cm$^2$/sec.

EXAMPLE F-1

Material C

A contact lens is prepared substantially in accordance with the procedure described in Example C-25. Prior to surface treatment, the Ionoflux Ion Permeability Coefficient is determined to be about 0 mm$^2$/min.

Subsequent to ion permeability measurements, the lens surface is coated with polyvinylpyrrolidone (PVP) in accordance with the following procedure, using a glass plasma reactor equipped with an external ring electrode and a 27.13 MHz radio frequency (RF) generator for the generation of an inductively-coupled, cold glow discharge plasma. Highly purified argon is used as a plasma gas and as a carrier gas for N-vinylpyrrolidone (NVP) monomer feed. The NVP feed line is located about 10 cm below the glow zone.

The contact lens is placed in the 20 cm diameter plasma reactor at a position about 15 cm below the plasma glow zone. The reactor is then evacuated for about 30 minutes to about 0.009 mbar. Subsequent to evacuation, the plasma gas flow is set to 20 sccm (standard cubic centimeters), the glow discharge is started at a pressure of about 0.15 mbar and maintained for about one minute at a power of about 170 Watts (in order to clean and activate the lens surface). After reduction of argon plasma gas flow to about 10 sccm, the argon carrier gas flow for the NVP monomer is also set to 10 sccm. The temperature of the NVP source (with the carrier gas bubbling through the liquid NVP) is held at about 40° C. The lenses are treated for about 10 minutes with a pulsing glow discharge plasma (1 μsec. on, 3 μsec. off) at about 0.35 mbar pressure and about 150 Watts power.

After interrupting the glow discharge and the carrier gas flow, the reactor is continuously purged with a 20 sccm argon stream at a pressure of about 0.009 mbar for about 30 minutes, in order to remove residual monomer and activated species. The PVP coated contact lenses thus produced are highly wettable and show the following contact dynamic contact angles, measured with a KRUESS (Hamburg, Germany) K-12 instrument:

|  | Untreated | Treated |
|---|---|---|
| Advancing | 102 | 38 |
| Receding | 48 | 23 |
| Hysterisis | 53 | 15 |

Clinical tests show that the lens does not move on the eye. See Table F for a summary of the results.

EXAMPLE F-2

Material C

A contact lens is prepared substantially in accordance with the procedure described in Example C-26. Prior to surface treatment, the Ionoflux Ion Permeability Coefficient is determined to be about 2.8×10$^{-7}$ mm$^2$/min.

Subsequent to ion permeability measurements, the lens surface is coated with polyvinylpyrrolidone as in Example F-1. Clinical tests show that the lens does not move on the eye. See Table F for a summary of the results.

EXAMPLE F-3

Material C

A contact lens is prepared substantially in accordance with the procedure described in Example C-27. Prior to surface treatment, the Ionoflux Ion Permeability Coefficient is determined to be about 9.3×10$^{-7}$ mm$^2$/min.

Subsequent to ion permeability measurements, the lens surface is coated with polyvinylpyrrolidone as in Example F-1. Clinical tests show that the lens does not move on the eye. See Table F for a summary of the results.

EXAMPLE F-4

Material C

A contact lens is prepared substantially in accordance with the procedure described in Example C-18. Prior to surface treatment, the Ionoflux Ion Permeability Coefficient is determined to be about $2.6\times10^{-6}$ mm$^2$/min.

Subsequent to ion permeability measurements, the lens surface is coated with polyvinylpyrrolidone as in Example F-1. Clinical tests show that the lens moves on the eye. See Table F for a summary of the results.

EXAMPLE F-5

Material C

A contact lens is prepared substantially in accordance with the procedure described in Example C-16. Prior to surface treatment, the Ionoflux Ion Permeability Coefficient is determined to be about $1.3\times10^{-5}$ mm$^2$/min.

Subsequent to ion permeability measurements, the lens surface is coated with polyvinylpyrrolidone as in Example F-1. Clinical tests show that the lens moves on the eye. See Table F for a summary of the results.

EXAMPLE F-6

Material C

A contact lens is prepared substantially in accordance with the procedure described in Example C-19. Prior to surface treatment, the Ionoflux Ion Permeability Coefficient is determined to be about $2.7\times10^{-5}$ mm$^2$/min.

Subsequent to ion permeability measurements, the lens surface is coated with polyvinylpyrrolidone as in Example F-1. Clinical tests show that the lens moves on the eye. See Table F for a summary of the results.

EXAMPLE F-7

Material C

A contact lens is prepared substantially in accordance with the procedure described in Example C-17. Prior to surface treatment, the Ionoflux Ion Permeability Coefficient is determined to be about $7.8\times10^{-6}$ mm$^2$/min.

Subsequent to ion permeability measurements, the lens surface is coated with polyvinylpyrrolidone as in Example F-1. Clinical tests show that the lens moves on the eye. See Table F for a summary of the results.

EXAMPLE F-8

Material B

A contact lens is prepared substantially in accordance with the procedure described in Example B-13. Prior to surface treatment, the Ionoflux Ion Permeability Coefficient is determined to be about $1.5\times10^{-6}$ mm$^2$/min.

Subsequent to ion permeability measurements, the lens surface is coated with polyvinylpyrrolidone as in Example F-1. Clinical tests show that the lens does not move on the eye. See Table F for a summary of the results.

EXAMPLE F-9

Material B

A contact lens is prepared substantially in accordance with the procedure described in Example B-14. Prior to surface treatment, the Ionoflux Ion Permeability Coefficient is determined to be about $1.1\times10^{-3}$ mm$^2$/min.

Subsequent to ion permeability measurements, the lens surface is coated with polyvinylpyrrolidone as in Example F-1. Clinical tests show that the lens does not move on the eye. See Table F for a summary of the results.

EXAMPLE F-10

Material B

A contact lens is prepared substantially in accordance with the procedure described in Example B-7. Prior to surface treatment, the Ionoflux Ion Permeability Coefficient is determined to be about $3.8\times10^{-6}$ mm$^2$/min.

Subsequent to ion permeability measurements, the lens surface is coated with polyvinylpyrrolidone as in Example F-1. Clinical tests show that the lens moves on the eye. See Table F for a summary of the results.

EXAMPLE F-11

Material B

A contact lens is prepared substantially in accordance with the procedure described in Example B-6. Prior to surface treatment, the Ionoflux Ion Permeability Coefficient is determined to be about $8.5\times10^{-6}$ mm$^2$/min.

Subsequent to ion permeability measurements, the lens surface is coated with polyvinylpyrrolidone as in Example F 1. Clinical tests show that the lens moves on the eye. See Table F for a summary of the results.

EXAMPLE F-12

Material B

A contact lens is prepared substantially in accordance with the procedure described in Example B-5. Prior to surface treatment, the Ionoflux Ion Permeability Coefficient is determined to be about $7.1\times10^{-5}$ mm$^2$/min.

Subsequent to ion permeability measurements, the lens surface is coated with polyvinylpyrrolidone as in Example F-1. Clinical tests show that the lens moves on the eye. See Table F for a summary of the results.

TABLE F

| EX-AMPLE | MATERIAL (Example reference number) | IONOFLUX ION PERMEABILITY COEFFICIENT* [mm$^2$/min] | ON-EYE MOVEMENT-CLINICAL DETEMINATION |
|---|---|---|---|
| F-1 | C-25 | 0 | NO |
| F-2 | C-26 | $0.28 \times 10^{-6}$ | NO |
| F-3 | C-27 | $0.93 \times 10^{-6}$ | NO |
| F-4 | C-18 | $2.6 \times 10^{-6}$ | YES |
| F-5 | C-16 | $13.0 \times 10^{-6}$ | YES |
| F-6 | C-19 | $27.0 \times 10^{-6}$ | YES |
| F-7 | C-17 | $7.8 \times 10^{-6}$ | YES |
| F-8 | B-13 | $1.5 \times 10^{-6}$ | NO |
| F-9 | B-14 | $1.1 \times 10^{-6}$ | NO |
| F-10 | B-7 | $3.8 \times 10^{-6}$ | YES |
| F-11 | B-6 | $8.5 \times 10^{-6}$ | YES |
| F-12 | B-5 | $71.0 \times 10^{-6}$ | YES |

*All Ionoflux Ion Permeability Coefficients were determined on uncoated lenses.

Considering only Examples F-1 through F-13 of Table F, the lowest value of Ionoflux Ion Permeability Coefficient for which a lens moves on the eye is $2.6\times10^{-6}$ mm$^2$/min. The highest value of Ionoflux Ion Permeability Coefficient for a lens which binds on the eye is $1.5 \times 10^{-6}$ mm$^2$/min. Thus, a contact lens preferably has an Ionoflux Ion Permeability Coefficient greater than about $1.5 \times 10^{-6}$ mm$^2$/min., more preferably greater than about $2.6 \times 10^{-6}$ mm$^2$/min.

EXAMPLE G-1

A contact lens is prepared substantially in accordance with the procedure described in Example A-2. The Hydrodell Water Permeability Coefficient is determined to be about $0.71 \times 10^{-6}$ cm$^2$/second. Clinical tests show that the lens moves on the eye. See Table G for a summary of the results.

EXAMPLE G-2

A contact lens is prepared substantially in accordance with the procedure described in Example B-5. The Hydrodell Water Permeability Coefficient is determined to be about $1.09 \times 10^{-6}$ cm$^2$/second. Clinical tests show that the lens moves on the eye. See Table G for a summary of the results.

EXAMPLE G-3

A contact lens is prepared substantially in accordance with the procedure described in Example B-6. The lens is surface treated in a plasma gas in accordance with the procedure described in Example F-1. The Hydrodell Water Permeability Coefficient is determined to be about $0.27 \times 10^{-6}$ cm$^2$/second. Clinical tests show that the lens moves on the eye. See Table G for a summary of the results.

EXAMPLE G-4

A contact lens is prepared substantially in accordance with the procedure described in Example C-19. The lens is surface treated in a plasma gas in accordance with the procedure described in Example F-1. The Hydrodell Water Permeability Coefficient is determined to be about $0.37 \times 10^{-6}$ cm$^2$/second. Clinical tests show that the lens moves on the eye. See Table G for a summary of the results.

EXAMPLE G-5

A contact lens is prepared substantially in accordance with the procedure described in Example D-2. The Hydrodell Water Permeability Coefficient is determined to be about $1.26 \times 10^{-6}$ cm$^2$/second. Clinical tests show that the lens moves on the eye. See Table G for a summary of the results.

EXAMPLE G-6

A contact lens is prepared substantially in accordance with the procedure described in Example C-14. The Hydrodell Water Permeability Coefficient is determined to be about $0.08 \times 10^{-6}$ cm$^2$/second. Clinical tests show that the lens does not move on the eye. See Table G for a summary of the results.

TABLE G

| EXAMPLE | MATERIAL (Example reference number) | SURFACE TREATMENT | HYDRODELL WATER PERMEABILITY COEFFICIENT [cm$^2$/sec.] | ON-EYE MOVEMENT-CLINICAL DETEMINATION |
|---|---|---|---|---|
| G-1 | A-2 | none | $0.71 \times 10^{-6}$ | YES |
| G-2 | B-5 | none | $1.09 \times 10^{-6}$ | YES |
| G-3 | B-6 | PVP | $0.27 \times 10^{-6}$ | YES |
| G-4 | C-19 | PVP | $0.37 \times 10^{-6}$ | YES |
| G-5 | D-2 | none | $1.26 \times 10^{-6}$ | YES |
| G-6 | C-14 | none | $0.08 \times 10^{-6}$ | NO |

Considering only Examples G-1 through G-6 of Table G, the lowest value of Hydrodell Water Permeability Coefficient for which a lens moves on the eye is $0.27 \times 10^{-6}$ cm$^2$/sec. The highest value of of Hydrodell Water Permeability Coefficient for a lens which binds on the eye is $0.08 \times 10^{-6}$ cm$^2$/sec. Thus, a contact lens preferably has a Hydrodell Water Permeability Coefficient greater than about $0.08 \times 10^{-6}$ cm$^2$/sec., more preferably greater than $0.27 \times 10^{-6}$ cm$^2$/sec.

The invention has been described in detail, with reference to certain preferred embodiments, in order to enable the reader to practice the invention without undue experimentation. Theories of operation have been offered to better enable the reader to understand the invention, but such theories do not limit the scope of the invention. In addition, a person having ordinary skill in the art will readily recognize that many of the previous components, compositions, and parameters may be varied or modified to a reasonable extent without departing from the scope and spirit of the invention. Furthermore, titles, headings, example materials or the like are provided to enhance the reader's comprehension of this document, and should not be read as limiting the scope of the present invention. Accordingly, the intellectual property rights to the invention are defined by the following claims, reasonable extensions and equivalents thereof, as interpretted in view of the disclosure herein.

That which is claimed is:

1. A method for producing an extended wear contact lens, said contact lens comprising a core polymeric material which has a high oxygen permeability and a high ion or water permeability, which method comprises the steps of:

a) preparing a lens formulation comprising an oxyperm polymerizable material selected from the group consisting of fluorine-containing macromers and flourine-containing monomers, and an ionoperm polymerizable material selected from the group consisting of acrylates, methacrylates, polyalkylene glycols and N-vinyl pyrrolidones, wherein said oxyperm polymerizable material comprises between about 30% to about 70%, based on the total weight, of said lens formulation;

b) placing said lens formulation in a lens mold;

c) polymerizing- said lens formulation in said mold to form a lens core material having inner and outer surfaces such that said oxyperm polymerizable material and said ionoperm polymerizable material of said lens formulation form separate oxyperm and ionoperm phases; said lens core material having an oxygen permeability equal to or greater than 77 barrers;

d) removing said lens core material from said lens mold;

e) subjecting said lens core material to a treatment to modify said surfaces of said lens core material, wherein the surface treatment makes said surfaces more biocompatible with the ocular tissue and ocular fluids than said core material alone; and f) hydrating the treated lens core material to produce a hydrated extended wear contact lens, wherein the modified surfaces of said lens in conjunction with the high oxygen and ion permeabilities of said core polymeric material allows said hydrated lens to be worn as extended wear lens that is worn for a continuous period of at least 24 hours with corneal swelling of less than about 8%.

2. The method of claim 1 wherein the surface modification treatment is selected from the group consisting of coating processes, grafting processes, plasma treating processes, electrical charge treating processes and irradiation processes.

3. The method of claim 1 wherein the surface modification treatment is a plasma treating process.

4. The method of claim 3 wherein said oxyperm polymerizable material is a fluorine-containing macromer and said ionoperm polymerizable material is N-vinyl pyrrolidone.

5. An extended wear contact lens comprising a core polymeric material and upper and lower surfaces, said core polymeric material comprising a silicone copolymer which provides a high ion permeability and a high oxygen permeability; wherein said silicone copolymer comprises an oxyperm polymerizable material selected from the group consisting of fluorine-containing macromers and fluorine-containing monomers, and an ionoperm polymerizable material selected from the group consisting of acrylates, methacrylates, polyalkylene glycols and N-vinyl pyrrolidones; said core polymeric material having an oxygen permeability equal to or greater than 77 barrers; wherein said surfaces are hydrophilically modified by a treatment process selected from the group consisting of coating processes, grafting processes, plasma treating processes, electrical charge treating processes and irradiation processes; and wherein said extended wear contact lens can be continuously worn for at least four days on a human eye without substantial corneal swelling.

6. The extended contact lens of claim 5 wherein said core polymeric material comprises a fluorine containing macromer, and N-vinyl pyrrolidone.

7. The extended contact lens of claim 6 wherein said surfaces are modified by a plasma treating process.

8. The extended contact lens of claim 7 wherein said extended lens can be continuously worn for about 7 days with less than about 8% corneal swelling.

9. The extended contact lens of claim 5 wherein said wended lens is worn for about 30 days.

10. A hydrogel contact lens having modified surfaces, said hydrogel contact lens comprising a core polymeric material having an oxygen permeability equal to or greater than 77 barrers, said hydrogel contact lens being suited to make contact with ocular tissue and ocular fluids and having a high oxygen permeability and a high ion permeability, said core polymeric material having formed from polymerizable materials comprising:

(a) an oxyperm polymerizable material selected from the group consisting of fluorine-containing macromers and fluorine-containing monomers, and (b) an ionoperm polymerizable material selected from the group consisting of acrylates, methacrylates, polyalkylene glycols and N-vinyl pyrrolidones, wherein said lens has a high oxygen permeability and allows ion or water permeation in an amount sufficient to enable the lens to move on the eye such that corneal health is not substantially harmed and wearer comfort is acceptable during a period of continuous contact with ocular tissue and ocular fluids, wherein said lens has an oxygen permeability of at least about 77 barrers and an ion permeability characterized either by an Ionoflux Ion Diffusion Coefficient of grater than about $6.4\times10^{-6}$ $mm^2$/sec or an Ionoton Ion Permeability Coefficient of greater than about $0.4\times10^{-6}$ $cm^2$/min, wherein said modified surfaces are hydrophilically modified surfaces that are modified by a treatment process selected from the group consisting of coating processes, grafting processes, plasma treating processes, electrical charge treating processes and irradiation processes, wherein said hydrogel contact lens is adapted for at least 24 hours of continuous wear on a human eye without substantial corneal swelling.

11. The hydrogel contact lens of claim 10 wherein said core polymeric material comprises a fluorine containing macromer as said oxyperm material and N-vinyl pyrrolidone as said ionoperm material.

12. The hydrogel contact lens of claim 11 wherein said surfaces are modified by a plasma treating process.

13. The hydrogel contact lens of claim 12 wherein said lens can be worn for about 7 days with less than about 8% corneal swelling.

14. The hydrogel contact lens of claim 12 wherein said lens is worn for about 7 days with less than about 4% corneal swelling.

15. The hydrogel contact lens of claim 12 wherein said lens can be continuously worn for about 30 days.

16. The hydrogel contact lens of claim 12 wherein said lens has an oxygen permeability of at least about 81 barrers.

17. A method of using a contact lens as an extended wear lens, said lens having ophthalmically compatible modified surfaces, said lens being suited to extended periods of wear in continuous, intimate contact with ocular tissue and ocular fluids, said lens comprising a polymeric material which has a high oxygen permeability and a high ion or water permeability, and which has an oxygen permeability equal to or greater than 77 barrers, said polymeric material being formed from polymerizable materials comprising:

(a) an oxyperm polymerizable material selected from the group consisting of fluorine-containing macromers and fluorine-containing monomers, and (b) an ionoperm polymerizable material selected from the group consisting of acrylates, methacrylates, polyalkylene glycols and N-vinyl pyrrolidones, wherein said modified surfaces are modified by a treatment process selected from the group consisting of coating processes, grafting processes, plasma treating processes, electrical charge treating processes and irradiation processes;

wherein said lens allows oxygen permeation in an amount sufficient to maintain corneal health and wearer comfort during a period of extended, continuous contact with ocular tissue and ocular fluids;

wherein said lens allows ion or water permeation in an amount sufficient to enable the lens to move on the eye such that corneal health is not substantially harmed and wearer comfort is acceptable during a period of extended, continuous contact with ocular tissue and ocular fluids; and wherein said ophthalmic lens has an oxygen permeability of at least about 70 barrers and an ion permeability characterized either by (1) an Ionoton Ion Permeability Coefficient of greater than about $0.4\times10^{-6}$ $cm^2$/sec or (2) an Ionoflux Diffusion Coefficient of greater than about 6.4×10−6 mm²/min, wherein said ion permeability is measured with respect to sodium ions;

said method comprising the steps of:
(a) applying said lens to the ocular environment, and
(b) allowing said lens to remain in intimate contact with the ocular environment for a period of at least 24 hours.

18. The method of claim 17 wherein said lens has an oxygen permeability of at least about 81 barrers.

19. The method of claim 17 wherein said intimate contact period is at least 4 days.

20. The method of claim 17 wherein said intimate contact period is about 7 days.

21. The method of claim 17 wherein said intimate contact period is about 14 days.

22. The method of claim 17 wherein said intimate contact period is about 30 days.

23. The method of claim 17 wherein said lens produces, after wear of about 24 hours, including normal steep periods, less than about 8% corneal swelling.

24. The method of claim 17 wherein said lens produces, after wear of about 7 days, including normal sleep periods, less than about 6% corneal swelling.

25. A method for producing an extended wear contact lens, said contact lens comprising a core polymeric material which has a high oxygen permeability and a high ion or water permeability, which method comprises the steps of:
a) preparing a lens formulation comprising an oxyperm polymerizable material, and an ionoperm polymerizable material, wherein said oxyperm polymerizable material comprises between about 30% to about 70%, based on the total weight, of said lens formulation;
b) placing said lens formulation in a lens mold;
c) polymerizing said lens formulation in said mold to form a lens core material having inner and outer surfaces such that said oxyperm polymerizable material and said ionoperm polymerizable material of said lens formulation form separate oxyperm and ionoperm phases; said lens core material having an oxygen permeability equal to or greater than 69 barrers;
d) removing said lens core material from said lens mold;
e) subjecting said lens core material to a treatment to modify said surfaces of said lens core material, wherein the surface treatment makes said surfaces more hydrophilic or lipophobic and more biocompatible with the ocular tissue than said core material alone; and
f) hydrating the treated lens core material to produce a hydrated extended wear contact lens,
wherein the modified surfaces of said lens in conjunction with the high oxygen and ion permeabilities of said core polymeric material allows said hydrated lens to be worn as extended wear lens that is worn for a continuous period of at least 24 hours without having substantial amounts of lipid adsorption.

26. The method of claim 25 wherein the surface modification treatment is selected from the group consisting of coating processes, grafting processes, plasma treating processes, electrical charge treating processes and irradiation processes.

27. The method of claim 25 wherein the surface modification treatment is a plasma treating process.

28. The method of claim 27 wherein said oxyperm polymerizable material is a fluorine macromer and said ionoperm polymerizable material is N-vinyl pyrrolidone.

29. An-extended wear contact lens comprising a core polymeric material and upper and lower surfaces, said core polymeric material comprising a silicone copolymer which provides a high ion permeability and a high oxygen permeability; said silicone copolymer comprising an oxyperm polymerizable material, and an ionoperm polymerizable material; said core polymeric material having an oxygen permeability equal to or greater than 69 barrers; wherein said surfaces are hydrophilically modified by a treatment process selected from the group consisting of coating processes, grafting processes, plasma treating processes, electrical charge treating processes and irradiation processes; and wherein said extended wear contact lens can be continuously worn for at least four days on a human eye without substantial corneal swelling and without having substantial amounts of lipid adsorption.

30. The extended contact lens of claim 29 wherein said core polymeric material comprises a fluorine macromer, and N-vinyl pyrrolidone.

31. The extended contact lens of claim 30 wherein said surfaces are modified by a plasma treating process.

32. The extended contact lens of claim 31 wherein said extended lens can be continuously worn for about 7 days with less than about 7% corneal swelling.

33. The extended contact lens of claim 29 wherein said extended wear lens can be worn for about 30 days.

34. A siloxane hydrogel contact lens having modified surfaces, said hydrogel contact lens comprising a core polymeric material having an oxygen permeability equal to or greater than 69 barrers, said hydrogel contact lens being suited to make contact with ocular tissue and ocular fluids and having a high oxygen permeability and a high ion permeability, said core polymeric material being formed from polymerizable materials comprising:
(a) an oxyperm polymerizable material, and
(b) an ionoperm polymerizable material, wherein said lens has a high oxygen permeability and allows ion or water permeation in an amount sufficient to enable the lens to move on the eye such that corneal health is not substantially harmed and wearer comfort is acceptable during a period of continuous contact with ocular tissue and ocular fluids, wherein said lens has an oxygen permeability of at least about 69 barrers and an ion permeability characterized either by an Ionoflux Ion Diffusion Coefficient of greater than about 6.4×10−6 mm²/sec or an Ionoton Ion Permeability Coefficient of greater than about 0.4×10−6 cm²/min,
wherein said modified surfaces are hydrophilically modified surfaces that are modified by a treatment process selected from the group consisting of coating processes, grafting processes, plasma treating processes, electrical charge treating processes and irradiation processes,
wherein said hydrogel contact lens is adapted for at least 24 hours of continuous wear on a human eye without substantial corneal swelling and without having substantial amounts of lipid adsorption.

35. The hydrogel contact lens of claim 34 wherein said core polymeric material comprises a fluorine containing macromer as said oxyperm material and N-vinyl pyrrolidone as said ionoperm material.

36. The hydrogel contact lens of claim 35 wherein said surfaces are modified by a plasma treating process.

37. The hydrogel contact lens of claim 36 wherein said lens can be worn for about 7 days in continuous contact with ocular tissues and fluids with less than about 8% corneal swelling.

38. The hydrogel contact lens of claim 36 wherein said lens is worn for about 7 days with less than about 4% corneal swelling.

39. The hydrogel contact lens of claim 36 wherein said lens can be continuously worn for about 30 days.

40. The hydrogel contact lens of claim 36 wherein said lens has an oxygen permeability of at least about 77 barrers.

41. A method of using a contact lens as an extended wear lens, said lens having ophthalmically compatible modified surfaces, said lens being suited to extended periods of wear in continuous, intimate contact with ocular tissue and ocular fluids, said lens comprising a polymeric material which has a high oxygen permeability and a high ion or water permeability, and which has an oxygen permeability equal to or greater than 69 barrers, said polymeric material being formed from polymerizable materials comprising:
  (a) an oxyperm polymerizable material, and
  (b) an ionoperm polymerizable material,
  wherein said modified surfaces are modified by a treatment process selected from the group consisting of coating processes, grafting processes, plasma treating processes, electrical charge treating processes and irradiation processes;
  wherein said lens allows oxygen permeation in an amount sufficient to maintain corneal health and wearer comfort during a period of extended, continuous contact with ocular tissue and ocular fluids;
  wherein said lens allows ion or water permeation in an amount sufficient to enable the lens to move on the eye such that corneal health is not substantially harmed and wearer comfort is acceptable during a period of extended, continuous contact with ocular tissue and ocular fluids without having substantial amounts of lipid absorption; and
  wherein said ophthalmic lens has an oxygen permeability of at least about 70 barrers and an ion permeability characterized either by (1) an Ionoton Ion Permeability Coefficient of greater than about 0.4×10–6 cm$^2$/sec or (2) an Ionoflux Diffusion Coefficient of greater than about 6.4×10–6 mm$^2$/min, wherein said ion permeability is measured with respect to sodium ions;
  said method comprising the steps of:
    (a) applying said lens to the ocular environment, and
    (b) allowing said lens to remain in continuous intimate contact with the ocular environment for a period of at least 24 hours without having substantial amounts of lipid adsorption.

42. The method of claim 41 wherein said lens has an oxygen permeability of at least about 77 barrers.

43. The method of claim 41 wherein said intimate contact period is at least 4 days.

44. The method of claim 41 wherein said intimate contact period is about 7 days.

45. The method of claim 41 wherein said intimate contact period is about 14 days.

46. The method of claim 41 wherein said intimate contact period is about 30 days.

47. The method of claim 41 wherein said lens produces, after wear of about 24 hours, including normal steep periods, less than about 8% corneal swelling.

48. The method of claim 41, wherein said lens produces, after wear of about 7 days, including normal sleep periods, less than about 6% corneal swelling.

49. A method of forming a biocompatible lens having high oxygen permeability and high water permeability, said method comprising the steps of:
  (a) forming a polymeric core formulation comprising an oxyperm polymerizable material, and an ionoperm polymerizable material, said oxyperm polymerizable material comprises between about 30% to about 70%, based on the total weight, of said lens formulation;
  (b) polymerizing the core in an atmosphere substantially free from oxygen;
  (c) altering the surface of said core material to produce a surface which is more hydrophilic than said core material; and
  (d) autoclaving lens at predetermined temperatures;
  whereby said lens allows oxygen permeation in an amount sufficient to maintain corneal health and wearer comfort during a period of extended, continuous contact with ocular tissue and ocular fluids, and
  whereby said lens allows ion permeation in an amount sufficient to enable the lens to move on the eye such that corneal health is not substantially harmed and wearer comfort is acceptable during a period of extended, continuous contact with ocular tissue and ocular fluids,
  wherein said lens having adequate movement on the eye with blinking to promote adequate tear exchange and without producing significant corneal swelling, without having substantial amounts of lipid adsorption, and without causing substantial wearer discomfort during the period of contact for at least 24 hours,
  wherein said ophthalmic lens has an oxygen transmissibility of at least about 70 barrers/mm and an ion permeability characterized either by (1) an Ionoton Ion Permeability Coefficient of greater than about 0.2×10$^{-6}$ cm$^2$/sec or (2) by an Ionoflux Ion Permeability Coefficient of greater than about 1.5×10$^{-6}$ mm$^2$/min, wherein said ion permeability is measured with respect to sodium ions.

50. A method of forming a contact lens having high oxygen permeability and high water permeability, said method comprising:
  (a) forming a polymeric core material in the shape of a contact lens having an inner and outer surface; and
  (b) altering the surfaces of said core material to produce new surfaces that are more hydrophilic than said core material,
  wherein said lens having adequate movement on the eye with blinking to promote adequate tear exchange and without producing significant corneal swelling, without having substantial amounts of lipid adsorption, and without causing substantial wearer discomfort during the period of contact for at least 24 hours.

51. The method of claim 50 wherein said intimate contact period is about 7 days.

52. The method of claim 50 wherein said intimate contact period is about 30 days.

53. The method of claim 50 wherein said lens is autoclaved at predetermined temperatures.

54. A biocompatible contact lens having high oxygen permeability and high water permeability, said lens comprising:
  (a) a polymeric core material in the shape of a contact lens having an inner and outer surface; and
  (b) said surfaces of said core material being surface modified to produce new surfaces that are more hydrophilic than said core material,
  wherein said lens having adequate movement on the eye with blinking to promote adequate tear exchange and without producing significant corneal swelling, without having substantial amounts of lipid adsorption, and without causing substantial wearer discomfort during the period of contact for at least 24 hours.

55. The lens of claim 54 wherein said intimate contact period is at least 4 days.

56. The lens of claim 55 wherein said intimate contact period is about 7 days.

57. The lens of claim 55 wherein said intimate contact period is about 14 days.

58. The lens of claim 55 wherein said intimate contact period is about 30 days.

59. The lens of claim 54 including (c) said said lens being autoclaved at predetermined temperatures.

60. A method for producing an extended wear contact lens, said contact lens comprising a core polymeric material which has a high oxygen permeability and a high ion or water permeability, which method comprises the steps of:
   a) preparing a lens formulation comprising an oxyperm polymerizable material, and an ionoperm polymerizable material, wherein said oxyperm polymerizable material comprises between about 30% to about 70%, based on the total weight, of said lens formulation;
   b) placing said lens formulation in a lens mold;
   c) polymerizing said lens formulation in said mold to form a lens core material having inner and outer surfaces such that said oxyperm polymerizable material and said ionoperm polymerizable material of said lens formulation form separate oxyperm and ionoperm phases; said lens core material having an oxygen permeability equal to or greater than 69 barrers;
   d) removing said lens core material from said lens mold;
   e) subjecting said lens core material to a treatment to modify said surfaces of said lens core material, wherein the surface treatment makes said surfaces more hydrophilic or lipophobic and more biocompatible with the ocular tissue than said core material alone; and
   f) hydrating the treated lens core material to produce a hydrated extended wear contact lens,
   wherein the modified surfaces of said lens in conjunction with the high oxygen and ion permeabilities of said core polymeric material allows said hydrated lens to be worn as extended wear lens that is worn for a continuous period of at least 24 hours without having substantial amounts of lipid adsorption.

61. A method for producing an extended wear contact lens, said contact lens comprising a core polymeric material which has a high oxygen permeability and a high ion or water permeability, which method comprises the steps of:
   a) preparing a lens formulation comprising an oxyperm polymerizable material selected from the group consisting of siloxane-containing macromers, fluorine-containing macromers and fluorine monomers, and an ionoperm polymerizable material, wherein said oxyperm polymerizable material comprises between about 30% to about 70%, based on the total weight, of said lens formulation;
   b) placing said lens formulation in a lens mold;
   c) polymerizing said tens formulation in said mold to form a lens core material having inner and outer surfaces such that said oxyperm polymerizable material and said ionoperm polymerizable material of said lens formulation form separate oxyperm and ionoperm phases; said lens core material having at least one continous pathway from said inner surface to said outer surface for oxygen transmission therethrough;
   d) removing said lens core material from said lens mold;
   e) subjecting said lens core material to a treatment to modify said surfaces of said lens core material, wherein the surface treatment makes said surfaces more hydrophilic or lipophobic and more biocompatible with the ocular tissue than said core material alone; and
   f) hydrating the treated lens core material to produce a hydrated extended wear contact lens,
   wherein the modified surfaces of said lens in conjunction with the high oxygen and ion permeabilities of said core polymeric material allows said hydrated lens to be worn as extended wear lens that is worn for a continuous period of at least 24 hours with corneal swelling of less than about 8%.

62. The method of claim 61 wherein the surface modification treatment is selected from the group consisting of coating processes, grafting processes, plasma treating processes, electrical charge treating processes and irradiation processes.

63. The method of claim 61 wherein the surface modification treatment is a plasma treating process.

64. The method of claim 63 wherein said oxyperm polymerizable material is a siloxane containing macromer or siloxane containing monomer and said ionoperm polymerizable material is N-vinyl pyrrolidone.

65. An extended wear contact lens comprising a core polymeric material and upper and lower surfaces, said core polymeric material comprising a silicone copolymer which provides a high ion permeability and a high oxygen permeability; wherein said silicone copolymer comprises an oxyperm polymerizable material selected from the group consisting of siloxane-containing macromers, siloxane-containing monomers, fluorine- containing macromers, siloxane containing monomers and fluorine-containing monomers, and an ionoperm polymerizable material selected from the group consisting of acrylates, methacrylates, polyalkylene glycols and N-vinyl pyrrolidones, wherein said core polymeric material has at least one continuous pathway from said upper surface to said lower surface for oxygen transmission;
   wherein said surfaces are hydrophilically modified by a treatment process selected from the group consisting of coating processes, grafting processes, plasma treating processes, electrical charge treating processes and irradiation processes; and wherein said extended wear contact lens can be continuously worn for at least four days on a human eye without substantial corneal swelling.

66. The extended contact lens of claim 65 wherein said core polymeric material comprises a siloxane-containing macromer or a siloxane monomer, and N-vinyl pyrrolidone.

67. The extended contact lens of claim 66 wherein said surfaces are modified by a plasma treating process.

68. The extended contact lens of claim 67 wherein said extended lens can be continuously worn for about 7 days with less than about 8% corneal swelling.

69. The extended contact lens of claim 66 wherein said extended wear lens can be worn for about 30 days.

70. A hydrogel contact lens having modified surfaces, said hydrogel contact lens comprising a core polymeric material having at least one continuous pathway between said surfaces for oxygen transmission therethrough, said hydrogel contact lens being suited to make contact with ocular tissue and ocular fluids and having a high oxygen permeability and a high ion permeability, said core polymeric material having formed from polymerizable materials comprising:
   (a) an oxyperm polymerizable material selected from the group consisting of siloxane-containing macromers, siloxane-containing monomers, fluorine-containing macromers and fluorine-containing monomers, and (b) an ionoperm polymerizable material selected from the group consisting of acrylates, methacrylates, polyalkylene glycols and N-vinyl pyrrolidones, wherein said lens has a high oxygen permeability and allows ion or water permeation in an amount sufficient to enable the lens to move on the eye such that corneal health is not substantially harmed and wearer comfort is acceptable during a period of continuous contact with ocular tissue and ocular fluids, wherein said lens has an oxygen permeability of at least about 70 barrers and an ion permeability characterized either by an Ionoflux Ion Diffusion Coefficient of grater than about $6.4 \times 10^{-6}$ mm$^2$/sec or an Ionoton Ion Permeability Coefficient of greater than about $0.4 \times 10^{-6}$ cm$^2$/min, wherein said modified surfaces are hydrophilically modified surfaces that are modified by a treatment process selected from the group consisting of coating processes, grafting processes, plasma treating processes, electrical charge treating processes and irradiation processes, wherein said hydrogel contact lens is adapted for at least 24 hours of continuous wear on a human eye without substantial corneal swelling.

71. The hydrogel contact lens of claim 70 wherein said core polymeric material comprises a siloxane-containing macromer or a siloxane containing monomer as said oxyperm material and N-vinyl pyrrolidone as said ionoperm material.

72. The hydrogel contact lens of claim 71 wherein said surfaces are modified by a plasma treating process.

73. The hydrogel contact lens of claim 72 wherein said lens can be worn for about 7 days with less than about 8% corneal swelling.

74. The hydrogel contact lens of claim 72 wherein said lens is worn for about 7 days with less than about 4% corneal swelling.

75. The hydrogel contact lens of claim 72 wherein said lens can be continuously worn for about 30 days.

76. The hydrogel contact lens of claim 72 wherein said lens has an oxygen permeability of at least 75 days.

77. A method of using a contact lens as an extended wear lens, said lens having ophthalmically compatible modified surfaces, said lens being suited to extended periods of wear in continuous, intimate contact with ocular tissue and ocular fluids, said lens comprising a polymeric material which has a high oxygen permeability and a high ion or water permeability, and which has at least one continous pathway between said modified surfaces for oxygen surfaces, said polymeric material being formed from polymerizable materials comprising:

(a) an oxyperm polymerizable material, and (b) an ionoperm polymerizable material, wherein said modified surfaces are modified by a treatment process selected from the group consisting of coating processes, grafting processes, plasma treating processes, electrical charge treating processes and irradiation processes;

wherein said lens allows oxygen permeation in an amount sufficient to maintain corneal health and wearer comfort during a period of extended, continuous contact with ocular tissue and ocular fluids;

wherein said lens allows ion or water permeation in an amount sufficient to enable the lens to move on the eye such that corneal health is not substantially harmed and wearer comfort is acceptable during a period of extended, continuous contact with ocular tissue and ocular fluids without having substantial amounts of lipid absorption; and wherein said ophthalmic lens has an oxygen permeability of at least about 70 barrers and an ion permeability characterized either by (1) an Ionoton Ion Permeability Coefficient of greater than about $0.4 \times 10^{-6}$ cm$^2$/sec or (2) an Ionoflux Diffusion Coefficient of greater than about $6.4 \times 10^{-6}$ mm$^2$/min, wherein said ion permeability is measured with respect to sodium ions;

said method comprising the steps of:
  (a) applying said lens to the ocular environment, and
  (b) allowing said lens to remain in continous intimate contact with the ocular environment for a period of at least 24 hours.

78. The method of claim 77 wherein said lens has an oxygen permeability of at least about 77 barrers.

79. The method of claim 77 wherein said intimate contact period is at least 4 days.

80. The method of claim 77 wherein said intimate contact period is about 7 days.

81. The method of claim 77 wherein said intimate contact period is about 14 days.

82. The method of claim 77 wherein said intimate contact period is about 30 days.

83. The method of claim 77, wherein said lens produces, after wear of about 24 hours, including normal steep periods, less than about 8% corneal swelling.

84. The method of claim 77, wherein said lens produces, after wear of about 7 days, including normal sleep periods, less that about 6% corneal swelling.

* * * * *

UNITED STATES PATENT AND TRADEMARK OFFICE
CERTIFICATE OF CORRECTION

PATENT NO. : 6,951,894 B1
DATED : October 4, 2005
INVENTOR(S) : Nicolson et al.

It is certified that error appears in the above-identified patent and that said Letters Patent is hereby corrected as shown below:

Column 70,
Line 55, change "polymerizing-said" to -- polymerizing said --.

Column 71,
Line 21, change "material and upper" to -- material having upper --.

Column 72,
Line 4, change "of grater than" to -- of greater than --.
Line 4, change "6.4x10-6" to -- $6.4 \times 10^{-6}$ --.
Lines 6 and 65, change "0.4x10-6" to -- $0.4 \times 10^{-6}$ --.

Column 73,
Line 1, change "6.4x10-6" to -- $6.4 \times 10^{-6}$ --.

Column 74,
Line 43, change "6.4x10-6" to -- $6.4 \times 10^{-6}$ --.
Line 45, change "0.4x10-6" to -- $0.4 \times 10^{-6}$ --.

Column 75,
Line 35, change "0.4x10-6" to -- $0.4 \times 10^{-6}$ --.
Line 37, change "6.4x10-6" to -- $6.4 \times 10^{-6}$ --.

Column 76,
Lines 3 and 4, change "(b) polymerizing the core in an atmosphere substantially free from oxygen" to -- (b) polymerizing the core formulation in an atmosphere substantially free from oxygen to form a biocompatible lens having a core and surfaces; --.
Line 8, change "autoclaving lens" to -- autoclaving said lens --.
Line 25, change "wherein said ophthalmic lens" to -- wherein said biocompatible lens --.

Column 77,
Line 39, change "worn as extended wear lens that is worn for" to -- worn as an extended wear lens for --.
Line 61, change "continous" to -- continuous --.

Column 78,
Line 9, change "worn as extended wear lens that is worn for" to -- worn as an extended wear lens for --.

Column 79,
Line 12, change "6.4x10-6" to -- $6.4 \times 10^{-6}$ --.
Line 14, change "0.4x10-6" to -- $0.4 \times 10^{-6}$ --.
Line 47, change "continous" to -- continuous --.

UNITED STATES PATENT AND TRADEMARK OFFICE
CERTIFICATE OF CORRECTION

PATENT NO.    : 6,951,894 B1
DATED         : October 4, 2005
INVENTOR(S)   : Nicolson et al.

It is certified that error appears in the above-identified patent and that said Letters Patent is hereby corrected as shown below:

Column 80,
Line 18, change "absorption" to -- adsorption --.
Line 22, change "0.4x10-6" to -- $0.4 \times 10^{-6}$ --.
Line 24, change "6.4x10-6" to -- $6.4 \times 10^{-6}$ --.
Line 28, change "continous" to -- continuous --.
Line 49, change "less that about" to -- less than about --.
After line 49, add the following claims:

85. An extended wear contact lens comprising a core polymeric material and inner and outer surfaces that are more hydrophilic than said core polymeric material, said core polymeric material formed from a silicone copolymer which provides a high ion permeability and a high oxygen permeability; said silicone copolymer comprising an oxyperm polymerizable material, and an ionoperm polymerizable material; said core polymeric material having an oxygen permeablility equal to or greater than 69 barrers; wherein said extended wear contact lens can be continuously worn for at least fourteen days on a human eye without substantial corneal swelling and without having substantial amounts of lipid adsorption.

86. A siloxane hydrogel contact lens comprising a core polymeric material having hydrophilically modified surfaces that are more hydrophilic that said core material, said hydrogel contact lens being suited to make contact with ocular tissue and ocular tissue and ocular fluids, said core polymeric material being formed from polymerizable materials comprising:
    (a) an oxyperm polymerizable material, and
    (b) an ionoperm polymerizable material,
wherein said lens has an oxygen permeability of at least about 69 barrers and an ion permeability characterized either by an Ionoflux Ion Diffusion Coefficient of greater than about $6.4 \times 10^{-6}$ $mm^2$/sec or an Ionoton Ion Permeability Coefficient of greater than about $0.4 \times 10^{-6}$ $cm^2$/min to enable the lens to move on the eye such that corneal health is not substantially harmed and wearer comfort is acceptable during a period of continuous contact with ocular tissue and ocular fluids, wherein said hydrogel contact lens is adapted for at least 14 days of continuous wear on a human eye without substantial corneal swelling and without having substantial amounts of lipid adsorption.

87. A biocompatible contact lens having an oxygen permeability of at least about 69 barrers and an ion permeability characterized by an Ionoton Ion Permeability Coefficient of greater than about $0.4 \times 10^{-6}$ $cm^2$/min, said lens comprising:
    (a) a polmeric core material in the shape of contact lens having an inner and outer surface; and
    (b) said surface of said core material being surface treated to form surfaces that are more hydrophilic than said core material;

UNITED STATES PATENT AND TRADEMARK OFFICE
CERTIFICATE OF CORRECTION

| | |
|---|---|
| PATENT NO. | : 6,951,894 B1 |
| DATED | : October 4, 2005 |
| INVENTOR(S) | : Nicolson et al. |

It is certified that error appears in the above-identified patent and that said Letters Patent is hereby corrected as shown below:

88. A biocompatible sterilizable contact lens having an oxygen permeability of at least about 69 barrers and an ion permeability characterized by an Ionoton Ion Permeability Coefficient of greater than about $0.4 \times 10^{-6}$ $cm^2$/min, said lens comprising:
    (a) a polymeric core material in the shape of contact lens having an inner and outer surface; and
    (b) said surfaces of said core material being surface modified to form surfaces that are more hydrophilic than said core material;
said lens having adequate movement on the eye without blinking to promote adequate tear exchange and without producing significant corneal swelling, without having substantial lipid adsorption, and without causing substantial wearer discomfort for a period of continuous contact for 30 days.

89. A contact lens comprising a polymeric material formed from at least:
    (a) an ionoperm polymerizable material comprising at least one of 2-hydroxyethyl methacrylate or N,N-dimethylacrylamide; and
    (b) an oxyperm polymerizable material;
wherein said lens has an oxygen transmissibility of at least about 70 barrers/mm and an ion permeability characterized either by (1) an Ionoton ion permeabity coefficient of greater than about $0.25 \times 10^{-3}$ $cm^2$/sec, or (2) an Ionoflux diffusion coefficient of greater than about $1.3 \times 10^{-5}$ $mm^2$/min, wherein said ion permeability is measured with respect to sodium ions;
wherein said lens is suitable for continuous, intimate contact with ocular tissue and ocular fluids while having adequate movement on the eye with blinking to promote adequate tear exchange and without producing significant corneal swelling, without having substantial amounts of lipid adsorption, and without causing substantial wearer discomfort during a period of wear of at least 24 hours.

90. The contact lens of claim 89 wherein said ionoperm polymerizable material comprises both 2-hydroxyethyl methacrylate and N,N-dimethylacrylamide.

91. The contact lens of claim 90 wherein said oxyperm polymerizable material comprises at least one of a siloxane containing macromer or a siloxane containing monomer.

92. The contact lens of claim 91 wherein said polymeric material is further formed from ethylene glycol dimethacrylate.

93. The contact lens of claim 92 wherein said lens is autoclaved without lowering either said oxygen transmissibility or said ion permeability below levels sufficient to maintain good corneal health and on-eye movement.

94. The contact lens of claim 92 wherein said period of wear is at least 4 days.

95. The contact lens of claim 92 wherein said period of wear is at least 7 days.

96. The contact lens of claim 89 further comprising polyvinylpyrrolidone at a surface of said lens.

UNITED STATES PATENT AND TRADEMARK OFFICE
CERTIFICATE OF CORRECTION

PATENT NO.   : 6,951,894 B1
DATED        : October 4, 2005
INVENTOR(S)  : Nicolson et al.

It is certified that error appears in the above-identified patent and that said Letters Patent is hereby corrected as shown below:

97. The contact lens of claim 96 wherein said polyvinylpyrrolidone coats said surface of said lens.
98. The contact lens of claim 89 wherein said period of wear is at least 4 days.
99. The contact lens of claim 89 wherein said period of wear is at least 7 days.
100. The contact lens of claim 89 wherein said lens has an equilibrium water content of about 10 to about 30 weight percent.

Signed and Sealed this

Twenty-first Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,951,894 B1
APPLICATION NO. : 09/640526
DATED : October 4, 2005
INVENTOR(S) : Nicolson et al.

It is certified that error appears in the above-identified patent and that said Letters Patent is hereby corrected as shown below:

In column 73, line 62, please change "treatment is a" to --treatment includes a--

In column 73, lines 63-65, please change "wherein said oxyperm polymerizable material is a fluorine macromer and said ionoperm polymerizable material" to --wherein said ionoperm polymerizable material--.

In column 74, line 16, please change "material comprises a fluorine macromer, and" to --material is formed from--.

In column 77, lines 9 and 10, please change "54 including (c) said said lens being autoclaved at predetermined temperatures." to --54, said lens being sterilized.--

Signed and Sealed this

Third Day of October, 2006

JON W. DUDAS
*Director of the United States Patent and Trademark Office*

(12) EX PARTE REEXAMINATION CERTIFICATE (8967th)
United States Patent
Nicolson et al.

(10) Number: US 6,951,894 C1
(45) Certificate Issued: *Apr. 17, 2012

(54) EXTENDED WEAR OPHTHALMIC LENS

(75) Inventors: Paul Clement Nicolson, Dunwoody, GA (US); Richard Carlton Baron, Alpharetta, GA (US); Peter Chabrecek, Basel (CH); John Court, Ultimo (AU); Angelika Domschke, Lörrach (DE); Hans Jörg Griesser, The Patch (AU); Arthur Ho, Randwick (AU); Jens Höpken, Lörrach (CH); Bronwyn Glenice Laycock, Heidelberg Heights (AU); Qin Liu, Duluth, GA (US); Dieter Lohmann, Munchestein (CH); Gordon Francis Meijs, Murrumbeena (AU); Eric Papaspiliotopoulos, Paddington (AU); Judy Smith Riffle, Blacksburg, VA (US); Klaus Schindhelm, Cherrybrook (AU); Deborah Sweeney, Roseville (AU); Wilson Leonard Terry, Jr., Alpharetta, GA (US); Jürgen Vogt, Fribourg (CH); Lynn Cook Winterton, Alpharetta, GA (US)

(73) Assignee: CIBA Vision Corporation, Duluth, GA (US)

Reexamination Request:
No. 90/010,896, Apr. 14, 2010

Reexamination Certificate for:
Patent No.: 6,951,894
Issued: Oct. 4, 2005
Appl. No.: 09/640,526
Filed: Aug. 17, 2000

(*) Notice: This patent is subject to a terminal disclaimer.

Certificate of Correction issued Mar. 21, 2006.

Related U.S. Application Data

(63) Continuation of application No. 09/262,542, filed on Mar. 4, 1999, now abandoned, which is a continuation of application No. 09/108,714, filed on Jul. 1, 1998, now Pat. No. 5,965,631, which is a division of application No. 08/682,452, filed on Jul. 17, 1996, now Pat. No. 5,849,811, which is a division of application No. 08/569,816, filed on Dec. 8, 1995, now Pat. No. 5,760,100, which is a continuation-in-part of application No. 08/301,166, filed on Sep. 6, 1994, now abandoned.

(30) Foreign Application Priority Data

Apr. 4, 1995 (DE) .......................................... 95810221
May 19, 1995 (CH) ............................................. 1496/95

(51) Int. Cl.
*C08K 3/00* (2006.01)

(52) U.S. Cl. .................. 523/107; 523/106; 523/108
(58) Field of Classification Search ................. None
See application file for complete search history.

(56) References Cited

To view the complete listing of prior art documents cited during the proceeding for Reexamination Control Number 90/010,896, please refer to the USPTO's public Patent Application Information Retrieval (PAIR) system under the Display References tab.

*Primary Examiner* — Ling Xu

(57) ABSTRACT

An ophthalmic lens suited for extended-wear periods of at least one day on the eye without a clinically significant amount of corneal swelling and without substantial wearer discomfort. The lens has a balance of oxygen permeability and ion or water permeability, with the ion or water permeability being sufficient to provide good on-eye movement, such that a good tear exchange occurs between the lens and the eye. A preferred lens is a copolymerization product of a oxyperm macromer and an ionoperm monomer. The invention encompasses extended wear contact lenses, which include a core having oxygen transmission and ion transmission pathways extending from the inner surface to the outer surface.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 89-96 and 98-100 is confirmed.

Claims 1-88 and 97 were not reexamined.

\* \* \* \* \*